(12) United States Patent
Zhou et al.

(10) Patent No.: US 12,356,911 B2
(45) Date of Patent: Jul. 15, 2025

(54) GROUP OF UDP-GLYCOSYLTRANSFERASE FOR CATALYZING CARBOHYDRATE CHAIN ELONGATION AND APPLICATION THEREOF

(71) Applicant: GSYNBIOT (SHANGHAI) CO., LTD, Shanghai (CN)

(72) Inventors: Zhihua Zhou, Shanghai (CN); Wei Wei, Shanghai (CN); Xing Yan, Shanghai (CN); Chengshuai Yang, Shanghai (CN); Chaojing Li, Shanghai (CN); Yongjun Wei, Shanghai (CN); Pingping Wang, Shanghai (CN)

(73) Assignee: GSYNBIOT (SHANGHAI) CO., LTD, Shanghai (CN)

( * ) Notice: Subject to any disclaimer, the term of this patent is extended or adjusted under 35 U.S.C. 154(b) by 0 days.

(21) Appl. No.: 17/976,715

(22) Filed: Oct. 28, 2022

(65) Prior Publication Data

US 2023/0203458 A1  Jun. 29, 2023

Related U.S. Application Data

(62) Division of application No. 16/614,944, filed as application No. PCT/CN2018/087678 on May 21, 2018, now Pat. No. 11,542,484.

(30) Foreign Application Priority Data

May 19, 2017 (CN) .................... CN201710359069.7

(51) Int. Cl.
| | |
|---|---|
| A01H 1/00 | (2006.01) |
| A01H 5/06 | (2018.01) |
| C12N 9/10 | (2006.01) |
| C12P 19/18 | (2006.01) |

(52) U.S. Cl.
CPC ................ *A01H 5/06* (2013.01); *A01H 1/00* (2013.01); *C12N 9/1048* (2013.01); *C12P 19/18* (2013.01)

(58) Field of Classification Search
None
See application file for complete search history.

(56) References Cited

U.S. PATENT DOCUMENTS

2016/0115515 A1* 4/2016 Zhou .................. C12P 19/56
                                                            435/254.2

FOREIGN PATENT DOCUMENTS

| CN | 104232723 A | 12/2014 |
|---|---|---|
| CN | 104854235 A | 8/2015 |
| CN | 105177100 A | 12/2015 |
| CN | 107058446 B | 8/2017 |
| CN | 110592040 A | 12/2019 |
| JP | 2020520656 A | 7/2020 |
| KR | 101765369 B1 | 3/2016 |
| KR | 102338008 B1 | 12/2021 |

OTHER PUBLICATIONS

Wang et al., Metab. Eng., 29:97-105, 2015.*
Wang et al., UniProt Database, Acc. No. A0A0D5ZD60, Metab. Eng. 29:97-105, 2015.*
International Search Report & Written Opinion; PCT Application No. PCT/CN2018/087678; dated Aug. 2, 2018.
English translation of International Search Report & Written Opinion; PCT Application No. PCT/CN2018/087678; dated Aug. 2, 2018.
International Preliminary Report on Patentability; PCT Application No. PCT/CN2018/087678; dated Nov. 28, 2019.
English abstract of CN 107058446; retrieved from www.espacenet.com on Jun. 16, 2021.
English abstract of CN 105177100; retrieved from www.espacenet.com on Jun. 16, 2021.
English abstract of CN 104854235; retrieved from www.espacenet.com on Jun. 16, 2021.
Abstract of Wang, Pingping et al., "Production of bioactive ginsenosides Rh2 and Rg3 by metabolically engineered yeasts", Metabolic Engineering, vol. 29; May 31, 2015.
Kim, Yun-Soo, et al. "Ginseng metabolic engineering: regulation of genes related to ginsenoside biosynthesis." Journal of Medicinal Plants Research 3.13 (2009): 1270-1276 (Year: 2009).
English abstract of CN 104232723; retrieved from www.espacenet.com on Apr. 20, 2023.

(Continued)

*Primary Examiner* — Phuong T Bui
(74) *Attorney, Agent, or Firm* — NKL Law; Bin Lu; Allen Xue

(57) ABSTRACT

The present invention relates to a group of glycosyltransferase, and an application thereof. Specifically, provided is using glycosyltransferase GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, and PNUGT29-15, as well as derived polypeptides thereof to catalyze the first glycosyl at position C-20, the first glycosyl at position C-6, and the first glycosyl at position C-3 of a tetracyclic triterpene compound substrate to elongate a carbohydrate chain, thereby obtaining a catalytic reaction of ginsenoside products such as ginsenoside Rg3, ginsenoside Rd, ginseno-side Rb 1, ginsenoside Rb3, saponin DMGG, saponin DMGX, gypenoside LXXV, gypenoside XVII, gypenoside XIII, gypenoside IX, notoginsenoside U, and notoginsenoside R1, notoginsenoside R2, notoginsenoside R3, 3-0-13-(D-xylopyranosyl)-13-(D-glucopyra-nosyl)-PPD, 3-0-13-(D-xylopyranosyl)-13-(D-glucopyranosyl)-CK, 20-O-Glucosylginsenoside Rf, and Ginsenoside F3. Glycosyltrans-ferase in the present invention can further be applied to construction of artificially synthesized ginsenoside, novel ginsenoside, and derivatives thereof.

2 Claims, 8 Drawing Sheets

Specification includes a Sequence Listing.

(56) References Cited

OTHER PUBLICATIONS

English abstract of KR 101765369; retrieved from www.espacenet.com on Apr. 20, 2023.
English abstract of CN 110592040; retrieved from www.espacenet.com on Apr. 20, 2023.

* cited by examiner

SEQUENCE LISTING

```
Sequence total quantity: 134
SEQ ID NO: 1                moltype = DNA   length = 18
FEATURE                     Location/Qualifiers
misc_feature                1..18
                            note = primer
source                      1..18
                            mol_type = other DNA
                            organism = synthetic construct
SEQUENCE: 1
cagagttcat catggata                                                  18

SEQ ID NO: 2                moltype = DNA   length = 19
FEATURE                     Location/Qualifiers
misc_feature                1..19
                            note = primer
source                      1..19
                            mol_type = other DNA
                            organism = synthetic construct
SEQUENCE: 2
ctagcataca aagaaagag                                                 19

SEQ ID NO: 3                moltype = DNA   length = 1455
FEATURE                     Location/Qualifiers
misc_feature                1..1455
                            note = GT29-32
source                      1..1455
                            mol_type = other DNA
                            organism = Panax ginseng
SEQUENCE: 3
ggggatcctc tagagatatc cagagttcat catggataac caagaaggta gaatcagtat    60
agcgttgcta ccatttttag cccatggtca catatctccc ttctttgagc tagccaaaca   120
actcgcaaaa agaaattgca atgttttcct ctgttctacc ccaatcaatc ttagctccat   180
caagaataag gattcctctg cttctataaa actagtagag cttcatcttc cctcttcccc   240
tgatcttccc cctcactacc acaccacaaa tggcctccct tcccatctca tggtcccact   300
cagaaacgcc tttgaaacag cagccccac cttctctgaa atccttaaaa ccttaaaccc    360
tgatttgctt atttatgatt tcaatccctc atgggcaccg gaaatcgctt cgtctcacaa   420
tattccggca gtttatttcc taacctcggc agcagccacc tcttccatgg gcctacatgc   480
tttcaaaaac tcaggtgaaa atacccatt tccagatttt tatgataaca gtaatattac    540
ccctgaacca ccttctgcag ataaaatgaa gttatttcat gattttgtcg cttgtttcaa   600
acgatcttgc gacattattt tgattaagag ttttagagaa ctggaaggga aatatattga   660
ttttctttcc actttatcta agaaaacttt ggttcctgtt ggtccactcg ttcaagatcc   720
tatgggacat gatgaagatc caaaacagg gcatcttata aactggcttg acaagagggc   780
tgaatctaca gtggtgtttg tctgctttgg aagtgagtat tttccctcca atgaggaatt   840
ggaagaatta gcaattgggc tagagattag catggttagt ttcatattgg ctgtgagatt   900
tcctgaagga gagaaaaag ggattttacc agagggggttt gttcaaaggg taggagacag    960
aggattggtt gtggagggtg gggctccaca ggcaagaatt ttaggacatt caagcaccgg   1020
tgggtttgtg agccattgtg ggtggagttc tattatggag agtgtgaagt ttgggtgtcc   1080
agtaattgcc atggccaggc atcttgatca gcctttgaat gctaagctgg cggcggaggt   1140
tggtgtgggc atggaggtta tgagagatga aaatgggaag tataagagag aagcgattgc   1200
agaggtaata agaaaagtcg tgatggagaa aaatggggag gttatgagga ggaaagcaag   1260
ggaattgagt gagaaaatga agagataggag agagcaattg attgatgggg cagtggagga   1320
gctagtacaa atttgtaaga agaagaaaga tgaacaatag tagtaataga ctaatttttt   1380
tcccttaaaa atcattttga atgcgcttag gttgggcttt gaactctttc tttgtatgct   1440
aggatatcgt cgacc                                                    1455

SEQ ID NO: 4                moltype = AA   length = 442
FEATURE                     Location/Qualifiers
REGION                      1..442
                            note = misc_feature - GT29-32
source                      1..442
                            mol_type = protein
                            organism = Panax ginseng
SEQUENCE: 4
MDNQEGRISI ALLPFLAHGH ISPFFELAKQ LAKRNCNVFL CSTPINLSSI KNKDSSASIK    60
LVELHLPSSP DLPPHYHTTN GLPSHLMVPL RNAFETAAPT FSEILKTLNP DLLIYDFNPS   120
WAPEIASSHN IPAVYFLTSA AATSSMGLHA FKNSGEKYPF PDFYDNSNIT PEPPSADKMK   180
LFHDFVACFK RSCDIILIKS FRELEGKYID FLSTLSKKTL VPVGPLVQDP MGHDEDPKTG   240
HLINWLDKRA ESTVVFVCFG SEYFPSNEEL EELAIGLEIS MVSFILAVRF PEGEKKGILP   300
EGFVQRVGDR GLVVEGWAPQ ARILGHSSTG GFVSHCGWSS IMESVKFGVP VIAMARHLDQ   360
PLNAKLAAEV GVGMEVMRDE NGKYKREAIA EVIRKVVMEK NGEVMRRKAR ELSEKMKEIG   420
EQLIDRAVEE LVQICKKKKD EQ                                            442

SEQ ID NO: 5                moltype = DNA   length = 1461
FEATURE                     Location/Qualifiers
misc_feature                1..1461
                            note = GT29-33
source                      1..1461
                            mol_type = other DNA
```

```
                        organism = Panax ginseng
SEQUENCE: 5
ccggggatcc tctagagata tccagagttc atcatggata tcgaaaaagg tagaatcagt    60
atagttatgc tgccattttt agcccatggc cacatttctc cattctttga gctagccaag   120
catctctcaa aaagaaattg taatatattc ctctgttcta ccccaatcaa tcttagctcc   180
atcaagaaca gagtatctga taaggattcc tctgcttcta taaaactagt agagcttcat   240
cttccctctt ccccctgatct tccccctcac taccacacca caaatggcct cccttcccat   300
ctcatggtcc cactcagaaa cgcctttgaa acagcagccc ccaccttctc tgaaatcctt   360
aaaaccttaa accctgattt gcttatttat gatttcaatc cctcatgggc accggaaatc   420
gcttcgtctc acaatattcc ggcagtttat ttcctaacct cggcagcagc cacctcttcc   480
atgggcctac atgctttcaa aaactcaggt gaaaaatacc catttccaga tttttatgat   540
aacagtaata ttacccctga accaccttct gcagataaaa tgaagttatt tcatgatttt   600
gtcgcttgtt tcaaacgatc ttgcgacatt attttgatta gagttttag agaactggaa   660
gggaaatata ttgattttct ttccacttta tctaagaaa ctttggttcc tgttggtcca   720
ctcgttcaag atccatggg acatgatgaa gatccaaaaa cagggcatct tataaactgg   780
cttgacaaga gggctgaatc tacagtggtg tttgtctgct ttggaagtga gtattttccc   840
tccaatgagg aattggaaga attagcaatt gggctagaga ttagcatggt tagtttcata   900
ttggctgtga gattcctga aggagagaaa aaagggattt taccagaggg gtttgttcaa   960
agggtaggag acagaggatt ggttgtggag gggtgggctc cacagtcaag aattttagga  1020
cattcaagca ccggtgggtt tgtgagccat tgtgggtgga gttctattat ggagagtgtg  1080
aagtttgggg ttccagtaat tgccatggcc aggcatcttg atcagccttt gaatgctaag  1140
ctggcggcgg aggttggtgt gggcatggag gttatggagg atgaaaatgg gaagtataag  1200
agagaagcga ttgcagaggt aataagaaaa gtcgtgatgg agaaaaatgg ggaggttatg  1260
aggaggaaag caaggaatt gagtgagaaa atgaaagtga aggagagca agagattggt  1320
agggcggtga aggagctagt acaaatttgt aagaagaaga agcagcacgc acaatattaa  1380
tagtactttt taacccttta gtcatttttta tgagctaagg tcgagttttg aactctttct  1440
ttgtatgcta ggatatcgtc g                                            1461

SEQ ID NO: 6                   moltype = AA  length = 448
FEATURE                        Location/Qualifiers
REGION                         1..448
                               note = misc_feature - GT29-33
source                         1..448
                               mol_type = protein
                               organism = Panax ginseng
SEQUENCE: 6
MDIEKGRISI VMLPFLAHGH ISPFFELAKH LSKRNCNIFL CSTPINLSSI KNRVSDKDSS    60
ASIKLVELHL PSSPDLPPHY HTTNGLPSHL MVPLRNAFET AAPTFSEILK TLNPDLLIYD   120
FNPSWAPEIA SSHNIPAVYF LTSAAATSSM GLHAFKNSGE KYPFPDFYDN SNITPEPPSA   180
DKMKLFHDFV ACFKRSCDII LIKSFRELEG KYIDFLSTLS KKTLVPVGPL VQDPMGHDED   240
PKTGHLINWL DKRAESTVVF VCFGSEYFPS NEELEELAIG LEISMVSFIL AVRFPEGEKK   300
GILPEGFVQR VGDRGLVVEG WAPQSRILGH SSTGFVSHC GWSSIMESVK FGVPVIAMAR    360
HLDQPLNAKL AAEVGVGMEV MRDENGKYKR EAIAEVIRKV VMEKNGEVMR RKARELSEKM   420
KVKGEQEIGR AVEELVQICK KKKQHAQY                                     448

SEQ ID NO: 7                   moltype = DNA  length = 1447
FEATURE                        Location/Qualifiers
misc_feature                   1..1447
                               note = GT29-34
source                         1..1447
                               mol_type = other DNA
                               organism = Panax ginseng
SEQUENCE: 7
gggatcctct agagatatcc agagttcatc atggatatcg aaaaaggtag aatcattata    60
gttatgctgc cattttagc ccatggccac atttctcc tctttgagct agccaagcat   120
ctctcaaaaa gaaattgtaa tatattcctc tgttcaccc aatcaatct tagctccatc   180
aagaacagag tatctgataa ggattcctct gcttctataa aactagtaga gcttcatctt   240
ccctcttccc ctgatcttcc ccctcactac acaccacaca atggcctccc ttcccatctc   300
atggtcccac tcagaaacgc ctttgaaaca gcagcccca cctctctga aatccttaaa   360
accttaaacc ctgatttgct tatttatgat ttcaatcccct catgggcacc ggaaatcgct   420
tcgtctcaca atattccggc agtttatttc ctaacctcgg cagcagccac ctcttccatg   480
ggcctacatg ctttcaaaaa ctcaggtgaa aaatacccat ttccagattt ttatgataac   540
agtaatatta cccctgaacc accttctgca gataaaatga agttatttca tgattttgtc   600
gcttgtttca aacgatcttg cgacattatt ttgattaaga gttttagaga actggaaggg   660
aaatatattg attttctttc cactttatct aagaaaactt tggttcctgt tggtccactc   720
gttcaagatc ctatgggaca tgatgaagat ccaaaaacag gcatcttat aaactggctt   780
gacaagaggc tgaatctac agtggtgttt gtctgctttg gaagtgagta ttttccctcc   840
aatgaggaat tggaagaatt agcaattggg ctagagatta gcatggttag tttcatattg   900
gctgtgagat tcctgaagg agagaaaaaa gggattttac cagaggggtt tgttcaaagg   960
gtaggagaca gaggattggt tgtggagggg tgggctccac aggcaagaat tttaggacat  1020
tcaagcaccg gtgggtttgt gagccattgt gggtggagtt ctattatgga gagtgtgaag  1080
tttggggttc cagtaattgc catggccagg catcttgatc agcctttgaa tgctaagctg  1140
gcggcggagg ttggtgtggg catggaggtt atgagagatg aaaatgggaa gtataagaga  1200
gaaggccattg aaggtaat aagaaaagtc gttgtgatgg agaaaatggg gaggttatgag  1260
agaaagcaa gggaattgag tgagaaaatg aaagagaaag gagaggaaga gattgatagg  1320
gcagtggagg agctagtaca aatttgtaag aagaagaaga tgcacaata gtaatagtag  1380
tagtactaat tttgaatgcg cttaggttgg gttttgaact cttctttgt atgctaggat  1440
atcgtcg                                                            1447
```

```
SEQ ID NO: 8              moltype = AA   length = 446
FEATURE                   Location/Qualifiers
REGION                    1..446
                          note = misc_feature - GT29-34
source                    1..446
                          mol_type = protein
                          organism = Panax ginseng
SEQUENCE: 8
MDIEKGRIII VMLPFLAHGH ISPFFELAKH LSKRNCNIFL CSTPINLSSI KNRVSDKDSS   60
ASIKLVELHL PSSPDLPPHY HTTNGLPSHL MVPLRNAFET AAPTFSEILK TLNPDLLIYD  120
FNPSWAPEIA SSHNIPAVYF LTSAAATSSM GLHAFKNSGE KYPFPDFYDN SNITPEPPSA  180
DKMKLFHDFV ACFKRSCDII LIKSFRELEG KYIDFLSTLS KKTLVPVGPL VQDPMGHDED  240
PKTGHLINWL DKRAESTVVF VCFGSEYFPS NEELEELAIG LEISMVSFIL AVRFPEGEKK  300
GILPEGFVQR VGDRGLVVEG WAPQARILGH SSTGGFVSHC GWSSIMESVK FGVPVIAMAR  360
HLDQPLNAKL AAEVGVGMEV MRDENGKYKR EGIAEVIRKV VVEKSGEVMR RKARELSEKM  420
KEKGEEEIDR AVEELVQICK KKKDAQ                                      446

SEQ ID NO: 9              moltype = DNA   length = 23
FEATURE                   Location/Qualifiers
misc_feature              1..23
                          note = primer
source                    1..23
                          mol_type = other DNA
                          organism = synthetic construct
SEQUENCE: 9
gttcaaagcc aacctaagc gca                                           23

SEQ ID NO: 10             moltype = DNA   length = 26
FEATURE                   Location/Qualifiers
misc_feature              1..26
                          note = primer
source                    1..26
                          mol_type = other DNA
                          organism = synthetic construct
SEQUENCE: 10
acagcaagag agagacacag agttca                                       26

SEQ ID NO: 11             moltype = DNA   length = 1418
FEATURE                   Location/Qualifiers
misc_feature              1..1418
                          note = GT29-4
source                    1..1418
                          mol_type = other DNA
                          organism = Panax ginseng
SEQUENCE: 11
acagcaagag agagacacag agttcattca tggataacca agaaggtaga atcagtatag   60
cgttgctacc attttagcc catggccaca tttctccatt ctttgagcta gccaagcatc  120
tctcaaaaag aaattgtaat atattcctct gttctacccc aatcaatctt agctccatca  180
agaacagaat atctgataag gattcctctg cttctataaa actagtagag cttcatcttc  240
catcttcccc tgatcttcct cctcactacc acaccacaaa tggcctccct tcccatctca  300
tggtcccact cagaaacgcc tttgaaacag cagccccac cttctctgaa atccttaaaa  360
ccttaaaccc tgatttgctt atttatgatt tcaatccctc atgggcaccg agatcgcttc  420
cgtctcacaa tattccggca gttttgtttca taattgggg agcagcctcc ttttccatga  480
gcctacatag tttcaaaaac ccaggtgaaa aatacccatt tctagatttt gatgataaca  540
gtaatattac ccctgaacca ccttcagcag ataacatgca gttattactt gatttttatga  600
cttgtttcga acgatcttgc gacattattt tgattaagag ttttagaaga ctagaaggga  660
aatattttga ttttttattct actttatctg ataaaacttt ggttcctgtt ggtccactcg  720
ttcaagatcc tatgggccat aatgaagatc caaaaacaga gcagtttata aactggcttg  780
acaaaagggc tgaatctaca gtggtgtttg tctgctttgg aagtgagtat tttctctcca  840
atgaggaatt ggaagaagta gcaattgggc tagaattgag catggttaat ttcatatggt  900
ctgtgagatt aattgaagga gagaaaaaag gggttttacc agaggggttt gttcaaaggg  960
taggagacag aggattggtt gtggaggggt gggctccaca gcaagaatt ttaggacatt 1020
caagcaccgg tgggtttgtg agccattgtg ggtgagttc tattacgag agtatgaagt 1080
ttggggttcc agtaattgcc atggccaggc atcttgatca gccttttgaat ggtaagctgg 1140
cggcggaggt tggtgtgggc atggaggttg tgagagatga aaatgggaag tataagagag 1200
aagggattgc agaggtaata agaaaagtcg ttgtggagaa aagtgggagg ttatgagga 1260
ggaaagcaag ggaattgagt gagaaaatga aagagaaagg agaggaagag attgatgg 1320
cagtggagga gctagtacaa atttgtaaga agaagaaaga tgcacaatag taatagtagt 1380
agtactaatt ttgaatgcgc ttaggttggg ctttgaac                        1418

SEQ ID NO: 12             moltype = AA   length = 446
FEATURE                   Location/Qualifiers
REGION                    1..446
                          note = misc_feature - GT29-4
source                    1..446
                          mol_type = protein
                          organism = Panax ginseng
SEQUENCE: 12
MDNQEGRISI ALLPFLAHGH ISPFFELAKH LSKRNCNIFL CSTPINLSSI KNRISDKDSS   60
```

```
ASIKLVELHL PSSPDLPPHY HTTNGLPSHL MVPLRNAFET AAPTFSEILK TLNPDLLIYD    120
FNPSWAPEIA SSHNIPAVCF IIGGAASFSM SLHSFKNPGE KYPFLDFDDN SNITPEPPSA    180
DNMKLLLDFM TCFERSCDII LIKSFRELEG KYFDFYSTLS DKTLVPVGPL VQDPMGHNED    240
PKTEQFINWL DKRAESTVVF VCFGSEYFLS NEELEEVAIG LEISMVNFIW AVRLIEGEKK    300
GVLPEGFVQR VGDRGLVVEG WAPQARILGH SSTGGFVSHC GWSSITESMK FGVPVIAMAR    360
HLDQPLNGKL AAEVGVGMEV VRDENGKYKR EGIAEVIRKV VVEKSGEVMR RKARELSEKM    420
KEKGEEEIDR AVEELVQICK KKKDAQ                                         446

SEQ ID NO: 13           moltype = DNA   length = 1434
FEATURE                 Location/Qualifiers
misc_feature            1..1434
                        note = GT29-5
source                  1..1434
                        mol_type = other DNA
                        organism = Panax ginseng
SEQUENCE: 13
acagcaagag agagacacag agttcattca tggataacca aaagggtaga atcagtatag      60
ttatgctgcc attttagcc catggccaca tttctccatt ctttgagcta gccaagcatc     120
tctcaaaaag aaattgtaat atattcctct gttctacccc aatcaatctt agctccatca     180
agaacagaat atctgataag gattcctctg cttctataaa actagtagag cttcatcttc     240
catcttccc tgatcttcct cctcactacc acaccacaaa tggcctccct tcccatctca     300
tggtcccact cagaaacgcc tttgaaacag cagccccac cttctctgaa atccttaaaa     360
ccttaaaccc tgatttgctt atttatgatt tcaatccctc atgggcaccg agatcgctt     420
cgtctcacaa tattccggca gtttgtttca taattggggg agcagcctcc ttttccatga     480
gcctacatag tttcaaaaac ccaggtgaaa aatacccatt tctagatttt gatgataaca     540
gtaatattac ccctgaacca ccttcagcag ataacatga gttattactt gattttatga     600
cttgtttcga acgatcttgc gacattattt tgattaagga ttttagagaa ctagaaggga     660
aatatatcga tttgctttcc actttatctg ataaaacttt ggttcctgtt ggtccactcg     720
ttcaagatcc tatgggccat aatgaagatc caaaaacaga gcagattata aactggcttg     780
acaaaaggc tgaatctaca gtggtgtttg tctgcttttgg aagtgagtat tttctctcca     840
atgaggaatt ggaagaagta gcaattgggc tagagattag catggttaat ttcatatgga     900
ctgtgagatt aattgaagga gagaaaaag gggtttacc agagggattt gttcaaaggg     960
taggagacag aggattggtt gtggaggggt gggctccaca ggcaagaatt ttaggacatt    1020
caaggaccgg tgggtttgtg agccattgtg ggtggagttc tattgcggag agtatgaagt    1080
ttggggttcc agtaattgcc atggccaggc atcttgatca gcctttgaat ggtaagctga    1140
cggcggaggt tggtgtgggc atggaggttg tgagagatga aaatgggaag tataagagag    1200
aagggattgc agaggtaata agaaaagtcg ttgtggagaa aagtggggag gttatcagga    1260
ggaaagcaag ggaattgagt gagaaaatga aagagatagg agagcaattg attgataggg    1320
cagtggagga gctagtacaa atttgtaaga agaagaaaga tgaacaatag tagtaataga    1380
ctaattttt tcccttaaa atcattttga atgcgcttag gttgggcttt gaac            1434

SEQ ID NO: 14           moltype = AA   length = 446
FEATURE                 Location/Qualifiers
REGION                  1..446
                        note = misc_feature - GT29-5
source                  1..446
                        mol_type = protein
                        organism = Panax ginseng
SEQUENCE: 14
MDNQKGRISI VMLPFLAHGH ISPFFELAKH LSKRNCNIFL CSTPINLSSI KNRISDKDSS     60
ASIKLVELHL PSSPDLPPHY HTTNGLPSHL MVPLRNAFET AAPTFSEILK TLNPDLLIYD    120
FNPSWAPEIA SSHNIPAVCF IIGGAASFSM SLHSFKNPGE KYPFLDFDDN SNITPEPPSA    180
DNMKLLLDFM TCFERSCDII LIKSFRELEG KYIDLLSTLS DKTLVPVGPL VQDPMGHNED    240
PKTEQIINWL DKRAESTVVF VCFGSEYFLS NEELEEVAIG LEISMVNFIW AVRLIEGEKK    300
GVLPEGFVQR VGDRGLVVEG WAPQARILGH SSTGGFVSHC GWSSIAESMK FGVPVIAMAR    360
HLDQPLNGKL AAEVGVGMEV VRDENGKYKR EGIAEVIRKV VVEKSGEVIR RKARELSEKM    420
KEIGEQLIDR AVEELVQICK KKKDEQ                                         446

SEQ ID NO: 15           moltype = DNA   length = 1484
FEATURE                 Location/Qualifiers
misc_feature            1..1484
                        note = GT29-7
source                  1..1484
                        mol_type = other DNA
                        organism = Panax ginseng
SEQUENCE: 15
aatgaaatta tacagagagg gagagaaaca gagttcattc atggataacc aaaaggtag      60
aatcagtata gcgttgctac cattttagc ccatggtcac atatctccct tctttgagct    120
agccaaacaa ctcgcaaaaa gaaattgcaa tgttttcctc tgttctaccc caatcaatct    180
tagctccatc aagaacagag tatctgataa ggattcctct gcttctataa aactagtaga    240
gcttcatctt ccatcttccc tgatcttcc tcctcactac cacaccacaa atggcctccc    300
ttcccatctc atgatcccac tcagaaacgc ctttgataca gcaggcccca ccttctctga    360
aatccttaaa acccttaaacc ctgatttgct tatttatgat ttcaatccct catgggcacc    420
ggagatcgct tcgtctcaca taattccggc agtttgttta ataattggtg gagcagcctc    480
cttttccatg agcctacata gtttcaaaaa cccaggtgaa aaatacccat tctagattt    540
tgatgataac agtaatatta ccctgaacca ccttcagca gataacatga gctattaat    600
taattttatg acttgtttcg aacgatcttg cgacattatt tgattaaga gttttagaga    660
actagaaggg aaatatttg atttttttc cactttatct gataaaactt tggttcctgt    720
tggtccactc gttcaagatc ctatgggcca taatgaagat ccaaaaacag agcagtttat    780
```

-continued

```
aaactggctt gacaaaaggg ctgaatctac agtggtgttt gtctgctttg gaagtgagtg   840
ttttctctcc aatgaggaat tggaagaagt agcgattggg ctagagatta gcatggttaa   900
tttcatatgg gctgtgagat taattgaagg agagaaaaaa ggggttttac cagagggggtt   960
tgttcaaagg gtaggagaca gaggattggt tgtggaggag tgggctccac aggcaagaat  1020
tttaggacat tcaagcaccg gtgggtttgt gagccattgt gggtggaatt ctattacgga  1080
gagtatgaag tttggggttc cagtaattgc catggccagg cattttgatc agcctttgaa  1140
tggtaagctg gcggcggagg ttggtgtggg catggaggtt gtgagagatg aaaatgggaa  1200
gtataagaga gaagggattg cagaggtaat aagaaaagtc gttgtggaga aaagtgggga  1260
ggttatcagg aggaaaagcaa gggaattgag tgagaaaatg aaagagaaag gagcaaga   1320
gattgatagg gtagtggagg agctagtaca aatttgtaag aagaagaaag atgaacaata  1380
gtaataggac tacttttttt acctttagaa tcatttgaa tgcgcttaag gttgagtttt   1440
taactttttc tttgtacttg tactttgtgt tgtgaagaaa acca                   1484

SEQ ID NO: 16              moltype = AA   length = 446
FEATURE                    Location/Qualifiers
REGION                     1..446
                           note = misc_feature - GT29-7
source                     1..446
                           mol_type = protein
                           organism = Panax ginseng
SEQUENCE: 16
MDNQKGRISI ALLPFLAHGH ISPFFELAKQ LAKRNCNVFL CSTPINLSSI KNRVSDKDSS    60
ASIKLVELHL PSSPDLPPHY HTTNGLPSHL MIPLRNAFDT AGPTFSEILK TLNPDLLIYD   120
FNPSWAPEIA SSHNIPAVCF IIGGAASSSM SLHSFKNPGE KYPFLDFDDN SNITPEPPSA   180
DNMKLLINFM TCFERSCDII LIKSFRELEG KYFDFFSTLS DKTLVPVGPL VQDPMGHNED   240
PKTEQFINWL DKRAESTVVF VCFGSECFLS NEELEEVAIG LEISMVNFIW AVRLIEGEKK   300
GVLPEGFVQR VGDRGLVVEE WAPQARILGH SSTGGFVSHC GWNSITESMK FGVPVIAMAR   360
HFDQPLNGKL AAEVGVGMEV VRDENGKYKR EGIAEVIRKV VVEKSGEVIR RKARELSEKM   420
KEKGEQEIDR VVEELVQICK KKKDEQ                                       446

SEQ ID NO: 17              moltype = DNA   length = 1432
FEATURE                    Location/Qualifiers
misc_feature               1..1432
                           note = GT29-9
source                     1..1432
                           mol_type = other DNA
                           organism = Panax ginseng
SEQUENCE: 17
acagcaagag agagacacag agttcattca tggataacca aaagggtaga atcagtatag    60
ttatgctgcc attttagcc catggccaca tttctccatt ctttgagcta gccaagcatc   120
tctcaaaaag aaattgtaat atattcctct gttctacccc aatcaatctt agctccatca   180
agaacagaat atctgataag gattcctctg ctttatataaa actagtagag cttcatcttc   240
catcttcccc tgatcttcct cctcactacc acaccacaaa tggcctccct tcccatctca   300
tggtcccact cagaaacgcc tttgaaacag cagcccccac cttctctgaa atccttaaaa   360
ccttaaaccc tgatttgctt attttatgatt tcaatccctc atgggcaccg gagatcgctt   420
cgtctcacaa tattccggca gttgttca taattggggg agcagcctcc ttttccatga    480
gcctacataga tttcaaaaac ccaggtgaaa aatacccatt tctagatttt gatgataaca   540
gtaatattac ccctgaacca ccttcagcag ataacatgaa gttattactt gatttttga    600
cttgttcga acgatcttgc gacattattt tgattaagag ttttagagaa ctagaaggga   660
aatatttga tttttattct actttatctg ataaaacttt ggttcctgtt ggtccactcg   720
ttcaagatcc tatgggccat aatgaagatc caaaaacaga gcagttttata aactggctta   780
acaaaagggc tgaatctaca gtggtgtttg tctgctttgg aagtgagtat tttctctcca   840
atgaggaatt ggaagaagta gcaattgggc tagagattag catggttaat ttcatatggg   900
ctgtgagatt aattgaagga gagaaaaaag gggttttacc agagggatttg gttcaaaggg   960
taggagacag aggattggtt gtggagggggt gggctccaca ggcaagaatt ttaggacatt  1020
caagcaccgg tgggtttgtg agccattgtg gtggagttc tattgcgag agtatgaagt   1080
ttggggttcc agtaattgcc atggccaggc atcttgatca gcctttgaat ggtaagctgg  1140
cggcggaggt tggtgtgggc atggaggttg tgagagatga aaatgggaag tataagagag  1200
aagatattgc aggggtaata agaaaagtcg tggtggagaa aagtggggag gttatcagga  1260
ggaaagcaag ggaattgagt gagaaaatga aagatagg agagcaattg attgatagga    1320
cagtggagga gctagtacaa aatttgtaaga agaagaaaga tgaacaatag tagtaataga  1380
ctaattttt tcccttaaa atcatttga atgcgcttag gttgggcttt ga               1432

SEQ ID NO: 18              moltype = AA   length = 446
FEATURE                    Location/Qualifiers
REGION                     1..446
                           note = misc_feature - GT29-9
source                     1..446
                           mol_type = protein
                           organism = Panax ginseng
SEQUENCE: 18
MDNQKGRISI VMLPFLAHGH ISPFFELAKH LSKRNCNIFL CSTPINLSSI KNRISDKDSS    60
ASIKLVELHL PSSPDLPPHY HTTNGLPSHL MVPLRNAFET AAPTFSEILK TLNPDLLIYD   120
FNPSWAPEIA SSHNIPAVCF IIGGAASFSM SLHSFKNPGE KYPFLDFDDN SNITPEPPSA   180
DNMKLLLDFM TCFERSCDII LIKSFRELEG KYFDFYSTLS DKTLVPVGPL VQDPMGHNED   240
PKTEQFINWL DKRAESTVVF VCFGSEYFLS NEELEEVAIG LEISMVNFIW AVRLIEGEKK   300
GVLPEGFVQR VGDRGLVVEG WAPQARILGH SSTGGFVSHC GWSSIAESMK FGVPVIAMAR   360
HLDQPLNGKL AAEVGVGMEV VRDENGKYKR EDIAGVIRKV VVEKSGEVIR RKARELSEKM   420
KEIGEQLIDR AVEELVQICK KKKDEQ                                       446
```

```
SEQ ID NO: 19            moltype = DNA  length = 1434
FEATURE                  Location/Qualifiers
misc_feature             1..1434
                         note = GT29-11
source                   1..1434
                         mol_type = other DNA
                         organism = Panax ginseng
SEQUENCE: 19
acagcaagag agagacacag agttcattca tggataacca aaagggtaga atcagtatag    60
ttatgctgcc attttagcc catggccaca tttctccatt ctttgagcta gccaagcatc   120
tctcaaaaag aaattgtaat atattcctct gttctacccc aatcaatctt agctccatca   180
agaacagaat atctgataag gattcctctg cttctataaa actagtagag cttcatcttc   240
catcttcccc tgatcttcct cctcactacc acaccacaaa tggcctccct tcccatctca   300
tggtccact cagaaacgcc tttgaaacag cagcccccac cttctctgaa atccttaaaa    360
ccttaaaccc tgatttgctt atttatgatt tcaatccctc atgggcaccg agatcgctt    420
cgtctcacaa tattccggca gtttgtttca taattggggg agcagcctcc ttttccatga   480
gcctacatag tttcaaaaac ccaggtgaaa aatacccatt tctagatttt gatgataaca   540
gtaatattac ccctgaacca ccttcagcag ataacatgaa gttattactt gattttatga   600
cttgtttcga acgatcttgc gacattattt tgattaagag ttttagagaa ctagaaggga   660
aatattttga ttttttattct actttatctg ataaaacttt ggttcctgtt ggtccactcg   720
ttcaagatcc tatgggccat aatgaagatc caaaaacaga gcagtttata aactggcttg   780
acaaaagggc tgaatctaca gtggtgtttg tctgctttgg aagtgagtat tttctctcca   840
atgaggaatt ggaagaagta gcaattgggc tagagattag catggttaat ttcatatggg   900
ctgtgagatt aattgaagga gagaaaaaag gggtttacc agaggggttt gttcaaaggg    960
taggagacag aggattggtt gtggagggggt gggctccaca ggcaagaatt ttaggacatt  1020
caagcaccgg tgggtttgtg agccattgtg ggtggagttc tattacggag agtatgaagt  1080
ttggggttcc agtaattgcc atggccaggc attttgatca gcctttgaat gctaagctgg  1140
cggcggaggt tggtgtgggc atggaggttg tgagagatga aaatgggaag tataagagag  1200
aagatattgc aggggtaata gaaaaagtcg tggtggagaa aagtggggaa gttatcagga  1260
ggaaagcaag ggaattgagt gagaaaatga aagagatagg agagcaattg attgatgagg  1320
cagtggagga gctagtacaa atttgtaaga agaagaaaga tgaacaatag tagtaataga  1380
ctaatttttt tccctttaaa atcatttga atgcgcttag gttgggcttt gaat          1434

SEQ ID NO: 20            moltype = AA   length = 446
FEATURE                  Location/Qualifiers
REGION                   1..446
                         note = misc_feature - GT29-11
source                   1..446
                         mol_type = protein
                         organism = Panax ginseng
SEQUENCE: 20
MDNQKGRISI VMLPFLAHGH ISPFFELAKH LSKRNCNIFL CSTPINLSSI KNRISDKDSS    60
ASIKLVELHL PSSPDLPPHY HTTNGLPSHL MVPLINAFET AGPTFSEILK TLNPDLLIYD   120
FNPSWAPEIA SSHNIPAVYF LTTAAASSSI GLHAFKNPGE KYPFPDFYDN SNNTPEPPSA   180
DNMKLLHDFI ACFERSCDII LIKSFIELEG KYIDLLSTLS DKTLVPVGPL VQDPMGHNED   240
PKTEQIINWL DKRAESTVVF VCFGSEYFLS NEELEEVAIG LEISMVNFIW AVRLIEGEKK   300
GVLPEGFVQR VGDRGLVVEG WAPQARILGH SSTGGFVSHC GWSSIAESMK FGVPVIAMAR   360
HLDQPLNGKL AAEVGVGMEV VRDENGKYKR EGIAEVIRKV VVEKSGEVMR RKARELSEKM   420
KEKGEEEIDR AVEELVQICK KKKDAQ                                       446

SEQ ID NO: 21            moltype = DNA  length = 1434
FEATURE                  Location/Qualifiers
misc_feature             1..1434
                         note = GT29-13
source                   1..1434
                         mol_type = other DNA
                         organism = Panax ginseng
SEQUENCE: 21
acagcaagag agagacacag agttcattca tggataacca aaagggtaga atcagtatag    60
ttatgctgcc attttagcc catggccaca tttctccatt ctttgagcta gccaagcatc   120
tctcaaaaag aaattgtaat atattcctct gttctacccc aatcaatctt agctccatca   180
agaacagaat atctgataag gattcctctg cttctataaa actagtagag cttcatcttc   240
catcttcccc tgatcttcct cctcactacc acaccacaaa tggcctccct tcccatctca   300
tggtccact cagaaacgcc tttgaaacag cagcccccac cttctctgaa atccttaaaa    360
ccttaaaccc tgatttgctt atttatgatt tcaatccctc atgggcaccg agatcgctt    420
cgtctcacaa tattccggca gtttgtttca taattggggg agcagcctcc ttttccatga   480
gcctacatag tttcaaaaac ccaggtgaaa aatacccatt tctagatttt gatgataaca   540
gtaatattac ccctgaacca ccttcagcag ataacatgaa gttattactt gattttatga   600
cttgtttcga acgatcttgc gacattattt tgattaagag ttttagagaa ctagaaggga   660
aatattttga ttttttattct actttatctg ataaaacttt ggttcctgtt ggtccactcg   720
ttcaagatcc tatgggccat aatgaagatc caaaaacaga gcagtttata aactggcttg   780
acaaaagggc tgaatctaca gtggtgtttg tctgctttgg aagtgagtat tttctctcca   840
atgaggaatt ggaagaagta gcaattgggc tagagattag catggttaat ttcatatggg   900
ctgtgagatt aattgaagga gagaaaaaag gggtttacc agaggggttt gttcaaaggg    960
taggagacag aggattggtt gtggagggggt gggctccaca ggcaagaatt ttaggacatt  1020
caagcaccgg tgggtttgtg agccattgtg ggtggagttc tattacggag agtatgaagt  1080
ttggggttcc agtaattgcc atggccaggc attttgatca gcctttgaat gctaagctgg  1140
cggcggaggt tggtgtggtc atggaggttg tgagagatga aaatgggaag tataagagag  1200
```

```
aagatattgc aggggtaata agaaaagtcg tggtggagaa aagtggggag gttatcagga  1260
ggaaagcaag ggaattgagt gagaaaatga aagagatagg agagcaattg attgataggg  1320
cagtggagga gctagtacaa atttgtaaga agaagaaaga tgaacaatag tagtaataga  1380
ctaattttt tccctttaaa atcatttga atgcgcttag gttgggcttt gaac          1434
```

```
SEQ ID NO: 22           moltype = AA   length = 446
FEATURE                 Location/Qualifiers
REGION                  1..446
                        note = misc_feature - GT29-13
source                  1..446
                        mol_type = protein
                        organism = Panax ginseng
SEQUENCE: 22
MDNQKGRISI VMLPFLAHGH ISPFFELAKH LSKRNCNIFL CSTPINLSSI KNRISDKDSS   60
ASIKLVELHL PSSPDLPPHY HTTNGLPSHL MVPLRNAFET AAPTFSEILK TLNPDLLIYD  120
FNPSWAPEIA SSHNIPAVCF IIGGAASFSM SLHSFKNPGE KYPFLDFDDN SNITPEPPSA  180
DNMKLLLDFM TCFERSCDII LIKSFRELEG KYFDFYSTLS DKTLVPVGPL VQDPMGHNED  240
PKTEQFINWL DKRAESTVVF VCFGSEYFLS NEELEEVAIG LEISMVNFIW AVRLIEGEKK  300
GVLPEGFVQR VGDRGLVVEG WAPQARILGH SSTGGFVSHC GWSSITESMK FGVPVIAMAR  360
HFDQPLNAKL AAEVGVVMEV VRDENGKYKR EDIAGVIRKV VVEKSGEVIR RKARELSEKM  420
KEIGEQLIDR AVEELVQICK KKKDEQ                                       446
```

```
SEQ ID NO: 23           moltype = DNA   length = 1422
FEATURE                 Location/Qualifiers
misc_feature            1..1422
                        note = GT29-17
source                  1..1422
                        mol_type = other DNA
                        organism = Panax ginseng
SEQUENCE: 23
acagcaagag agagacacag agttcattca tggataacca agaaggtaga atcagtatag   60
cgttgctacc attttagcc catggtcaca tatctccctt ctttgagcta gccaaacaac  120
tcgcaaaaag aaaattgcaat gttttcctct gttctacccc aatcaatctt agctccatca  180
agaataagga ttcctctgct tctataaaac tagttgagct tcatcttcca tcttcccctg  240
atcttcctcc tcactatcac accacaaatg gcctcccttc ccatctcatg gtcccactca  300
taaacgcctt tgaaacagca ggccccacct tctctgaaat ccttaaaacc ttaaccctg   360
atttgcttat ttatgatttc aatccctcat gggcaccgga gatcgcttcg tctcacaata  420
ttccggcagt ttgtttcata attgggggag cagcctcctt ttccatgagc ctacatagtt  480
tcaaaaaccc aggtgaaaaa tacccatttc tagattttga tgataacgat aatattaccc  540
ctgaaccacc ttcagcagat aacatgaagt tattacttga ttttatgact tgtttcgaac  600
gatcttgcga cattatttg attaagagtt ttagagaact agaagggaaa tatttgatt   660
tttattctac tttatctgat aaaactttgg ttcctgttgg tccactcgtt caagatccta  720
tgggccataa tgaagatcca aaaacagagc agtttataaa ctggcttgac aaaagggctg  780
aatctacagt ggtgttttgtc tgctttggaa gtgagtattt tctctccaat gaggaattgg  840
aagaagtagc aattgggcta gagattagca tggttaattt catatgggct gtgagattaa  900
ttgaaggaga gaaaaaggg gttttaccag aggggttgt tcaagggta gggacagag     960
gatggttgt ggaggggtgg gctccacagg caagaattt aggacattca agcaccggtg  1020
ggtttgtgag ccattgtggg tggagttcta ttacggagag tatgaagttt ggggttccag  1080
taattgccat ggccaggcat tttgatcagc ctttgaatgc taagctgcg gcggaggttg  1140
gtgtgggcat ggaggttgtg agagatgaaa atggaagta agagagaa gatattgcag   1200
gggtaataag aaaagtcgtg gtggagaaaa gtggggaggt tatcaggaaa agcaaggg   1260
aattgagtga gaaatgaaa gagataggag agcaattgt tgataggca gtggaggagc  1320
tagtacaaat ttgtaagaag aagaaagatg aacaatagta gtaatagact aatttttttc  1380
cctttaaaat cattttgaat gcgcttaggt tgggctttga ac                     1422
```

```
SEQ ID NO: 24           moltype = AA   length = 442
FEATURE                 Location/Qualifiers
REGION                  1..442
                        note = misc_feature - GT29-17
source                  1..442
                        mol_type = protein
                        organism = Panax ginseng
SEQUENCE: 24
MDNQEGRISI ALLPFLAHGH ISPFFELAKQ LAKRNCNVFL CSTPINLSSI KNKDSSASIK   60
LVELHLPSSP DLPPHYHTTN GLPSHLMVPL INAFETAGPT FSEILKTLNP DLLIYDFNPS  120
WAPEIASSHN IPAVCFIIGG AASFSMSLHS FKNPGEKYPF LDFDDNSNIT PEPPSADNMK  180
LLLDFMTCFE RSCDIILIKS FRELEGKYFD FYSTLSDKTL VPVGPLVQDP MGHNEDPKTE  240
QFINWLDKRA ESTVVPVCFG SEYFLSNEEL EEVAIGLEIS MVNFIWAVRL IEGEKKGVLP  300
EGFVQRVGDR GLVVEGWAPQ ARILGHSSTG GFVSHCGWSS ITESMKFGVP VIAMARHFDQ  360
PLNAKLAAEV GVGMEVVRDE NGKYKREDIA GVIRKVVVEK SGEVIRRKAR ELSEKMKEIG  420
EQLIDRAVEE LVQICKKKKD EQ                                           442
```

```
SEQ ID NO: 25           moltype = DNA   length = 1417
FEATURE                 Location/Qualifiers
misc_feature            1..1417
                        note = GT29-18
source                  1..1417
                        mol_type = other DNA
                        organism = Panax ginseng
```

```
SEQUENCE: 25
acagcaagag agagacacag agttcattca tggataacca aaagggtaga atcagtatag    60
ttatgctgcc atttttagcc catggccaca tttctccatt ctttgagcta gccaagcatc   120
tctcaaaaag aaattgtaat atattcctct gttctacccc aatcaatctt agctccatca   180
agaacagaat atctgataag gattcctctg ctttctataaa actagtagag cttcatcttc   240
catcttcccc tgatcttcct cctcactacc acaccacaaa tggcctccct tcccatctca   300
tggtcccact cagaaacgcc tttgaaacag cagccccccac cttctctgaa atccttaaaa   360
ccttaaaccc tgatttgctt atttatgatt tcaatccctc atgggcaccg gagatcgctt   420
cgtctcacaa tattccggca gttgtttca taattggggg agcagcctcc ttttccatga    480
gcctacatag tttcaaaaac ccaggtgaaa aatacccatt tctagatttt gatgataaca   540
gtaatattac ccctgaacca ccttcagcag ataacatgaa gttattactt gattttatga   600
cttgtttcga acgatcttgc gacattattt tgattaagag ttttagagaa ctagaaggaa   660
aatattttga ttttttattct actttatctg ataaaacttt ggttcctgtt ggtccactcg   720
ttcaagatcc tatgggccat aatgaagatc caaaaacaga gcagtttata aactggcttg   780
acaaaagggc tgaatctaca gtggtgtttg tctgctttgg aagtgagtat tttctctcca   840
atgaggaatt ggaagaagta gcaattgggc tagagattag catggttaat ttcatatggg   900
ctgtgagatt aattgaagga gagaaaaaag gggttttacc agaggggttt gttcaaaggg   960
taggagacag aggattggtt gtggaggggt gggctccaca ggcaagaatt ttaggacatt  1020
caagcaccgg tgggtttgtg agccattgtg ggtggagttc tattacggag agtatgaagt  1080
ttgggggttcc agtaattgcc atggccaggc attttgatca gcctttgaat gctaagctgg  1140
cggcggaggt tggtgtgggc atggaggttg tgagagatga aaatgggaag tataagagag  1200
aagatattgc aggggtaata agaaaagtcg tggtggagaa aagtgggag gttatgagga  1260
ggaaagcaag ggaattgagt gagaaaatga aagagaaagg agaggaagag attgataggg  1320
cagtggagga gctagtacaa atttgtaaga agaagaaaga tgcacaatag taatagtagt  1380
agtactaatt ttgaatgcgc ttaggttggg cttaatc                           1417

SEQ ID NO: 26           moltype = AA   length = 446
FEATURE                 Location/Qualifiers
REGION                  1..446
                        note = misc_feature - GT29-18
source                  1..446
                        mol_type = protein
                        organism = Panax ginseng
SEQUENCE: 26
MDNQKGRISI VMLPFLAHGH ISPFFELAKH LSKRNCNIFL CSTPINLSSI KNRISDKDSS    60
ASIKLVELHL PSSPDLPPHY HTTNGLPSHL MVPLRNAFET AAPTFSEILK TLNPDLLIYD   120
FNPSWAPEIA SSHNIPAVCF IIGGAASFSM SLHSFKNPGE KYPFLDFDDN SNITPEPPSA   180
DNMKLLLDFM TCFERSCDII LIKSFRELEG KYFDFYSTLS DKTLVPVGPL VQDPMGHNED   240
PKTEQFINWL DKRAESTVVF VCFGSEYFLS NEELEEVAIG LEISMVNFIW AVRLIEGEKK   300
GVLPEGFVQR VGDRGLVVEG WAPQARILGH SSTGGFVSHC GWSSITESMK FGVPVIAMAR   360
HFDQPLNAKL AAEVGVGMEV VRDENGKYKR EDIAGVIRKV VVEKSGEVMR RKARELSEKM   420
KEKGEEEIDR AVEELVQICK KKKDAQ                                        446

SEQ ID NO: 27           moltype = DNA   length = 1418
FEATURE                 Location/Qualifiers
misc_feature            1..1418
                        note = GT29-24
source                  1..1418
                        mol_type = other DNA
                        organism = Panax ginseng
SEQUENCE: 27
acagcaagag agagacacag agttcattca tggataacca aaagggtaga atcagtatag    60
ttatgctgcc atttttagcc catggccaca tttctccatt ctttgagcta gccaagcatc   120
tctcaaaaag aaattgtaat atattcctct gttctacccc aatcaatctt agctccatca   180
agaacagaat atctgataag gattcctctg ctttctataaa actagtagag cttcatcttc   240
catcttcccc tgatcttcct cctcactacc acaccacaaa tggcctccct tcccatctca   300
tggtcccact cagaaacgcc tttgaaacag cagccccccac cttctctgaa atccttaaaa   360
ccttaaaccc tgatttgctt atttatgatt tcaatccctc atgggcaccg gagatcgctt   420
cgtctcacaa tattccggca gttgtttca taattggggg agcagcctcc ttttccatga    480
gcctacatag tttcaaaaac ccaggtgaaa aatacccatt tctagatttt gatgataaca   540
gtaatattac ccctgaacca ccttcagcag ataacatgaa gttattactt gattttatga   600
cttgtttcga acgatcttgc gacattattt tgattaagag ttttagagaa ctagaaggaa   660
aatattttga ttttttattct actttatctg ataaaacttt ggttcctgtt ggtccactcg   720
ttcaagatcc tatgggccat aatgaagatc caaaaacaga gcagtttata aactggcttg   780
acaaaagggc tgaatctaca gtggtgtttg tctgctttgg aagtgagtat tttctctcca   840
atgaggaatt ggaagaagta gcaattgggc tagagattag catggttaat ttcatatggg   900
ctgtgagatt aattgaagga gagaaaaaag gggttttacc agaggggttt gttcaaaggg   960
taggagacag aggattggtt gtggaggggt gggctccaca ggcaagaatt ttaggacatt  1020
caagcaccgg tgggtttgtg agccattgtg ggtggagttc tattacggag agtatgaagt  1080
ttgggggttcc agtaattgcc atggccaggc attttgatca gcctttgaat gctaagctgg  1140
cggcggaggt tggtgtgggc atggaggttg tgagagatga aaatgggaag tataagagag  1200
aagggattgc agaggtaata agaaaagtcg ttgtggagaa aagtgggag gttatgagga  1260
ggaaagcaag ggaattgagt gagaaaatga aagagaaagg agaggaagag attgataggg  1320
cagtggagga gctagtacaa atttgtaaga agaagaaaga tgcacaatag taatagtagt  1380
agtactaatt ttgaatgcgc ttaggttggg ctttgaac                           1418

SEQ ID NO: 28           moltype = AA   length = 446
FEATURE                 Location/Qualifiers
REGION                  1..446
```

|  |  |
|---|---|
|  | note = misc_feature - GT29-24 |
| source | 1..446 |
|  | mol_type = protein |
|  | organism = Panax ginseng |

SEQUENCE: 28

```
MDNQKGRISI VMLPFLAHGH ISPFFELAKH LSKRNCNIFL CSTPINLSSI KNRISDKDSS    60
ASIKLVELHL PSSPDLPPHY HTTNGLPSHL MVPLRNAFET AAPTFSEILK TLNPDLLIYD   120
FNPSWAPEIA SSHNIPAVCF IIGGAASFSM SLHSFKNPGE KYPFLDFDDN SNITPEPPSA   180
DNMKLLLDFM TCFERSCDII LIKSFRELEG KYFDFYSTLS DKTLVPVGPL VQDPMGHNED   240
PKTEQFINWL DKRAESTVVF VCFGSEYFLS NEELEEVAIG LEISMVNFIW AVRLIEGEKK   300
GVLPEGFVQR VGDRGLVVEG WAPQARILGH SSTGGFVSHC GWSSITESMK FGVPVIAMAR   360
HFDQPLNAKL AAEVGVGMEV VRDENGKYKR EGIAEVIRKV VVEKSGEVMR RKARELSEKM   420
KEKGEEEIDR AVEELVQICK KKKDAQ                                       446
```

|  |  |
|---|---|
| SEQ ID NO: 29 | moltype = DNA  length = 1434 |
| FEATURE | Location/Qualifiers |
| misc_feature | 1..1434 |
|  | note = GT29-25 |
| source | 1..1434 |
|  | mol_type = other DNA |
|  | organism = Panax ginseng |

SEQUENCE: 29

```
acagcaagag agagacacag agttcattca tggataacca aaggggtaga atcagtatag    60
ttatgctgcc attttagcc catggccaca tttctccatt ctttgagcta gccaagcatc   120
tctcaaaaag aaattgtaat atattcctct gttctacccc aatcaatctt agctccatca   180
agaacagaat atctgataag gattcctctg ctttatataa actagtagag cttcatcttc   240
catcttcccc tgatcttcct cctcactacc acaccacaaa tggcctccct tccatctca   300
tggtcccact cagaaacgcc tttgaaacag cagcccccac cttctctgaa atccttaaaa   360
ccttaaaccc tgatttgctt atttatgatt tcaatccctc atgggcaccg gagatcgctt   420
cgtctcacaa tattccggca gtttgtttca taattggggg agcagcctcc ttttccatga   480
gcctacatag tttcaaaaac ccaggtgaaa aatacccatt tctagatttt gatgataaca   540
gtaatattac ccctgaacca cctccagcag ataacatgaa gttattactt gatttatga   600
cttgtttcga acgatcttgc gacattattt tgattaagag ttttagagaa ctagaaggga   660
aatattttga tttttattct actttatctg ataaaactt ggttcctgtt ggtccactcg   720
ttcaagatcc tatgggccat aatgaagatc caaaaacaga gcagtttata aactgcttg   780
acaaaagggc tgaatctaca gtggtgtttg tctgctttgg aagtgagtat tttctccca   840
atgaggaatt ggaagaagta gcaattgggc tagagattag catggttaat ttcatatggg   900
ctgtgagatt aattgaagga gagaaaaaag gggttttacc agaggggttt gttcaaaggg   960
taggagacag aggattggtt gtggagggt gggctccaca ggcaagaatt ttaggacatt  1020
caagcaccgg tgggtttgtg agccattgtg ggtggagttc tattacggag agtatgaagt  1080
ttggggttcc agtaattgcc atggccaggc attttgatca gcctttgaat gctaagctgg  1140
cggcggaggt tggtgtgggc acggaggttg tgagagatga aaatgggaag tataagagag  1200
aagatattgc aggggtaata agaaaagtcg tggtggagaa gttatcagga  1260
ggaaagcaag ggaattgagt gagaaaatga aagagatagg agcaattg attgataggg  1320
cagtggagga gctagtacaa atttgtaaga agaagaaaga tgaacaatag tagtaataga  1380
ctaatttttt tccctttaaa atcatttga atgcgcttag gttgggcttt gaac         1434
```

|  |  |
|---|---|
| SEQ ID NO: 30 | moltype = AA  length = 446 |
| FEATURE | Location/Qualifiers |
| REGION | 1..446 |
|  | note = misc_feature - GT29-25 |
| source | 1..446 |
|  | mol_type = protein |
|  | organism = Panax ginseng |

SEQUENCE: 30

```
MDNQKGRISI VMLPFLAHGH ISPFFELAKH LSKRNCNIFL CSTPINLSSI KNRISDKDSS    60
ASIKLVELHL PSSPDLPPHY HTTNGLPSHL MVPLRNAFET AAPTFSEILK TLNPDLLIYD   120
FNPSWAPEIA SSHNIPAVCF IIGGAASFSM SLHSFKNPGE KYPFLDFDDN SNITPEPPSA   180
DNMKLLLDFM TCFERSCDII LIKSFRELEG KYFDFYSTLS DKTLVPVGPL VQDPMGHNED   240
PKTEQFINWL DKRAESTVVF VCFGSEYFLS NEELEEVAIG LEISMVNFIW AVRLIEGEKK   300
GVLPEGFVQR VGDRGLVVEG WAPQARILGH SSTGGFVSHC GWSSITESMK FGVPVIAMAR   360
HFDQPLNAKL AAEVGVGTEV VRDENGKYKR EDIAGVIRKV VVEKSGEVIR RKARELSEKM   420
KEIGEQLIDR AVEELVQICK KKKDEQ                                       446
```

|  |  |
|---|---|
| SEQ ID NO: 31 | moltype = DNA  length = 43 |
| FEATURE | Location/Qualifiers |
| misc_feature | 1..43 |
|  | note = primer |
| source | 1..43 |
|  | mol_type = other DNA |
|  | organism = synthetic construct |

SEQUENCE: 31

```
taagaaggag atataccatg gataaccaag aaggtagaat cag                      43
```

|  |  |
|---|---|
| SEQ ID NO: 32 | moltype = DNA  length = 44 |
| FEATURE | Location/Qualifiers |
| misc_feature | 1..44 |
|  | note = primer |
| source | 1..44 |

```
                              mol_type = other DNA
                              organism = synthetic construct
SEQUENCE: 32
tgcggccgca agcttgtcga cttgttcatc tttcttcttc ttac                  44

SEQ ID NO: 33                 moltype = DNA  length = 42
FEATURE                       Location/Qualifiers
misc_feature                  1..42
                              note = primer
source                        1..42
                              mol_type = other DNA
                              organism = synthetic construct
SEQUENCE: 33
taagaaggag atataccatg gataaccaaa agggtagaat ca                    42

SEQ ID NO: 34                 moltype = DNA  length = 42
FEATURE                       Location/Qualifiers
misc_feature                  1..42
                              note = primer
source                        1..42
                              mol_type = other DNA
                              organism = synthetic construct
SEQUENCE: 34
tgcggccgca agcttgtcga cttgtgcatc tttcttcttc tt                    42

SEQ ID NO: 35                 moltype = DNA  length = 43
FEATURE                       Location/Qualifiers
misc_feature                  1..43
                              note = primer
source                        1..43
                              mol_type = other DNA
                              organism = synthetic construct
SEQUENCE: 35
taagaaggag atataccatg gataaccaaa aggtagaat cag                    43

SEQ ID NO: 36                 moltype = DNA  length = 43
FEATURE                       Location/Qualifiers
misc_feature                  1..43
                              note = primer
source                        1..43
                              mol_type = other DNA
                              organism = synthetic construct
SEQUENCE: 36
taagaaggag atataccatg gatatcgaaa aaggtagaat cag                   43

SEQ ID NO: 37                 moltype = DNA  length = 39
FEATURE                       Location/Qualifiers
misc_feature                  1..39
                              note = primer
source                        1..39
                              mol_type = other DNA
                              organism = synthetic construct
SEQUENCE: 37
tgcggccgca agcttgtcga catattgtgc gtgctgctt                        39

SEQ ID NO: 38                 moltype = DNA  length = 1344
FEATURE                       Location/Qualifiers
source                        1..1344
                              mol_type = other DNA
                              organism = Panax notoginseng
SEQUENCE: 38
atggatatcg aaaaaggtag aatcagtata gttatgctgc catttttagc ccatggtcac   60
atatctccat tctttgagct agccaagcat ctctcaaaaa gaaattgcaa tatattcctc  120
tgttctaccc caatcaatct tagctccatc aagagcagag tatctgataa ggattcctct  180
gcttctataa aactagtaga gcttcatctt ccatcttccc ctgatcttcc tcctcagtac  240
cacaccacaa atggcctccc ttcccatctc atggtcccac tcaaaaacgc ctttgaaaca  300
gtaggcccca ccttctctga aatccttaaa accttagacc ctgatttgct tatttatgat  360
ttcaatccct catgggcacc ggagatcgct ttgtctcaca atattccggc agttttattc  420
ctaacctcgg cagcagccac ctcttccgtg gccctacgtg ctttgaaaaa cccaggtgaa  480
aaatacccat ttccagattt ttatgataac agtaatatta ccctgaacc accttctgca   540
gataaaatga agctatttca tgattttgtt gcttgtttca acgatcttg cgacattatt   600
ttgattaaga gttttagaga actagaaggg aaatatattg atttgctttc cactttatct  660
aagaaaactt tggttcctgt tggtccactc gttcaagatc ctttgggaca tgatgaagat  720
ccaaaaacag ggcatcttat aaactggctt gacaaaaggg ctgaatctac agtggtgttt  780
gtctgctttg aagtgagta ttttcctcc aatgaggaat tggaagaagt agcaattggg  840
ctagagatta gcatggttaa tttcatattg gctgttagat tcttgaagg agagaaaaaa  900
ggggttttac cagaagggtt tgttcaaagg gtaggagaca gaggattggt tgtggaggg  960
tgggctccaa aggcaagaat tttaggacat tcaagcaccg gtgggtttgt gagccattgt 1020
gggtggagtt ctattatgga gagtgtgaag tttgggggttc cagtaattgc catggccagg 1080
```

```
catcttgatc agcctttgaa tgctaagctg gcggcggagg ttggtgtggg catggaggtt   1140
gtgagagatg aaaatgggaa gtatacgaga gaagcgattg cagaggtaat aagaaaagtt   1200
gtgatggaga aaaatgggga ggttatcagg aggaaagcaa gggaattgag tgataaaatg   1260
aaagagaaag gagagcaaga gattggtagg gcagtggagg agctagtaca aatttgtaag   1320
atgaagaaag acgcacaata ttaa                                          1344

SEQ ID NO: 39          moltype = AA  length = 447
FEATURE                Location/Qualifiers
source                 1..447
                       mol_type = protein
                       organism = Panax notoginseng
SEQUENCE: 39
MDIEKGRISI VMLPFLAHGH ISPFFELAKH LSKRNCNIFL CSTPINLSSI KSRVSDKDSS    60
ASIKLVELHL PSSPDLPPQY HTTNGLPSHL MVPLKNAFET VGPTFSEILK TLDPDLLIYD   120
FNPSWAPEIA LSHNIPAVYF LTSAAATSSV ALRALKNPGE KYPFPDFYDN SNITPEPPSA   180
DKMKLFHDFV ACFKRSCDII LIKSFRELEG KYIDLLSTLS KKTLVPVGPL VQDPLGHDED   240
PKTGHLINWL DKRAESTVVF VCFGSEYFPS NEELEEVAIG LEISMVNFIL AVRFLEGEKK   300
GVLPEGFVQR VGDRGLVVEG WAPQARILGH SSTGGFVSHC GWSSIMESVK FGVPVIAMAR   360
HLDQPLNAKL AAEVGVGMEV VRDENGKYTR EAIAEVIRKV VMEKNGEVIR RKARELSDKM   420
KEKGEQEIGR AVEELVQICK MKKDAQY                                       447

SEQ ID NO: 40          moltype = DNA  length = 1329
FEATURE                Location/Qualifiers
source                 1..1329
                       mol_type = other DNA
                       organism = Panax notoginseng
SEQUENCE: 40
atggataacc aaaaaggtag aatcagtata gcgttgctac cattttttagc ccatggtcac    60
atatctcct tctttgagct agccaaacaa ctggcaaaaa gaaattgcaa tgttttcctc    120
tgttctaccc caatcaatct tagctccatc aagaataagg attcctctgc ttctgtaaaa   180
ctagttgagc ttcatcttcc atcttcccct gatcttcctc ctcactatca caccacaaat   240
ggcctccctt cccatctcat ggtcccactc agaaacgcct ttgaaacagt aggccccacc   300
ttctctgaaa tccttaaaac cttaaaccct gatttgctta tttatgattt caatccctca   360
tgggcaccgg agatcgcttc gtctcacaat attccgagca tttattttcct aaccacggca   420
gcagccagct cttccattgg cctacatgct tcaaaaacc caggtgaaaa atacccattt    480
ccagatttt atgataacag taatattacc cctgaaccac cttctgcaga taacatgaag    540
ctacttcatg atttatcgc ttgtttcgaa cgatcttgcg atattatttt gattaagagt    600
tttagagaac tagaagggaa atatattgat ttgctttcca cttatctga taaaactttg    660
gttcctgttg gtcccactcgt tcaagatcct atgggccata tgaagatcc aaaaacagag    720
cagattataa actggcttga caaaagggct gaatctacga tggtgtttgt ctgctttgga    780
agtgagtatt ttctctccaa tgaggaattg aagaagtag caattgggct agagattagc    840
atggttaatt tcatatgggc tgtgagatta attgaaggag agaaaaaagg ggttttacca    900
gagggtttg ttcaaagggt aggagacaga ggattggttg tggggggtg ggctccacaa    960
gcaagaattt taggacattc aagcaccggt gggtttgtga ccattgtgg gtggagttct   1020
attgcggaga gtatgaggtt tggggttcca gtaattgcca tggctaggca tcttgatcag   1080
cctttgaatg ctaagctggc ggcggaggtt ggtgtgggca tggaggttgt aagagatgat   1140
aatgggaaat ataagaggga aggggattgca gaggtaataa gaaaagtct tgtggagaaa   1200
agtgggagg ttatcaggag gaaagcaagg gagttgagtg agaaatgaa agagaaagga   1260
gagcaagaga ttgatagggc agtggaggag ctagtacaaa tttgtaagaa gaagaaagat   1320
gcacaatag                                                           1329

SEQ ID NO: 41          moltype = AA  length = 442
FEATURE                Location/Qualifiers
source                 1..442
                       mol_type = protein
                       organism = Panax notoginseng
SEQUENCE: 41
MDNQKGRISI ALLPFLAHGH ISPFFELAKQ LAKRNCNVFL CSTPINLSSI KNKDSSASVK    60
LVELHLPSSP DLPPHYHTTN GLPSHLMVPL RNAFETVGPT FSEILKTLNP DLLIYDFNPS   120
WAPEIASSHN IPAVYFLTTA AASSSIGLHA FKNPGEKYPF PDFYDNSNIT PEPPSADNMK   180
LLHDFIACFE RSCDIILIKS FRELEGKYID LLSTLSDKTL VPVGPLVQDP MGHNEDPKTE   240
QIINWLDKRA ESTVVFVCFG SEYFLSNEEL EEVAIGLEIS MVNFIWAVRL IEGEKKGVLP   300
EGFVQRVGDR GLVVEGWAPQ ARILGHSSTG GFVSHCGWSS IAESMRFGVP VIAMARHLDQ   360
PLNAKLAAEV GVGMEVVRDD NGKYKREGIA EVIRKVVVEK SGEVIRRKAR ELSEKMKEKG   420
EQEIDRAVEE LVQICKKKKD AQ                                            442

SEQ ID NO: 42          moltype = DNA  length = 1344
FEATURE                Location/Qualifiers
source                 1..1344
                       mol_type = other DNA
                       organism = Panax notoginseng
SEQUENCE: 42
atggatatcg agaaaggtag aatcagtata gttatgctac cattttttagc ccatggtcac    60
atatctccat tctttgagct agccaagcat ctctcaaaaa gaaattgcaa tatattcctc   120
tgttctaccc caatcaatct tagctccatc aagaacagag tatctgataa ggattcctct   180
gcttcaataa aactagtaga gcttcatctt ccatcttccc ctgatcttcc tcctcagtac   240
cacaccacaa atggcctccc ttcccatctc atggtcccac tcaaaaacgc ctttgaaaca   300
gtaggccca cccttctctga aatccttaaa accttagacc ctgatttgct tatttatgat   360
ttcaatcccc tcatgggcac cggagatcgc ttgtctcaca atattccggc agtttatttc   420
```

```
ctaacctcgg cagcagccac ctcttccgtg gccctacgtg ctttgaaaaa cccaggtgaa    480
aaatacccat ttccagattt ttatgataac agtaatatta cccctgaacc accttctgca    540
gataaaatga agctatttca tgattttgtt gcttgtttca aacgatcttg cgacattatt    600
ttgattaaga gttttagaga actagaaggg aaatatattg atttgctttc cactttatct    660
aagaaaactt tggttcctgt tggtccactc gttcaagatc ctttgggaca tgatgaagat    720
ccaaaaacag ggcatcttat aaactggctt gacaaaaggg ctgaatctac agtggtgttt    780
gtctgctttg gaagtgagta ttttccctcc aatgaggaat ggaagaagt agcaattggg    840
ctagagatta gcatggttaa tttcatattg gctgtgagat ttcttgaagg agagaaaaaa    900
ggggttttac cagaggggtt tgttcaaagg gtaggagaca gaggattggt tgtggagggg    960
tgggctccac aggcaagaat tttaggacat tcaagcaccg gtggtttgt gagccattgt    1020
gggtggagtt ctattatgga gagtgtgaag tttggggttc cagtaattgc catggccagg    1080
catcttgatc agcctttgaa tgctaagctg cggcggagg tcgtgtggg catggaggtt    1140
gtgagagatg aaaatgggaa gtataagaga aagcgattg cagaggtaat aagaaaagtc    1200
gtgatggaga aaaatgggga ggttatcagg aggaaagcaa gggaattgag tgagaaaatg    1260
aaagagacag gagagcaaga gattggtagg gcagtggagg agctagtaca aatttgtaag    1320
atgaagaaag acgcacaata ttaa                                          1344

SEQ ID NO: 43           moltype = AA  length = 447
FEATURE                 Location/Qualifiers
source                  1..447
                        mol_type = protein
                        organism = synthetic construct
SEQUENCE: 43
MDIEKGRISI VMLPFLAHGH ISPFFELAKH LSKRNCNIFL CSTPINLSSI KNRVSDKDSS    60
ASIKLVELHL PSSPDLPPQY HTTNGLPSHL MVPLKNAFET VGPTFSEILK TLDPDLLIYD   120
FNPSWAPEIA LSHNIPAVYF LTSAAATSSV ALRALKNPGE KYPFPDFYDN SNITPEPPSA   180
DKMKLFHDFV ACFKRSCDII LIKSFRELEG KYIDLLSTLS KKTLVPVGPL VQDPLGHDED   240
PKTGHLINWL DKRAESTVVF VCFGSEYFPS NEELEEVAIG LEISMVNFIL AVRFLEGEKK   300
GVLPEGFVQR VGDRGLVVEG WAPQARILGH SSTGGFVSHC GWSSIMESVK FGVPVIAMAR   360
HLDQPLNAKL AAEVGVGMEV VRDENGKYKR EAIAEVIRKV VMEKNGEVIR RKARELSEKM   420
KETGEQEIGR AVEELVQICK MKKDAQY                                      447

SEQ ID NO: 44           moltype = DNA  length = 1344
FEATURE                 Location/Qualifiers
source                  1..1344
                        mol_type = other DNA
                        organism = Panax notoginseng
SEQUENCE: 44
atggatatcg aaaaaggtag aatcagtata gttatgctgc cattttttagc ccatggtcac    60
atatctccat tctttgagct agccaagcat ctctcaaaaa gaaattgcaa tatattcctc   120
tgttctaccc caatcaatct tagctccatc aagaacagag tatctgataa ggattcctct   180
gcttctataa aactagtaga gcttcatctt ccatcttccc ctgatcttcc tcctcagtac   240
cacaccacaa atggcctccc ttcccatctc atggtcccac tcaaaaacgc ctttgaaaca   300
gtaggcccca ccttctctga atccttaaaa accttagacc ctgatttgct tatttatgat   360
ttcaatccct catgggcacc ggagatcgct ttgtctcaca atattccggc agtttatttc   420
ctaacctcgg cagcagccac ctcttccgtg gccctacgtg ctttgaaaaa cccaggtgaa   480
aaatacccat ttccagattt ttatgataac agtaatatta cccctgaacc accttctgca   540
gataaaatga agctatttca tgattttgtt gcttgtttca aacgatcttg cgacattatt   600
ttgattaaga gttttagaga actagaaggg aaatatattg atttgctttc cactttatct   660
aagaaaactt tggttcctgt tggtccactc gttcaagatc ctttgggaca tgatgaagat   720
ccaaaaacag ggcatcttat aaactggctt gacaaaaggg ctgaatctac agtggtgttt   780
gtctgctttg gaagtgagta ttttccctcc aatgaggaat ggaagaagt agcaattggg   840
ctagagatta gcatggttaa tttcatattg gctgttagat ttcttgaagg agagaaaaaa   900
ggggttttac cagaagggtt tgttcaaagg gtaggagaca gaggattggt tgtggagggg   960
tgggctccac aggcaagaat tttaggacat tcaagcaccg gtggtttgt gagccattgt    1020
gggtggagtt ctattatgga gagtgtgaag tttggggttc cagtaattgc catggccagg    1080
catcttgatc agcctttgaa tgctaagctg cggcggagg ttgtgtggg catggaggtt    1140
gtgagagatg aaaatgggaa gtatacgaga aagcgattg cagaggtaat aagaaaagtt    1200
gtgatggaga aaaatgggga ggttatcagg aggaaagcaa gggaattgag tgataaaatg    1260
aaagagaaag gagagcaaga gattggtagg gcagtggagg agctagtaca aatttgtaag    1320
atgaagaaag acgcacaata ttaa                                          1344

SEQ ID NO: 45           moltype = AA  length = 447
FEATURE                 Location/Qualifiers
source                  1..447
                        mol_type = protein
                        organism = Panax notoginseng
SEQUENCE: 45
MDIEKGRISI VMLPFLAHGH ISPFFELAKH LSKRNCNIFL CSTPINLSSI KNRVSDKDSS    60
ASIKLVELHL PSSPDLPPQY HTTNGLPSHL MVPLKNAFET VGPTFSEILK TLDPDLLIYD   120
FNPSWAPEIA LSHNIPAVYF LTSAAATSSV ALRALKNPGE KYPFPDFYDN SNITPEPPSA   180
DKMKLFHDFV ACFKRSCDII LIKSFRELEG KYIDLLSTLS KKTLVPVGPL VQDPLGHDED   240
PKTGHLINWL DKRAESTVVF VCFGSEYFPS NEELEEVAIG LEISMVNFIL AVRFLEGEKK   300
GVLPEGFVQR VGDRGLVVEG WAPQARILGH SSTGGFVSHC GWSSIMESVK FGVPVIAMAR   360
HLDQPLNAKL AAEVGVGMEV VRDENGKYTR EAIAEVIRKV VMEKNGEVIR RKARELSDKM   420
KEKGEQEIGR AVEELVQICK MKKDAQY                                      447

SEQ ID NO: 46           moltype = DNA  length = 1344
FEATURE                 Location/Qualifiers
```

| source | 1..1344 |
| --- | --- |
| | mol_type = other DNA |
| | organism = Panax notoginseng |

SEQUENCE: 46

```
atggatatcg aaaaaggtag aatcagtata gttatgctgc catttttagc ccatggtcac   60
atatctccat tctttgagct agccaagcat ctctcaaaaa gaaattgcaa tatattcctc  120
tgttctaccc caatcaatct tagctccatc aagaacagag tatctgataa ggattcctct  180
gcttctataa aactagtaga gcttcatctt ccatcttccc ctgatcttcc tcctcagtac  240
cacaccacaa atggcctccc ttcccatctc atggtcccac tcaaaaacgc ctttgaaaca  300
gtaggcccca ccttctctga aatccttaaa accttagacc ctgatttgct tatttatgat  360
ttcaatccct catgggcacc ggagatcgct ttgtctcaca atattccggc agtttatttc  420
ctaacctcgg cagcagccac ctcttccgtg gccctacgtg ctttgaaaaa cccaggtgaa  480
aaatacccat ttccagattt ttatgataac agtaatatta cccctgaacc accttctgca  540
gataaaatga agctatttca tgattttgtt gcttgtttca aacgatcttg cgacattatt  600
ttgattaaga gttttagaga actagaaggg aaatatattg atttgctttc cactttatct  660
aagaaaactt tggttcctgt tggtccactc gttcaagatc ctttgggaca tgatgaagat  720
ccaaaaacag ggcatcttat aaactggctt gacaaaaggg ctgaatctac agtggtgttt  780
gtctgctttg gaagtgagta ttttccctcc aatgaggaat tggaagaagt agcaattggg  840
ctagagatta gcatggttaa tttcatattg gctgttagat tcttgaagg agagaaaaaa  900
ggggttttac cagaagggtt tgttcaaagg gtaggagaca gaggattggt tgtggagggg  960
tgggctccac aggcaagaat tttaggacat tcaagcaccg tgggtttgt gagccattgt 1020
gggtggagtt ctattatgga gagtgtgaag tttgggttc cagtaattgc catggccagg 1080
catcttgatc agcctttgaa tgctaagctg gcggcggagg ttggtgtggg catggaggtt 1140
gtgagagatg aaaatgggaa gtatacgaga gaagcgattg cagaggtaat aagaaaagtt 1200
gtgatgagag aaaatgggga ggttatcagg aggaaagcaa gggaattgag tgataaaatg 1260
aaaagagaaag gagagcaaga gattggtagg gcagtggagg agctagtaca aatttgtaag 1320
atgatgaaag acgcacaata ttaa                                       1344
```

| SEQ ID NO: 47 | moltype = AA length = 447 |
| --- | --- |
| FEATURE | Location/Qualifiers |
| source | 1..447 |
| | mol_type = protein |
| | organism = Panax notoginseng |

SEQUENCE: 47

```
MDIEKGRISI VMLPFLAHGH ISPFFELAKH LSKRNCNIFL CSTPINLSSI KNRVSDKDSS   60
ASIKLVELHL PSSPDLPPQY HTTNGLPSHL MVPLKNAFET VGPTFSEILK TLDPDLLIYD  120
FNPSWAPEIA LSHNIPAVYF LTSAAATSSV ALRALKNPGE KYPFPDFYDN SNITPEPPSA  180
DKMKLFHDFV ACFKRSCDII LIKSFRELEG KYIDLLSTLS KKTLVPVGPL VQDPLGHDED  240
PKTGHLINWL DKRAESTVVF VCFGSEYFPS NEELEEVAIG LEISMVNFIL AVRFLEGEKK  300
GVLPEGFVQR VGDRGLVVEG WAPQARILGH SSTGGFVSHC GWSSIMESVK FGVPVIAMAR  360
HLDQPLNAKL AAEVGVGMEV VRDENGKYTR EAIAEVIRKV VMEKNGEVIR RKARELSDKM  420
KEKGEQEIGR AVEELVQICK MMKDAQY                                    447
```

| SEQ ID NO: 48 | moltype = DNA length = 1344 |
| --- | --- |
| FEATURE | Location/Qualifiers |
| source | 1..1344 |
| | mol_type = other DNA |
| | organism = Panax notoginseng |

SEQUENCE: 48

```
atggatatcg aaaaaggtag aatcagtata gttatgctgc catttttagc ccatggtcac   60
atatctccat tctttgagct agccaagcat ctctcaaaaa gaaattgcaa tatattcctc  120
tgttctaccc caatcaatct tagctccatc aagaacagag tatctggtaa ggattcctct  180
gcttctataa aactagtaga gcttcatctt ccatcttccc ctgatcttcc tcctcagtac  240
cacaccacaa atggcctccc ttcccatctc atggtcccac tcaaaaacgc ctttgaaaca  300
gtaggcccca ccttctctga aatccttaaa accttagacc ctgatttgct tatttatgat  360
ttcaatccct catgggcacc ggagatcgct ttgtctcaca atattccggc agtttatttc  420
ctaacctcgg cagcagccac ctcttccgtg gccctacgtg ctttgaaaaa cccaggtgaa  480
aaatacccat ttccagattt ttatgataac agtaatatta cccctgaacc accttctgca  540
gataaaatga agctatttca tgattttgtt gcttgtttca aacgatcttg cgacattatt  600
ttgattaaga gttttagaga actagaaggg aaatatattg atttgctttc cactttatct  660
aagaaaactt tggttcctgt tggtccactc gttcaagatc ctttgggaca tgatgaagat  720
ccaaaaacag ggcatcttat aaactggctt gacaaaaggg ctgaatctac agtggtgttt  780
gtctgctttg gaagtgagta ttttccctcc aatgaggaat tggaagaagt agcaattggg  840
ctagagatta gcatggttaa tttcatattg gctgttagat tcttgaagg agagaaaaaa  900
ggggttttac cagaagggtt tgttcaaagg gtaggagaca gaggattggt tgtggagggg  960
tgggctccac aggcaagaat tttaggacat tcaagcaccg tgggtttgt gagccattgt 1020
gggtggagtt ctattatgga gagtgtgaag tttgggttc cagtaattgc catggccagg 1080
catcttgatc agcctttgaa tgctaagctg gcggcggagg ttggtgtggg catggaggtt 1140
gtgagagatg aaaatgggaa gtatacgaga gaagcgattg cagaggtaat aagaaaagtt 1200
gtgatgagag aaaatgggga ggttatcagg aggaaagcaa gggaattgag tgataaaatg 1260
aaaagagaaag gagagcaaga gattggtagg gcagtggagg agctagtaca aatttgtaag 1320
atgaagaaag acgcacaata ttaa                                       1344
```

| SEQ ID NO: 49 | moltype = AA length = 447 |
| --- | --- |
| FEATURE | Location/Qualifiers |
| source | 1..447 |
| | mol_type = protein |
| | organism = Panax notoginseng |

SEQUENCE: 49

```
MDIEKGRISI VMLPFLAHGH ISPFFELAKH LSKRNCNIFL CSTPINLSSI KNRVSGKDSS   60
ASIKLVELHL PSSPDLPPQY HTTNGLPSHL MVPLKNAFET VGPTFSEILK TLDPDLLIYD  120
FNPSWAPEIA LSHNIPAVYF LTSAAATSSV ALRALKNPGE KYPFPDFYDN SNITPEPPSA  180
DKMKLFHDFV ACFKRSCDII LIKSFRELEG KYIDLLSTLS KKTLVPVGPL VQDPLGHDED  240
PKTGHLINWL DKRAESTVVF VCFGSEYFPS NEELEEVVFG LEISMVNFIL AVRFLEGEKK  300
GVLPEGFVQR VGDRGLVVEG WAPQARILGH SSTGGFVSHC GWSSIMESVK FGVPVIAMAR  360
HLDQPLNAKL AAEVGVGMEV VRDENGKYTR EAIAEVIRKV VMEKNGEVIR RKARELSDKM  420
KEKGEQEIGR AVEELVQICK MKKDAQY                                     447

SEQ ID NO: 50           moltype = DNA   length = 1344
FEATURE                 Location/Qualifiers
source                  1..1344
                        mol_type = other DNA
                        organism = Panax notoginseng
SEQUENCE: 50
atggatatcg aaaaaggtag aatcagtata gttatgctgc cattttttagc ccatggtcac    60
atatctccat tctttgagct agccaagcat ctctcaaaaa gaaattgcaa tatattcctc   120
tgttctaccc caatcaatct tagctccatc aagaacagag tatctgataa ggattcctct   180
gcttctataa aactagtaga gcttcatctt ccatcttccc ctgatcttcc tcctcagtac   240
cacaccacaa atggcctccc ttcccatctc atggtcccac tcaaaaacgc ctttgaaaca   300
gtaggcccca ccttctctga aatccttaaa acccttagacc ctgatttgtt tatttatgat   360
ttcaatccct catgggcacc ggagatcgct tgtctcacaa atattccggc agtttattc    420
ctaacctcgg cagcagccac ctcttccgtg gccctacgtg ctttgaaaaa cccaggtgaa   480
aaatacccat tccagatttt ttatgataac agtaatatta cccctgaacc acctttctgca  540
gataaaatga agctatttca tgattttgtt gcttgtttca acgatcttg cgacattatt    600
ttgattaaga gttttagaga actagaaggg aaatatattg atttgctttc cactttatct   660
aagaaaactt tggttcctgt tggtccactc gttcaagatc ctttgggaca tgatgaagat   720
ccaaaaacag gcatcttat aaactggctt gacaaaaggg ctgaatctac agtggtgttt    780
gtctgctttg gaagtgagta tttccctcc aatgaggaat tggaagaagt agcaattggg    840
ctagagatta gcatggttaa tttcatattg gctgttaagt tcttgaagg agagaaaaa    900
ggggttttac cagaagggtt tgttcaaagg gtaggagaca gaggattggt tgtggagggg   960
tgggctccac aggcaagaat tttaggacat tcaagcaccg gtgggtttgt gagccattgt  1020
gggtggagtt ctattatgga gagtgtgaag tttggggttc cagtaattgc catggccagg  1080
catcttgatc agccttgaa tgctaagctg gcggcggagg ttggtgtggg catggaggtt  1140
gtgagagatg aaaatgggaa gtatacgaga gaagcgattc cagaggtaat aagaaaagtt  1200
gtgatggaga aaaatgggga ggttatcagg aggaaagcaa gggaattgag tgataaaatg  1260
aaagagaaag gagagcaaga gattggtagg cagtggagg agctagtaca aatttgtaag  1320
atgaagaaag acgcacaata ttaa                                        1344

SEQ ID NO: 51           moltype = AA   length = 447
FEATURE                 Location/Qualifiers
source                  1..447
                        mol_type = protein
                        organism = Panax notoginseng
SEQUENCE: 51
MDIEKGRISI VMLPFLAHGH ISPFFELAKH LSKRNCNIFL CSTPINLSSI KNRVSDKDSS   60
ASIKLVELHL PSSPDLPPQY HTTNGLPSHL MVPLKNAFET VGPTFSEILK TLDPDLFIYD  120
FNPSWAPEIA LSHNIPAVYF LTSAAATSSV ALRALKNPGE KYPFPDFYDN SNITPEPPSA  180
DKMKLFHDFV ACFKRSCDII LIKSFRELEG KYIDLLSTLS KKTLVPVGPL VQDPLGHDED  240
PKTGHLINWL DKRAESTVVF VCFGSEYFPS NEELEEVAIG LEISMVNFIL AVRFLEGEKK  300
GVLPEGFVQR VGDRGLVVEG WAPQARILGH SSTGGFVSHC GWSSIMESVK FGVPVIAMAR  360
HLDQPLNAKL AAEVGVGMEV VRDENGKYTR EAIAEVIRKV VMEKNGEVIR RKARELSDKM  420
KEKGEQEIGR AVEELVQICK MKKDAQY                                     447

SEQ ID NO: 52           moltype = DNA   length = 1338
FEATURE                 Location/Qualifiers
source                  1..1338
                        mol_type = other DNA
                        organism = Panax notoginseng
SEQUENCE: 52
atcgagaaag gtagaatcag tatagttatg ctaccatttt tagcccatgg tcacatatct    60
ccattctttg agctagccaa gcatctctca aaaagaaatt gcaatatatt cctctgttct   120
accccaatca atcttagctc catcaagaac agagtatctg ataaggattc ctctgcttca   180
ataaaactag tagagcttca tcttccctcc atcttcctca gtaccaccac             240
acaaatggcc tcccttccca tctcatggtc ccactcaaaa acgcctttga aacagtaggc   300
ccacccttct ctgaaatcct taaaacctta cccctgatt tgcttattta tgatttcaat    360
ccctcatggg caccggagat cgctttgtct cacaatattc cggcagttta tttcctaacc   420
tcggcagcag ccacctcttc cgtggcccta cgtgctttga aaaacccagg tgaaaaatac   480
ccatttccag atttttatga taacagtaat attaccccctg aaccaccctt ctgcagataaa  540
atgaagctat tcatgatttt gttgcttgt tcaaacgat cttgcgacat tattttgatt    600
aagagtttta gaactaga agggaaatat attgatttgc tttccacttt atctaagaaa    660
actttggttc ctgttggtcc actcgttcaa gatcctttgg gacatgatga agatccaaaa   720
acagggcatc ttataaactg gcttgacaaa agggctgaat ctacagtggt gtttgtctgc   780
tttggaagtg agtatttcc ctcccaatgag gaattggaag aagtagcaat tgggctagag  840
attagcatgg ttaatttcat attggctgtg atttcttg aaggagagaa aaaagggggt   900
taccagagg ggtttgttca agggtagga gacagaggat tggttgtgga ggggtgggct   960
ccacaggcaa gaatttaggg acattcaagc accggtgggt tgtgagcca ttgtgggtgg  1020
agttctatta tggagagtgt gaagtttggg gttccagtaa ttgccatggc caggcatctt  1080
gatcagcctt tgaatgctaa gctggcggcg ggggtcggtg tgggcatgga ggttgtgaga  1140
```

```
gatgaaaatg ggaagtataa gagagaagcg attgcagagg taataagaaa agtcgtgatg   1200
gagaaaaatg gggaggttat caggaggaaa gcaagggaat tgagtgagaa aatgaaagag   1260
acaggagagc aagagattgg tagggcagtg gaggagctag tacaaatttg taagatgaag   1320
aaagacgcac aatattaa                                                 1338

SEQ ID NO: 53           moltype = AA   length = 447
FEATURE                 Location/Qualifiers
source                  1..447
                        mol_type = protein
                        organism = Panax notoginseng
SEQUENCE: 53
MDIEKGRISI VMLPFLAHGH ISPFFELAKH LSKRNCNIFL CSTPINLSSI KNRVSDKDSS    60
ASIKLVELHL PSSPDLPPQY HTTNGLPSHL MVPLKNAFET VGPTFSEILK TLDPDLLIYD   120
FNPSWAPEIA LSHNIPAVYF LTSAAATSSV ALRALKNPGE KYPFPDFYDN SNITPEPPSA   180
DKMKLFHDFV ACFKRSCDII LIKSFRELEG KYIDLLSTLS KKTLVPVGPL VQDPLGHDED   240
PKTGHLINWL DKRAESTVVF VCFGSEYFPS NEELEEVAIG LEISMVNFIL AVRFLEGEKK   300
GVLPEGFVQR VGDRGLVVEG WAPQARILGH SSTGGFVSHC GWSSIMESVK FGVPVIAMAR   360
HLDQPLNAKL AAGVGVGMEV VRDENGKYKR EAIAEVIRKV VMEKNGEVIR RKARELSEKM   420
KETGEQEIGR AVEELVQICK MKKDAQY                                      447

SEQ ID NO: 54           moltype = DNA   length = 1344
FEATURE                 Location/Qualifiers
source                  1..1344
                        mol_type = other DNA
                        organism = Panax notoginseng
SEQUENCE: 54
atggatatcg agaaaggtag aatcagtata gttatgctac cattttttagc ccatggtcac    60
atatctccat tccttgagct agccaagcat ctctcaaaaa gaaattgcaa tatattcctc   120
tgttctaccc caatcaatct tagctccatc aagaacagag tatctgataa ggattcctct   180
gcttcaataa aactagtaga gcttcatctt ccatcttccc ctgatcttcc tcctcagtac   240
cacaccacaa atggcctccc ttcccatctc atggtcccac tcaaaaacgc ctttgaaaca   300
gtaggcccca ccttctctga aatccttaaa accttagacc ctgatttgct tatttatgat   360
ttcaatccct catgggcacc ggagatcgct ttgtctcaca atattccggc agtttatttc   420
ctaacctcgg cagcagccac ctcttccgtg gcccatcgtg ctttgaaaaa cccaggtgaa   480
aaatacccat ttccagattt ttatgataac agtaatatta ccctgaacc accttctgca   540
gataaaatga agctatttca tgattttgtt gcttgtttca aacgatcttg cgacattatt   600
ttgattaaga gttttagaga actagaaggg aaatatattg atttgcttc cactttatct   660
aagaaaactt tggttcctgt tggtccactc gttcaagatc ctttgggaca tgatgaagat   720
ccaaaaacag ggcatcttat aaactggctt gacaaaaggg ctgaatctac agtggtgttt   780
gtctgctttg gaagtgagta ttttccctcc aatgaggaat tggaagaagt agcaattggg   840
ctagagatta gcatggttaa tttcatattg gctgtgagat tcttgaagg agagaaaaaa   900
ggggttttac cagaggggtt tgttcaaagg gtaggagaca gaggattggt tgtggagggg   960
tgggctccac aggcaagaat tttaggacat tcaagcggtt tgt gagccattgt          1020
gggtggagtt ctattatgga gagtgtgaag tttggggttc cagtaattgc catggccagg   1080
catcttgatc agcctttgaa tgctaagctg gcggcggagg tcggtgtggg catggaggtt   1140
gtgagagatg aaaatgggaa gtataagaga gaagcgattg cagaggtaat aagaaaagtc   1200
gtgatggaga aaaatgggga ggttatcagg aggaaagcaa gggaattgag tgagaaaatg   1260
aaagagacag gagagcaaga gattggtagg gcagtggagg agctagtaca aatttgtaag   1320
atgaagaaag acgcacaata ttaa                                         1344

SEQ ID NO: 55           moltype = AA   length = 447
FEATURE                 Location/Qualifiers
source                  1..447
                        mol_type = protein
                        organism = Panax notoginseng
SEQUENCE: 55
MDIEKGRISI VMLPFLAHGH ISPFLELAKH LSKRNCNIFL CSTPINLSSI KNRVSDKDSS    60
ASIKLVELHL PSSPDLPPQY HTTNGLPSHL MVPLKNAFET VGPTFSEILK TLDPDLLIYD   120
FNPSWAPEIA LSHNIPAVYF LTSAAATSSV ALRALKNPGE KYPFPDFYDN SNITPEPPSA   180
DKMKLFHDFV ACFKRSCDII LIKSFRELEG KYIDLLSTLS KKTLVPVGPL VQDPLGHDED   240
PKTGHLINWL DKRAESTVVF VCFGSEYFPS NEELEEVAIG LEISMVNFIL AVRFLEGEKK   300
GVLPEGFVQR VGDRGLVVEG WAPQARILGH SSTGGFVSHC GWSSIMESVK FGVPVIAMAR   360
HLDQPLNAKL AAGVGVGMEV VRDENGKYKR EAIAEVIRKV VMEKNGEVIR RKARELSEKM   420
KETGEQEIGR AVEELVQICK MKKDAQY                                      447

SEQ ID NO: 56           moltype = DNA   length = 1344
FEATURE                 Location/Qualifiers
source                  1..1344
                        mol_type = other DNA
                        organism = Panax notoginseng
SEQUENCE: 56
atgtatatcg agaaaggtag aatcagtata gttatgctac cattttttagc ccatggtcac    60
atatctccat tctttgagct agccaagcat ctctcaaaaa gaaattgcaa tatattcctc   120
tgttctaccc caatcaatct tagctccatc aagaacagag tatctgataa ggattcctct   180
gcttcaataa aactagtaga gcttcatctt ccatcttccc ctgatcttcc tcctcagtac   240
cacaccacaa atggcctccc ttcccatctc atggtcccac tcaaaaacgc ctttgaaaca   300
gtaggcccca ccttctctga aatccttaaa accttagacc ctgatttgct tatttatgat   360
ttcaatccct catgggcacc ggagatcgct ttgtctcaca atattccggc agtttatttc   420
ctaacctcgg cagcagccac ctcttccgtg gcccatcgtg ctttgaaaaa cccaggtgaa   480
```

```
aaatacccat tccagattt tatgataac agtaatatta cccctgaacc accttctgca    540
gataaaatga agctatttca tgattttgtt gcttgtttca aacgatcctg cgacattatt    600
ttgattaaga gttttagaga actagaaggg aaatatattg atttgctttc cactttatct    660
aagaaaactt tggttcctgt tggtccactc gttcaagatc ctttgggaca tgatgaagat    720
ccaaaaacag gcatcttat aaactggctt gacaaaaggg ctgaatctac agtggtgttt    780
gtctgctttg gaagtgagta ttttcctcc aatgaggaat ggaagaagt agcaattggg    840
ctagagatta gcatggttaa tttcatattg gctgtgagat ttcttgaagg agagaaaaaa    900
ggggttttac cagaggggtt tgttcaagg gtaggagaca gaggattggt tgtggagggg    960
tgggctccac aggcaagaat tttaggacat tcaagcaccg gtgggtttgt gagccattgt   1020
gggtggagtt ctattatgga gagtgtgaag tttgggggttc cagtaattgc catggccagc   1080
catcttgatc agcctttgaa tgctaagctg cgggcggagg tcggtgtggg catggaggtt   1140
gtgagagatg aaaatgggaa gtataagaga aagcgattg cagaggtaat aagaaaagtc   1200
gtgatggaga aaaatgggga ggttatcagg aggaaagcaa gggaattgag tgagaaaatg   1260
aaagagacag agagcaaga gattggtagg gcagtggagg agctagtaca aatttgtaag   1320
atgaagaaag acgcacaata ttaa                                          1344

SEQ ID NO: 57              moltype = AA   length = 447
FEATURE                    Location/Qualifiers
source                     1..447
                           mol_type = protein
                           organism = Panax notoginseng
SEQUENCE: 57
MYIEKGRISI VMLPFLAHGH ISPFFELAKH LSKRNCNIFL CSTPINLSSI KNRVSDKDSS    60
ASIKLVELHL PSSPDLPPQY HTTNGLPSHL MVPLKNAFET VGPTFSEILK TLDPDLLIYD   120
FNPSWAPEIA LSHNIPAVYF LTSAAATSSV ALRALKNPGE KYPFPDFYDN SNITPEPPSA   180
DKMKLFHDFV ACFKRSCDII LIKSFRELEG KYIDLLSTLS KKTLVPVGPL VQDPLGHDED   240
PKTGHLINWL DKRAESTVVF VCFGSEYFPS NEELEEVAIG LEISMVNFIL AVRFLEGEKK   300
GVLPEGFVQR VGDRGLVVEG WAPQARILGH SSTGGFVSHC GWSSIMESVK FGVPVIAMAR   360
HLDQPLNAKL AAEVGVGMEV VRDENGKYKR EAIAEVIRKV VMEKNGEVIR RKARELSEKM   420
KETGEQEIGR AVEELVQICK MKKDAQY                                       447

SEQ ID NO: 58              moltype = DNA   length = 1344
FEATURE                    Location/Qualifiers
source                     1..1344
                           mol_type = other DNA
                           organism = Panax notoginseng
SEQUENCE: 58
atggatatcg aaaaggtag aatcagtata gttatgctgc catttttagc ccatggtcac     60
atatctccat tctttgagct agccaagcat ctctcaaaaa gaaattgcaa tatattcctc   120
tgttctaccc caatcaatct tagctccatc aagaacagag tatctgataa ggattcctct   180
gcttctataa aactagtaga gcttcatctt ccatcttccc ctgatcttcc tcctcagtac   240
cacaccacaa atggcctccc ttcccatctc atggtcccca tcaaaaacgc ctttgaaaca   300
gtaggccca ccttctctga aatccttaaa acctagacc tcgattttgct tatttatgat    360
ttcaatccct catgggcacc ggagatcgct ttgtctcaca atattccggc agtttatttc   420
ctaacctcgg cagcagccac ctcttccgtg gccctacgtg ctttgaaaaa cccaggtgaa   480
aaatacccat tccagattt tatgataac agtaatatta cccctgaacc accttctgca    540
gataaaatga agctatttca tgattttgtt gcttgtttca aacgatcctg cgacattatt    600
ttgattaaga gttttagaga actagaaggg aaatatattg atttgctttc cactttatct    660
aagaaaactt tggttcctgt tggtccactc gttcaagatc atttgggaca tgatgaagat    720
ccaaaaacag gcatcttat aaactggctt gacaaaaggg ctgaatctac agtggtgttt    780
gtctgctttg gaagtgagta ttttcctcc aatgaggaat ggaagaagt agcaattggg    840
ctagagatta gcatggttaa tttcatattg gctgttagat ttcttgaagg agagaaaaaa    900
ggggttttac cagaagggtt tgttcaagg gtaggagaca gaggattggt tgtggagggg    960
tgggctccac aggcaagaat tttaggacat tcaagcaccg gtgggtttgt gagccattgt   1020
gggtggagtt ctattatgga gagtgtgaag tttgggggttc cagtaattgc catggccagc   1080
catcttgatc agcctttgaa tgctaagctg cgggcggagg ttggtgtggg catggaggtt   1140
gtgagagatg aaaatgggaa gtatacgaga aagcgattg cagaggtaat aagaaaagtt   1200
gtgatggaga aaaatgggga ggttatcagg aggaaagcaa gggaattgag tgataaaatg   1260
aaagagaaag gagagcaaga gattggtagg gcagtggagg agctagtaca aatttgtaag   1320
atgaagaaag acgcacaata ttaa                                          1344

SEQ ID NO: 59              moltype = AA   length = 447
FEATURE                    Location/Qualifiers
source                     1..447
                           mol_type = protein
                           organism = Panax notoginseng
SEQUENCE: 59
MDIEKGRISI VMLPFLAHGH ISPFFELAKH LSKRNCNIFL CSTPINLSSI KNRVSDKDSS    60
ASIKLVELHL PSSPDLPPQY HTTNGLPSHL MVPLKNAFET VGPTFSEILK TLDPDLLIYD   120
FNPSWAPEIA LSHNIPAVYF LTSAAATSSV ALRALKNPGE KYPFPDFYDN SNITPEPPSA   180
DKMKLFHDFV ACFKRSCDII LIKSFRELEG KYIDLLSTLS KKTLVPVGPL VQDHLGHDED   240
PKTGHLINWL DKRAESTVVF VCFGSEYFPS NEELEEVAIG LEISMVNFIL AVRFLEGEKK   300
GVLPEGFVQR VGDRGLVVEG WAPQARILGH SSTGGFVSHC GWSSIMESVK FGVPVIAMAR   360
HLDQPLNAKL AAEVGVGMEV VRDENGKYTR EAIAEVIRKV VMEKNGEVIR RKARELSDKM   420
KEKGEQEIGR AVEELVQICK MKKDAQY                                       447

SEQ ID NO: 60              moltype = DNA   length = 41
FEATURE                    Location/Qualifiers
misc_feature               1..41
```

```
                          note = primer
source                    1..41
                          mol_type = other DNA
                          organism = synthetic construct
SEQUENCE: 60
taagaaggag ataccatg gatatcgaaa aaggtagaat c                         41

SEQ ID NO: 61             moltype = DNA  length = 44
FEATURE                   Location/Qualifiers
misc_feature              1..44
                          note = primer
source                    1..44
                          mol_type = other DNA
                          organism = synthetic construct
SEQUENCE: 61
tgcggccgca agcttgtcga catattgtgc gtctttcttc atct                    44

SEQ ID NO: 62             moltype = DNA  length = 46
FEATURE                   Location/Qualifiers
misc_feature              1..46
                          note = primer
source                    1..46
                          mol_type = other DNA
                          organism = synthetic construct
SEQUENCE: 62
taagaaggag atataccatg ggtgataacc aaaaaggtag aatcag                  46

SEQ ID NO: 63             moltype = DNA  length = 44
FEATURE                   Location/Qualifiers
misc_feature              1..44
                          note = primer
source                    1..44
                          mol_type = other DNA
                          organism = synthetic construct
SEQUENCE: 63
tgcggccgca agcttgtcga cttgtgcatc tttcttcttc ttac                    44

SEQ ID NO: 64             moltype = DNA  length = 45
FEATURE                   Location/Qualifiers
misc_feature              1..45
                          note = primer
source                    1..45
                          mol_type = other DNA
                          organism = synthetic construct
SEQUENCE: 64
taagaaggag atataccatg ggtgatatcg agaaaggtag aatca                   45

SEQ ID NO: 65             moltype = DNA  length = 41
FEATURE                   Location/Qualifiers
misc_feature              1..41
                          note = primer
source                    1..41
                          mol_type = other DNA
                          organism = synthetic construct
SEQUENCE: 65
tgcggccgca agcttgtcga catattgtgc gtctttcttc a                       41

SEQ ID NO: 66             moltype = DNA  length = 45
FEATURE                   Location/Qualifiers
misc_feature              1..45
                          note = primer
source                    1..45
                          mol_type = other DNA
                          organism = synthetic construct
SEQUENCE: 66
taagaaggag atataccatg ggtgatatcg aaaaaggtag aatca                   45

SEQ ID NO: 67             moltype = DNA  length = 41
FEATURE                   Location/Qualifiers
misc_feature              1..41
                          note = primer
source                    1..41
                          mol_type = other DNA
                          organism = synthetic construct
SEQUENCE: 67
tgcggccgca agcttgtcga catattgtgc gtctttcttc a                       41

SEQ ID NO: 68             moltype = DNA  length = 45
FEATURE                   Location/Qualifiers
```

```
misc_feature            1..45
                        note = primer
source                  1..45
                        mol_type = other DNA
                        organism = synthetic construct
SEQUENCE: 68
taagaaggag atataccatg ggtgatatcg aaaaaggtag aatca              45

SEQ ID NO: 69           moltype = DNA   length = 42
FEATURE                 Location/Qualifiers
misc_feature            1..42
                        note = primer
source                  1..42
                        mol_type = other DNA
                        organism = synthetic construct
SEQUENCE: 69
tgcggccgca agcttgtcga catattgtgc gtctttcatc at                 42

SEQ ID NO: 70           moltype = DNA   length = 47
FEATURE                 Location/Qualifiers
misc_feature            1..47
                        note = primer
source                  1..47
                        mol_type = other DNA
                        organism = synthetic construct
SEQUENCE: 70
taagaaggag atataccatg ggtgatatcg aaaaaggtag aatcagt            47

SEQ ID NO: 71           moltype = DNA   length = 44
FEATURE                 Location/Qualifiers
misc_feature            1..44
                        note = primer
source                  1..44
                        mol_type = other DNA
                        organism = synthetic construct
SEQUENCE: 71
gtgcggccgc aagcttgtcg acatattgtg cgtctttctt catc               44

SEQ ID NO: 72           moltype = DNA   length = 46
FEATURE                 Location/Qualifiers
misc_feature            1..46
                        note = primer
source                  1..46
                        mol_type = other DNA
                        organism = synthetic construct
SEQUENCE: 72
taagaaggag atataccatg ggtgatatcg aaaaaggtag aatcag             46

SEQ ID NO: 73           moltype = DNA   length = 43
FEATURE                 Location/Qualifiers
misc_feature            1..43
                        note = primer
source                  1..43
                        mol_type = other DNA
                        organism = synthetic construct
SEQUENCE: 73
gtgcggccgc aagcttgtcg acatattgtg cgtctttctt cat                43

SEQ ID NO: 74           moltype = DNA   length = 44
FEATURE                 Location/Qualifiers
misc_feature            1..44
                        note = primer
source                  1..44
                        mol_type = other DNA
                        organism = synthetic construct
SEQUENCE: 74
taagaaggag atataccatg ggtgatatcg agaaaggtag aatc               44

SEQ ID NO: 75           moltype = DNA   length = 42
FEATURE                 Location/Qualifiers
misc_feature            1..42
                        note = primer
source                  1..42
                        mol_type = other DNA
                        organism = synthetic construct
SEQUENCE: 75
gtgcggccgc aagcttgtcg acatattgtg cgtctttctt ca                 42

SEQ ID NO: 76           moltype = DNA   length = 44
```

```
FEATURE                 Location/Qualifiers
misc_feature            1..44
                        note = primer
source                  1..44
                        mol_type = other DNA
                        organism = synthetic construct
SEQUENCE: 76
taagaaggag atataccatg ggtgatatcg agaaaggtag aatc              44

SEQ ID NO: 77           moltype = DNA   length = 42
FEATURE                 Location/Qualifiers
misc_feature            1..42
                        note = primer
source                  1..42
                        mol_type = other DNA
                        organism = synthetic construct
SEQUENCE: 77
gtgcggccgc aagcttgtcg acatattgtg cgtctttctt ca                42

SEQ ID NO: 78           moltype = DNA   length = 38
FEATURE                 Location/Qualifiers
misc_feature            1..38
                        note = primer
source                  1..38
                        mol_type = other DNA
                        organism = synthetic construct
SEQUENCE: 78
taagaaggag atataccatg tatatcgaga aaggtaga                     38

SEQ ID NO: 79           moltype = DNA   length = 41
FEATURE                 Location/Qualifiers
misc_feature            1..41
                        note = primer
source                  1..41
                        mol_type = other DNA
                        organism = synthetic construct
SEQUENCE: 79
tgcggccgca agcttgtcga catattgtgc gtctttcttc a                 41

SEQ ID NO: 80           moltype = DNA   length = 40
FEATURE                 Location/Qualifiers
misc_feature            1..40
                        note = primer
source                  1..40
                        mol_type = other DNA
                        organism = synthetic construct
SEQUENCE: 80
taagaaggag atataccatg gatatcgaaa aaggtagaat                   40

SEQ ID NO: 81           moltype = DNA   length = 45
FEATURE                 Location/Qualifiers
misc_feature            1..45
                        note = primer
source                  1..45
                        mol_type = other DNA
                        organism = synthetic construct
SEQUENCE: 81
tgcggccgca agcttgtcga catattgtgc gtctttcttc atctt             45

SEQ ID NO: 82           moltype = DNA   length = 22
FEATURE                 Location/Qualifiers
misc_feature            1..22
                        note = primer
source                  1..22
                        mol_type = other DNA
                        organism = synthetic construct
SEQUENCE: 82
agagttcatt catggataac ca                                      22

SEQ ID NO: 83           moltype = DNA   length = 22
FEATURE                 Location/Qualifiers
misc_feature            1..22
                        note = primer
source                  1..22
                        mol_type = other DNA
                        organism = synthetic construct
SEQUENCE: 83
ttaagcgcat tcaaaaatat tc                                      22
```

| SEQ ID NO: 84 | moltype = DNA length = 21 |
| --- | --- |
| FEATURE | Location/Qualifiers |
| misc_feature | 1..21 |
| | note = primer |
| source | 1..21 |
| | mol_type = other DNA |
| | organism = synthetic construct |

SEQUENCE: 84
agagttcatc atggatatcg a                                              21

| SEQ ID NO: 85 | moltype = DNA length = 22 |
| --- | --- |
| FEATURE | Location/Qualifiers |
| misc_feature | 1..22 |
| | note = primer |
| source | 1..22 |
| | mol_type = other DNA |
| | organism = synthetic construct |

SEQUENCE: 85
catagctcat tcaaaatgac tc                                             22

| SEQ ID NO: 86 | moltype = DNA length = 21 |
| --- | --- |
| FEATURE | Location/Qualifiers |
| misc_feature | 1..21 |
| | note = primer |
| source | 1..21 |
| | mol_type = other DNA |
| | organism = synthetic construct |

SEQUENCE: 86
catagctcat tcaaaatgaa t                                              21

| SEQ ID NO: 87 | moltype = DNA length = 34 |
| --- | --- |
| FEATURE | Location/Qualifiers |
| misc_feature | 1..34 |
| | note = primer |
| source | 1..34 |
| | mol_type = other DNA |
| | organism = synthetic construct |

SEQUENCE: 87
tatctatcgt atacgccaga gttcatcatg gata                                34

| SEQ ID NO: 88 | moltype = DNA length = 35 |
| --- | --- |
| FEATURE | Location/Qualifiers |
| misc_feature | 1..35 |
| | note = primer |
| source | 1..35 |
| | mol_type = other DNA |
| | organism = synthetic construct |

SEQUENCE: 88
tgcagtcgag atacatctag catacaaaga aagag                               35

| SEQ ID NO: 89 | moltype = DNA length = 1329 |
| --- | --- |
| FEATURE | Location/Qualifiers |
| source | 1..1329 |
| | mol_type = other DNA |
| | organism = Panax ginseng |

SEQUENCE: 89
```
atggataacc aaaaaggtag aatcagtata gcgttgctac catttttagc ccatggtcac    60
atatctccct tctttgagct agccaaacaa ctcgcgaaaa gaaattgcaa tgttttcctc   120
tgttctaccc caatcaatct tagctccatc aaggataagg attcctctgc ttctataaaa   180
ctagttgagc ttcatcttcc atcttcccct gatcttcctc ctcactatca caccacaaat   240
ggcctccctt cccatctcat gctcccactc agaaacgcct ttgaaactgc aggccccacc   300
ttctctgaaa tccttaaaac cttaaacccc gatttgctta tttatgattt caatccctca   360
tgggcaccgg agatcgcttc gtctcacaat attccgcag ttatttcct aaccacggca    420
gcagccagct cttccattgg cctacatgct ttcaaaaacc caggtgaaaa atacccattt   480
ccagattttt atgataacag taatattacc cctgaaccac ttctgcaga taacatgaag   540
ctacttcatg attttatcgc ttgtttcgaa cgatcttgcg acattatttt gattaagagt   600
tttagagaac tagaagggaa atatattgat ttgctttcca ctttatctga taaaactttg   660
gttcctgttg gtccactcgt tcaagatcct atgggccata atgaagatcc aaaaacagag   720
cagattataa actggcttga caaaagggct gaatcatcag tggtgtttgt ctgctttgga   780
agtgagtatt ttctctccaa tgaggaattg gaagaagtag caattgggct agagattagc   840
atggttaatt tcatatggc tgtgagatta ttgaaggag agaaaaaagg ggttttacca    900
gagggatttg ttcaaagggt aggagacaga ggattggttg tggaggggtg gctccacag    960
gcaagaattt taggacattc aagcaccggt gggtttgtga gccattgtgg gtggagttct  1020
attgcggaga gtatgaagtt tggggttcca gtaattgcca ggccaggca tcttgatcag  1080
cctttgaatg gtaagctggc ggcggaggtt ggtgtgggca tggaggttgt gagagatgaa  1140
aatgggaagt ataagagaga agggattgca gaggtaataa gaaagtcgt tgtgagaaa   1200
agtggggagg ttatgaggag gaaagcaagg gaattgagtg agaaaatgaa agagaaagga  1260
gaggaagaga ttgatagggc agtggaggag ctagtacaaa tttgtaagaa gaagaaagat  1320
gcacaatag                                                          1329
```

```
SEQ ID NO: 90           moltype = AA   length = 442
FEATURE                 Location/Qualifiers
source                  1..442
                        mol_type = protein
                        organism = Panax ginseng
SEQUENCE: 90
MDNQKGRISI ALLPFLAHGH ISPFFELAKQ LAKRNCNVFL CSTPINLSSI KDKDSSASIK    60
LVELHLPSSP DLPPHYHTTN GLPSHLMLPL RNAFETAGPT FSEILKTLNP DLLIYDFNPS   120
WAPEIASSHN IPAVYFLTTA AASSSIGLHA FKNPGEKYPF PDFYDNSNIT PEPPSADNMK   180
LLHDFIACFE RSCDIILIKS FRELEGKYID LLSTLSDKTL VPVGPLVQDP MGHNEDPKTE   240
QIINWLDKRA ESTVVFVCFG SEYFLSNEEL EEVAIGLEIS MVNFIWAVRL IEGEKKGVLP   300
EGFVQRVGDR GLVVEGWAPQ ARILGHSSTG GFVSHCGWSS IAESMKFGVP VIAMARHLDQ   360
PLNGKLAAEV GVGMEVVRDE NGKYKREGIA EVIRKVVVEK SGEVMRRKAR ELSEKMKEKG   420
EEEIDRAVEE LVQICKKKKD AQ                                           442

SEQ ID NO: 91           moltype = DNA   length = 1329
FEATURE                 Location/Qualifiers
source                  1..1329
                        mol_type = other DNA
                        organism = Panax ginseng
SEQUENCE: 91
atggataacc aagaaggtag aatcagtata gcgttgctac cattttttagc ccatggtcac    60
atatctccct tctttgagct agccaaacaa ctcgcaaaaa gaaattgcaa tgttttcctc   120
tgttctaccc caatcaatct tagctccatc aagaataagg attcctctgc ttctataaaa   180
ctagttgagc ttcatcttcc atcttcccct gatcttcctc ctcactatca caccacaaat   240
ggcctccctt cccatctcat ggtcccactc ataaacgcct tgaaacagc aggcccacc    300
ttctctgaaa tccttaaaac cttaaacccc gatttgctta tttatgattt caatccctca   360
tgggcaccgg agatcgcttc gtctcacaat attccggcag tttatttcct aaccacggca   420
gcagccagct cttccattgg cctacatgct ttcaaaaacc caggtgaaaa atacccattt   480
ccagatttt atgataacag taatattacc cctgaaccac cttctgcaga taacatgaag    540
ctacttcatg attttatcgc ttgtttcgaa cgatcttgcg acattatttt gattaagagt   600
tttagagaac tagaagggaa atatattgat ttgctttcca ctttatctga taaactttg    660
gttcctgttg gtccactcgt tcaagatcct atgggccata tgaagatcc aaaaacagag   720
cagattataa actggcttga caaaaggggc gaatctacag tggtgtttgt ctgctttgga   780
agtgagtatt ttctctccaa tgaggaattg gaagaagtag caattgggct agagattagc   840
acggttaatt tcatatgggc tgtgagatta attgaaggag agaaaaaagg gattttacca   900
gaggggtttg ttcaaagggt aggagacaga ggattggttg tggaggggtg gctccacag   960
gcaagaattt taggacattc aagcaccggt ggtttgtga gccattgtgg gtggagttct  1020
attgcggaga gtatgaagtt tggggttcca gtaattgcca tggccaggca tcttgatcag  1080
cctttgaatg gtaagctggc ggcggaggtt ggtgtgggca tggaggttgt gagagatgag  1140
aatgggaagt ataagagaga agggattgca gaggtaataa gaaaagtggt tgtggagaaa  1200
agtggggagg ttatcaggag gaaagcaagg gagttgagtg agaaaatgaa agagaaagga  1260
gagcaagaa ttgataggc attggaggag ctagtacaaa tttgtaagaa gaagaaagat  1320
gaacaatag                                                         1329

SEQ ID NO: 92           moltype = AA   length = 442
FEATURE                 Location/Qualifiers
source                  1..442
                        mol_type = protein
                        organism = Panax ginseng
SEQUENCE: 92
MDNQEGRISI ALLPFLAHGH ISPFFELAKQ LAKRNCNVFL CSTPINLSSI KNKDSSASIK    60
LVELHLPSSP DLPPHYHTTN GLPSHLMVPL INAFETAGPT FSEILKTLNP DLLIYDFNPS   120
WAPEIASSHN IPAVYFLTTA AASSSIGLHA FKNPGEKYPF PDFYDNSNIT PEPPSADNMK   180
LLHDFIACFE RSCDIILIKS FRELEGKYID LLSTLSDKTL VPVGPLVQDP MGHNEDPKTE   240
QIINWLDKRA ESTVVFVCFG SEYFLSNEEL EEVAIGLEIS TVNFIWAVRL IEGEKKGILP   300
EGFVQRVGDR GLVVEGWAPQ ARILGHSSTG GFVSHCGWSS IAESMKFGVP VIAMARHLDQ   360
PLNGKLAAEV GVGMEVVRDE NGKYKREGIA EVIRKVVVEK SGEVIRRKAR ELSEKMKEKG   420
EQEIDRALEE LVQICKKKKD EQ                                           442

SEQ ID NO: 93           moltype = DNA   length = 1332
FEATURE                 Location/Qualifiers
source                  1..1332
                        mol_type = other DNA
                        organism = Panax ginseng
SEQUENCE: 93
atggataacc aagaaggtag aatcagtata gcgttgctac cattttttagc ccatggtcac    60
atatctccct tctttgagct agccaaacaa ctcgcaaaaa gaaattgcaa tgttttcctc   120
tgttctaccc caatcaatct tagctccatc aagaataagg attcctctgc ttctataaaa   180
ctagttgagc ttcatcttcc atcttcccct gatcttcctc ctcactatca caccacaaat   240
ggcctccctt cccatctcat ggtcccactc ataaacgcct tgaaacagc aggcccacc    300
ttctctgaaa tccttaaaac cttaaacccc gatttgctta tttatgattt caatccctca   360
tgggcaccgg agatcgcttc gtctcacaat attccggcag tttatttcct aaccacggca   420
gcagccagct cttccattgg cctacatgct ttcaaaaacc caggtgaaaa atacccattt   480
ccagatttt atgataacag taatattacc cctgaaccac cttctgcaga taacatgaag    540
ctacttcatg attttatcgc ttgtttcgaa cgatcttgcg acattatttt gattaagagt   600
tttagagaac tagaagggaa atatatcgat ttgctttcca ctttatctga taaactttg    660
gttcctgttg gtccactcgt tcaagatcct atgggccata tgaagatcc aaaaacagag   720
```

```
cagattataa actggcttga caaaagggct gaatctacag tggtgtttgt ctgctttgga    780
agtgagtatt ttctctccaa tgaggaattg gaagaagtag caattgggct agagattagc    840
atggttaatt tcatatgggc tgtgagatta attgaaggag agaaaaaagg ggttttacca    900
gagggatttg ttcaaagggt aggagacaga ggattggttg tggaggggtg ggctccacag    960
gcaagaattt taggacattc aagcaccggt gggtttgtga gccattgtgg gtggagttct   1020
attatggaga gtgtgaagtt tgggggttcca gtaattgcca tggccaggca tcttgatcag   1080
cctttgaatg ctaagctggc ggcggaggtt ggtgtgggca tggaggttat gagagatgaa   1140
aatgggaagt ataagagaga agcgattgca gaggtaataa aaaagtcgt gatggagaaa    1200
aatggggagg ttatgaggag gaaagcaagg gaattgagtg agaaaatgaa agtgaaagga   1260
gagcaagaga ttggtagggc ggtggaggag ctagtacaaa tttgtaagaa gaagaagcag   1320
cacgcacaat at                                                       1332

SEQ ID NO: 94           moltype = AA   length = 444
FEATURE                 Location/Qualifiers
source                  1..444
                        mol_type = protein
                        organism = Panax ginseng
SEQUENCE: 94
MDNQEGRISI ALLPFLAHGH ISPFFELAKQ LAKRNCNVFL CSTPINLSSI KNKDSSASIK     60
LVELHLSSSP DLPPHYHTTN GLPSHLMVPL INAFETAGPT FSEILKTLNP DLLIYDFNPS    120
WAPEIASSHN IPAVYFLTTA AASSSIGLHA FKNPGEKYPF PDFYDNSNNT PEPPSADNMK    180
LLHDFIACFE RSCDIILIKS FIELEGKYID LLSTLSDKTL VPVGPLVQDP MGHNEDPKTE    240
QIINWLDKRA ESTVVFVCFG SEYFLSNEEL EEVAIGLEIS MVNFIWAVRL IEGEKKGVLP    300
EGFVQRVGDR GLVVEGWAPQ ARILGHSSTG GFVSHCGWSS IMESVKFGVP VIAMARHLDQ    360
PLNAKLAAEV GVGMEVMRDE NGKYKREAIA EVIRKVVMEK NGEVMRRKAR ELSEKMKVKG    420
EQEIGRAVEE LVQICKKKKQ HAQY                                          444

SEQ ID NO: 95           moltype = DNA   length = 1329
FEATURE                 Location/Qualifiers
source                  1..1329
                        mol_type = other DNA
                        organism = Panax ginseng
SEQUENCE: 95
atggataacc aaaaaggtag aatcagtata gcgttgctac catttttagc ccatggtcac     60
atatctccct tctttgagct agccaaacaa ctcgcgaaaa gaaattgcaa tgttttcctc    120
tgttctaccc caatcaatct tagctccatc aaggataagg attcctctgc ttctataaaa    180
ctagttgagc ttcatcttcc atcttcccct gatcttcctc ctcactatca caccacaaat    240
ggcctcccctt cccatctcat gctcccactc agaaacgcct tgaaactgc aggccccacc    300
ttctctgaaa tccttaaaac cttaaacccc gatttgctta tttatgattt caatccctca    360
tgggcaccgg agatcgcttc gtctcacaat attccggcag tttatttcct aaccacggca    420
gcagccagct cttccattgg cctacatgct ttcaaaaacc caggtgaaaa atacccattt    480
ccagattttt atgataacag taatattacc cctgaaccac cttctgcaga taacatgaag    540
ctacttcatg attttatcgc ttgtttcgaa cgatcttgcg acattattt gattaagagt    600
tttagagaac tagaagggaa atatattgat ttgctttcca ctttatctga taaaactttg    660
gttcctgttg gtccactcgt tcaagatcct atgggccata tgaagatcc aaaaacagag    720
cagattataa actggcttga caaatggct gaatctacag tggtgtttgt ctgctttgga    780
agtgagtatt ttctctccaa tgaggaattg gaagaagtag caattgggct agagattagc    840
acggttaatt tcatatgggc tgtgagatta attgaaggag agaaaaaagg gattttacca    900
gaggggtttg ttcaaagggt aggagacaga ggattggttg tggaggggtg ggctccacag    960
gcaagaattt taggacattc aagcaccggt gggtttgtga gccattgtgg gtggagttct   1020
attgcggaga gtatgaagtt tgggggttcca gtaattgcca tggccaggca tcttgatcag   1080
cctttgaatg gtaagctggc ggcggaggtt ggtgtgggca tggaggttgt gagagatgag   1140
aatgggaagt ataagagaga agggattgca gaggtaataa aaaagtggt gtgagaaaa    1200
agtggggagg ttatcaggag gaaagcaagg gagttgagtg agaaaatgaa agagaaagga   1260
gagcaagaga ttgatagggc attggaggag ctagtacaaa tttgtaagaa gaagaaagat   1320
gaacaatag                                                          1329

SEQ ID NO: 96           moltype = AA   length = 442
FEATURE                 Location/Qualifiers
source                  1..442
                        mol_type = protein
                        organism = Panax ginseng
SEQUENCE: 96
MDNQKGRISI ALLPFLAHGH ISPFFELAKQ LAKRNCNVFL CSTPINLSSI KDKDSSASIK     60
LVELHLSSSP DLPPHYHTTN GLPSHLMLPL RNAFETAGPT FSEILKTLNP DLLIYDFNPS    120
WAPEIASSHN IPAVYFLTTA AASSSIGLHA FKNPGEKYPF PDFYDNSNIT PEPPSADNMK    180
LLHDFIACFE RSCDIILIKS FRELEGKYID LLSTLSDKTL VPVGPLVQDP MGHNEDPKTE    240
QIINWLDKMA ESTVVFVCFG SEYFLSNEEL EEVAIGLEIS TVNFIWAVRL IEGEKKGILP    300
EGFVQRVGDR GLVVEGWAPQ ARILGHSSTG GFVSHCGWSS IAESMKFGVP VIAMARHLDQ    360
PLNGKLAAEV GVGMEVVRDE NGKYKREGIA EVIRKVVVEK SGEVIRRKAR ELSEKMKEKG    420
EQEIDRALEE LVQICKKKKD EQ                                            442

SEQ ID NO: 97           moltype = DNA   length = 1347
FEATURE                 Location/Qualifiers
source                  1..1347
                        mol_type = other DNA
                        organism = Panax ginseng
SEQUENCE: 97
atggatatcg aaaaaggtag aatcagtata gttatgctgc catttttagc ccatggccac     60
```

```
atttctccat tctttgagct agccaagcat ctctcaaaaa gaaattgtaa tatattcctc    120
tgttctaccc caatcaatct tagctccatc aagaacagag tatctgataa ggattcctct    180
gcttctataa aactagtaga gcttcatctt ccctcttccc ctgatcttcc ccctcactac    240
cacaccacaa atggcctccc ttcccatctc atggtcccac tcagaaacgc ctttgaaaca    300
gcagccccca ccttctctga aatccttaaa accttaaacc ctgatttgct tatttatgat    360
ttcaatccct catgggcacc ggaaatcgct tcgtctcaca atattccggc agtttatttc    420
ctaacctcgg cagcagccac ctcttccatg ggcctacatg ctttcaaaaa ctcaggtgaa    480
aaatacccat ttccagattt ttatgataac agtaatatta cccctgaacc accttctgca    540
gataaaatga agctatttca tgattttgtc gcttgtttca aacgatcttg cgacattatt    600
ttgattaaga gttttagaga actgaagggg aaatatattg attttcttc cactttatct    660
aagaaaactt tggttcctgt tggtccactc gttcaagatc ctatgggaca tgatgaagat    720
ccaaaaacag ggcatcttat aaactggctt gacaagaggg ctgaatctac agtggtgttt    780
gtctgctttg gaagtgagta ttttccctcc aatgaggaat tggaagaatt agcaattggg    840
ctagagatta gcatggttag tttcatattg gctgtgaagt tcctgaagg agagaaaaa    900
gggattttac cagaggggtt tgttcaaagg gtaggagaca gaggattggt tgtggagggg    960
tgggctccac aggcaagaat tttaggacat tcaagcaccg gtgggtttgt gagccattgt   1020
gggtggagtt ctattatgga gagtgtgaag tttggggttc cagtaattgc catggccagg   1080
catcttgatc agcctttgaa tgctaagctg gcggcggagg ttggtgtggg catggaggtt   1140
atgagagatg aaaatgggaa gtataagaga gaagcgattg cagaggtaat aagaaaagtc   1200
gtgatggaga aaaatgggga ggttatgagg aggaaagcaa gggaattgag tgagaaaatg   1260
aaagtgaaag agagcaagaa gattggtagg gcggtggagg agctagtaca aatttgtaag   1320
aagaagaagc agcacgcaca atattaa                                       1347

SEQ ID NO: 98          moltype = AA  length = 448
FEATURE                Location/Qualifiers
source                 1..448
                       mol_type = protein
                       organism = Panax ginseng
SEQUENCE: 98
MDIEKGRISI VMLPFLAHGH ISPFFELAKH LSKRNCNIFL CSTPINLSSI KNRVSDKDSS     60
ASIKLVELHL PSSPDLPPHY HTTNGLPSHL MVPLRNAFET AAPTFSEILK TLNPDLLIYD    120
FNPSWAPEIA SSHNIPAVYF LTSAAATSSM GLHAFKNSGE KYPFPDFYDN SNITPEPPSA    180
DKMKLFHDFV ACFKRSCDII LIKSFRELEG KYIDFLSTLS KKTLVPVGPL VQDPMGHDED    240
PKTGHLINWL DKRAESTVVF VCFGSEYFPS NEELEELAIG LEISMVSFIL AVRFPEGEKK    300
GILPEGFVQR VGDRGLVVEG WAPQARILGH SSTGGFVSHC GWSSIMESVK FGVPVIAMAR    360
HLDQPLNAKL AAEVGVGMEV MRDENGKYKR EAIAEVIRKV VMEKNGEVMR RKARELSEKM    420
KVKGEQEIGR AVEELVQICK KKKQHAQY                                      448

SEQ ID NO: 99          moltype = DNA  length = 1329
FEATURE                Location/Qualifiers
source                 1..1329
                       mol_type = other DNA
                       organism = Panax ginseng
SEQUENCE: 99
atggataacc aagaaggtag aatcagtata gcgttgctac catttttagc ccatggtcac     60
atatctccct tctttgagct agccaaacaa ctcgcaaaaa gaaattgcaa tgttttcctc    120
tgttctaccc caatcaatct tagctccatc aagaataagg attcctctgc ttctataaaa    180
ctagttgagc ttcatcttcc atcttcccct gatcttcctc tcactatca caccacaaat    240
ggcctccctt cccatctcat ggtcccactc ataaacgcct tgaaacagc aggccccacc    300
ttctctgaaa tccttaaaac cttaaacccc gatttgctta tttatgattt caatccctca    360
tgggcaccgg agatcgcttc gtctcacaat attccggca tttatttcct aaccacgca    420
gcagccagct cttccattgg cctacatgct ttcaaaaacc caggtgaaaa atacccattt    480
ccagattttt atgataacag taataatacc cctgaaccac cttctgcaga taacatgaag    540
ctacttcatg attttatcgc ttgtttcgaa cgatcttgcg acattatttt gattaagagt    600
tttatagaac tagaagggaa atatatcgat ttgctttca cttatctgaa aaacttttg    660
gttcctgttg gtccactcgt tcaagatcct atgggccata tgaagatcc aaaaacagag    720
cagattataa actggcttga caaagggct gaatctacag tggtgtttgt ctactttgga    780
agtgagtatt ttctctccaa tgaggaattg aagaagtag caattgggct agagattagc    840
atggttaatt tcatatgggc tgtgagatta attgaaggag agaaaaaggg tgttttacca    900
gaggggtttg ttcaaagggt aggagacaga ggattggttg tggggggtc ggctccacag    960
gcaagaattt taggacattc aagcaccggt gggtttgtga gccattgtgg gtggagttct   1020
attgcggaga gtgaagtt tggggttcca gtaattgcca tggccaggca tcttgatcag   1080
cctttgaatg gtaagctggc ggcggaggtt ggtgtgggca tggaggttgt gagagatgaa   1140
aatgggaaga taagagaga agggattgca gaggtaataa gaaaagtc tgtgggggg    1200
agtggggagg ttatgaggag gaaagcaagg gaattgagtg agaaaatgaa agagaagga   1260
gaggaagaga ttgatagggc agtggaggag ctagtacaaa tttgtaagaa gaagaaagat   1320
gcacaatag                                                          1329

SEQ ID NO: 100         moltype = AA  length = 442
FEATURE                Location/Qualifiers
REGION                 1..442
                       note = primer
source                 1..442
                       mol_type = protein
                       organism = synthetic construct
SEQUENCE: 100
MDNQEGRISI ALLPFLAHGH ISPFFELAKQ LAKRNCNVFL CSTPINLSSI KNKDSSASIK     60
LVELHLPSSP DLPPHYHTTN GLPSHLMVPL INAFETAGPT FSEILKTLNP DLLIYDFNPS    120
WAPEIASSHN IPAVYFLTTA AASSSIGLHA FKNPGEKYPF PDFYDNSNNT PEPPSADNMK    180
```

```
LLHDFIACFE RSCDIILIKS FIELEGKYID LLSTLSDKTL VPVGPLVQDP MGHNEDPKTE    240
QIINWLDKRA ESTVVFVYFG SEYFLSNEEL EEVAIGLEIS MVNFIWAVRL IEGEKKGVLP    300
EGFVQRVGDR GLVVEGWAPQ ARILGHSSTG GFVSHCGWSS IAESMKFGVP VIAMARHLDQ    360
PLNGKLAAEV GVGMEVVRDE NGKYKREGIA EVIRKVVVEK SGEVMRRKAR ELSEKMKEKG    420
EEEIDRAVEE LVQICKKKKD AQ                                            442

SEQ ID NO: 101          moltype = DNA   length = 48
FEATURE                 Location/Qualifiers
misc_feature            1..48
                        note = primer
source                  1..48
                        mol_type = other DNA
                        organism = synthetic construct
SEQUENCE: 101
aactttaaga aggagatata ccatgggcat ggataaccaa aaaggtag                  48

SEQ ID NO: 102          moltype = DNA   length = 46
FEATURE                 Location/Qualifiers
misc_feature            1..46
                        note = primer
source                  1..46
                        mol_type = other DNA
                        organism = synthetic construct
SEQUENCE: 102
tcgagtgcgg ccgcaagctt gtcgacctat tgtgcatctt tcttct                    46

SEQ ID NO: 103          moltype = DNA   length = 48
FEATURE                 Location/Qualifiers
misc_feature            1..48
                        note = primer
source                  1..48
                        mol_type = other DNA
                        organism = synthetic construct
SEQUENCE: 103
aactttaaga aggagatata ccatgggcat ggataaccaa gaaggtag                  48

SEQ ID NO: 104          moltype = DNA   length = 46
FEATURE                 Location/Qualifiers
misc_feature            1..46
                        note = primer
source                  1..46
                        mol_type = other DNA
                        organism = synthetic construct
SEQUENCE: 104
tcgagtgcgg ccgcaagctt gtcgacctat tgttcatctt tcttct                    46

SEQ ID NO: 105          moltype = DNA   length = 48
FEATURE                 Location/Qualifiers
misc_feature            1..48
                        note = primer
source                  1..48
                        mol_type = other DNA
                        organism = synthetic construct
SEQUENCE: 105
aactttaaga aggagatata ccatgggcat ggataaccaa gaaggtag                  48

SEQ ID NO: 106          moltype = DNA   length = 46
FEATURE                 Location/Qualifiers
misc_feature            1..46
                        note = primer
source                  1..46
                        mol_type = other DNA
                        organism = synthetic construct
SEQUENCE: 106
tcgagtgcgg ccgcaagctt gtcgacttaa tattgtgcgt gctgct                    46

SEQ ID NO: 107          moltype = DNA   length = 48
FEATURE                 Location/Qualifiers
misc_feature            1..48
                        note = primer
source                  1..48
                        mol_type = other DNA
                        organism = synthetic construct
SEQUENCE: 107
aactttaaga aggagatata ccatgggcat ggataaccaa aaaggtag                  48

SEQ ID NO: 108          moltype = DNA   length = 46
FEATURE                 Location/Qualifiers
misc_feature            1..46
```

```
                          note = primer
source                    1..46
                          mol_type = other DNA
                          organism = synthetic construct
SEQUENCE: 108
tcgagtgcgg ccgcaagctt gtcgacctat tgttcatctt tcttct          46

SEQ ID NO: 109            moltype = DNA  length = 49
FEATURE                   Location/Qualifiers
misc_feature              1..49
                          note = primer
source                    1..49
                          mol_type = other DNA
                          organism = synthetic construct
SEQUENCE: 109
aactttaaga aggagatata ccatgggcat ggatatcgaa aaaggtaga       49

SEQ ID NO: 110            moltype = DNA  length = 45
FEATURE                   Location/Qualifiers
misc_feature              1..45
                          note = primer
source                    1..45
                          mol_type = other DNA
                          organism = synthetic construct
SEQUENCE: 110
tcgagtgcgg ccgcaagctt gtcgacttaa tattgtgcgt gctgc           45

SEQ ID NO: 111            moltype = DNA  length = 49
FEATURE                   Location/Qualifiers
misc_feature              1..49
                          note = primer
source                    1..49
                          mol_type = other DNA
                          organism = synthetic construct
SEQUENCE: 111
aactttaaga aggagatata ccatgggcat ggataaccaa gaaggtaga       49

SEQ ID NO: 112            moltype = DNA  length = 48
FEATURE                   Location/Qualifiers
misc_feature              1..48
                          note = primer
source                    1..48
                          mol_type = other DNA
                          organism = synthetic construct
SEQUENCE: 112
tcgagtgcgg ccgcaagctt gtcgacctat tgtgcatctt tcttcttc        48

SEQ ID NO: 113            moltype = DNA  length = 26
FEATURE                   Location/Qualifiers
misc_feature              1..26
                          note = primer
source                    1..26
                          mol_type = other DNA
                          organism = synthetic construct
SEQUENCE: 113
agtaagaaaa acagagttca tcatgg                                26

SEQ ID NO: 114            moltype = DNA  length = 20
FEATURE                   Location/Qualifiers
misc_feature              1..20
                          note = primer
source                    1..20
                          mol_type = other DNA
                          organism = synthetic construct
SEQUENCE: 114
gcctcggtta ggctagctgt                                       20

SEQ ID NO: 115            moltype = DNA  length = 1329
FEATURE                   Location/Qualifiers
misc_feature              1..1329
                          note = GT29-19
source                    1..1329
                          mol_type = other DNA
                          organism = Panax ginseng
SEQUENCE: 115
atggataacc aagaaggtag aatcagtata gcgttgctac cattttttagc ccatggtcac   60
atatctccct tctttgagct agccaaacaa ctcgcaaaaa gaaattgcaa tgttttcctc  120
tgttctaccc caatcaatct tagctccatc aagaataagg attcctctgc ttctataaaa  180
ctagttgagc ttcatcttcc atcttcccct gatcttcctc ctcactatca caccacaaat  240
```

```
ggcctccctt cccatctcat ggtcccactc ataaacgcct ttgaaacagc aggccccacc    300
ttctctgaaa tccttaaaac cttaaacccc gatttgctta tttatgattt caatccctca    360
tgggcaccgg agatcgcttc gtctcacaat attccggcag tttatttcct aaccacggca    420
gcagccagct cttccattgg cctacatgct ttcaaaaacc caggtgaaaa atacccattt    480
ccagattttt atgataacag taataatacc cctgaaccac cttctgcaga taacatgaag    540
ctacttcatg attttatcgc ttgtttcgaa cgatcttgcg acattatttt gattaagagt    600
tttatagaac tagaagggaa atatatcgat ttgctttcca ctttatctga taaaactttg    660
gttcctgttg gtccactcgt tcaagatcct atgggccata tgaagatcc  aaaaacagag    720
cagattataa actggcttga caaaagggct gaatctacag tggtgtttgt ctgctttgga    780
agtgagtatt ttctctccaa tgaggaattg aagaagtgca caattgggct agagattagc    840
atggttaatt tcatatgggc tgtgagatta attgaaggag agaaaaaagg gttttacca     900
gagggatttg ttcaaagggt aggagacaga ggattggttg tggaggggtg ggctccacag    960
gcaagaattt taggacattc aagcaccggt gggtttgtga gccattgtgg gtggagttct   1020
attacggaga gtatgaagtt tggggttcca gtaattgcca tggccaggca ttttgatcag   1080
cctttgaatg ctaagctggc ggcggaggtt ggtgtgggca tggaggttgt gagagatgaa   1140
aatgggaagt ataagagaga agatattgca ggggtaataa gaaagtcgt  ggtggagaaa   1200
agtggggagg ttatcaggag gaaagcaagg gaattgagtg agaaaatgaa agagatagga   1260
gagcaattga ttgatagggc agtggaggag ctagtacaaa tttgtaagaa gaagaaagat   1320
gaacaatag                                                           1329

SEQ ID NO: 116         moltype = AA  length = 442
FEATURE                Location/Qualifiers
REGION                 1..442
                       note = misc_feature - GT29-19
source                 1..442
                       mol_type = protein
                       organism = Panax ginseng
SEQUENCE: 116
MDNQEGRISI ALLPFLAHGH ISPFFELAKQ LAKRNCNVFL CSTPINLSSI KNKDSSASIK     60
LVELHLPSSP DLPPHYHTTN GLPSHLMVPL INAFETAGPT FSEILKTLNP DLLIYDFNPS    120
WAPEIASSHN IPAVYFLTTA AASSSIGLHA FKNPGEKYPF PDFYDNSNNT PEPPSADNMK    180
LLHDFIACFE RSCDIILIKS FIELEGKYID LLSTLSDKTL VPVGPLVQDP MGHNEDPKTE    240
QIINWLDKRA ESTVVFVCFG SEYFLSNEEL EEVAIGLEIS MVNFIWAVRL IEGEKKGVLP    300
EGFVQRVGDR GLVVEGWAPQ ARILGHSSTG GFVSHCGWSS ITESMKFGVP VIAMARHFDQ    360
PLNAKLAAEV GVGMEVVRDE NGKYKREDIA GVIRKVVVEK SGEVIRRKAR ELSEKMKEIG    420
EQLIDRAVEE LVQICKKKKD EQ                                             442

SEQ ID NO: 117         moltype = DNA  length = 1329
FEATURE                Location/Qualifiers
misc_feature           1..1329
                       note = GT29-20
source                 1..1329
                       mol_type = other DNA
                       organism = Panax ginseng
SEQUENCE: 117
atggataacc aaaaaggtag aatcagtata gcgttgctac cattttttagc ccatggtcac    60
atatctccct tctttgagct agccaaacaa ctcgcgaaaa gaaattgcaa tgttttcctc   120
tgttctaccc caatcaatct tagctccatc aaggataagg attcctctgc ttctataaaa   180
ctagttgagc ttcatcttcc atcttcccct gatcttcctc tcactatca  caccacaaat   240
ggcctccctt cccatctcat gctcccactc agaaacgcct ttgaaactgc aggccccacc   300
ttctctgaaa tccttaaaac cttaaacccc gatttgctta tttatgattt caatccctca   360
tgggcaccgg agatcgcttc gtctcacaat attccggcag tttatttcct aaccacggca   420
gcagccagct cttccattgg cctacatgct ttcaaaaacc caggtgaaaa atacccattt   480
ccagattttt atgataacag taatattacc cctgaaccac cttctgcaga taacatgaag   540
ctacttcatg attttatcgc ttgtttcgaa cgatcttgcg acattatttt gattaagagt   600
tttagagaac tagaagggaa atatattgat ttgctttcca ctttatctga taaaactttg   660
gttcctgttg gtccactcgt tcaagatcct atgggccata tgaagatcc  aaaaacagag   720
cagattataa actggcttga caaaagggct gaatctacag tggtgtttgt ctgctttgga   780
agtgagtatt ttctctccaa tgaggaattg aagaagtgca caattgggct agagattagc   840
acggttaatt tcatatgggc tgtgagatta attgaaggag agaaaaaagg gattttacca   900
gaggggtttg ttcaaagggc aggagacaga ggattggttg tggaggggtg ggctccacag   960
gcaagaattt taggacattc aagcaccggt gggtttgtga gccattgtgg gtggagttct  1020
attgcggaga gtatgaagtt tggggttcca gtaattgcca tggccaggca tcttgatcag  1080
cctttgaatg gtaagctggc ggcggaggtt ggtgtgggca tggaggttgt gagagatgaa  1140
aatgggaagt ataagagaga agggattgca gaggtaataa gaaagtggt  tgtgagaaa   1200
agtggggagg ttatcaggag gaaagcaagg gagttgagtg agaaaatgaa agagaaagga  1260
gagcaagaga ttgatagggc attggaggag ctagtacaaa tttgtaagaa gaagaaagat  1320
gaacaatag                                                          1329

SEQ ID NO: 118         moltype = AA  length = 442
FEATURE                Location/Qualifiers
REGION                 1..442
                       note = misc_feature - GT29-20
source                 1..442
                       mol_type = protein
                       organism = Panax ginseng
SEQUENCE: 118
MDNQKGRISI ALLPFLAHGH ISPFFELAKQ LAKRNCNVFL CSTPINLSSI KDKDSSASIK     60
LVELHLPSSP DLPPHYHTTN GLPSHLMLPL RNAFETAGPT FSEILKTLNP DLLIYDFNPS    120
```

```
WAPEIASSHN IPAVYFLTTA AASSSIGLHA FKNPGEKYPF PDFYDNSNIT PEPPSADNMK    180
LLHDFIACFE RSCDIILIKS FRELEGKYID LLSTLSDKTL VPVGPLVQDP MGHNEDPKTE    240
QIINWLDKRA ESTVVFVCFG SEYFLSNEEL EEVAIGLEIS TVNFIWAVRL IEGEKKGILP    300
EGFVQRAGDR GLVVEGWAPQ ARILGHSSTG GFVSHCGWSS IAESMKFGVP VIAMARHLDQ    360
PLNGKLAAEV GVGMEVVRDE NGKYKREGIA EVIRKVVVEK SGEVIRRKAR ELSEKMKEKG    420
EQEIDRALEE LVQICKKKKD EQ                                             442

SEQ ID NO: 119          moltype = DNA   length = 1329
FEATURE                 Location/Qualifiers
misc_feature            1..1329
                        note = GT29-21
source                  1..1329
                        mol_type = other DNA
                        organism = Panax ginseng
SEQUENCE: 119
atggataacc aaaaaggtag aatcagtata gcgttgctac cattttttagc ccatggtcac    60
atatctccct tctttgagct agccaaacaa ctcgcgaaaa gaaattgcaa tgttttcctc   120
tgttctaccc caatcaatct tagctccatc aaggataagg attcctctgc ttctataaaa   180
ctagttgagc ttcatcttcc atcttcccct gatcttcctc ctcactatca caccacaaat   240
ggcctccctt cccatctcat gctcccactc agaaacgcct ttgaaactgc aggccccacc   300
ttctctgaaa tccttaaaac cttaaacccc gatttgctta tttatgattt caatccctca   360
tgggcaccgg agatcgcttc gtctcacaat attccggcag tttatttcct aaccacggca   420
gcagccagct cttccattgg cctacatgct ttcaaaaacc caggtgaaaa ataccccattt   480
ccagatttt atgataacag taatattacc cctgaaccac cttctgcaga taacatgaag   540
ctacttcatg attttatcgc ttgtttcgaa cgatcttgcg acattatttt gattaagagt   600
tttagagaac tagaagggaa atatattgat ttgctttcca ctttatctga taaaacttttg   660
gttcctgttg gtccactcgt tcaagatcct atgggccata tgaagatcc aaaaaacagag   720
cagattataa actggcttga caaaagggct gaatctacag tggtgtttgt ctgctttgga   780
agtgagtatt ttctctccaa tgaggaattg aagaagtag caattgggct agagattagc   840
acggttaatt tcatatgggc tgtgagatta attgaaggag agaaaaaagg gattttacca   900
gagggggttg ttcaaagggg aggagacaga ggattggttg tggaggggtg ggctccacag   960
gcaagaattt taggacattc aagcatcggt gggtttgtga gccattgtgg gtggagttct  1020
attgcgagag tatgaagtt tggggttcca gtaattgcca tggccaggca tcttgatcag  1080
cctttgaatg gtaagctggc ggcggaggtt ggtgtgggca tggaggttgt gagagatgag  1140
aatggggaagt ataagagaga agggattgca gaggtaataa gaaaagtgt tgtgagaaa  1200
agtggggagg ttatcaggag gaaagcaagg gagttgagtg agaaaatgaa agagaaagga  1260
gagcaagaga ttgatagggc attggaggag ctagtacaaa tttgtaagaa gaagaaagat  1320
gaacaatag                                                           1329

SEQ ID NO: 120          moltype = AA   length = 442
FEATURE                 Location/Qualifiers
REGION                  1..442
                        note = misc_feature - GT29-21
source                  1..442
                        mol_type = protein
                        organism = Panax ginseng
SEQUENCE: 120
MDNQKGRISI ALLPFLANGH ISPFFELAKQ LAKRNCNVFL CSTPINLSSI KDKDSSASIK    60
LVELHLPSSP DLPPHYHTTN GLPSHLMLPL RNAFETAGPT FSEILKTLNP DLLIYDFNPS   120
WAPEIASSHN IPAVYFLTTA AASSSIGLHA FKNPGEKYPF PDFYDNSNIT PEPPSADNMK   180
LLHDFIACFE RSCDIILIKS FRELEGKYID LLSTLSDKTL VPVGPLVQDP MGHNEDPKTE   240
QIINWLDKRA ESTVVFVCFG SEYFLSNEEL EEVAIGLEIS TVNFIWAVRL IEGEKKGILP   300
EGFVQRVGDR GLVVEGWAPQ ARILGHSSIG GFVSHCGWSS IAESMKFGVP VIAMARHLDQ   360
PLNGKLAAEV GVGMEVVRDE NGKYKREGIA EVIRKVVVEK SGEVIRRKAR ELSEKMKEKG   420
EQEIDRALEE LVQICKKKKD EQ                                            442

SEQ ID NO: 121          moltype = DNA   length = 1329
FEATURE                 Location/Qualifiers
misc_feature            1..1329
                        note = GT29-22
source                  1..1329
                        mol_type = other DNA
                        organism = Panax ginseng
SEQUENCE: 121
atggataacc aaaaaggtag aatcagtata gcgttgctac cattttttagc ccatggtcac    60
atatctccct tctttgagct agccaaacaa ctcgcgaaaa gaaattgcaa tgttttcctc   120
tgttctaccc caatcaatct tagctccatc aaggataagg attcctctgc ttctataaaa   180
ctagttgagc ttcatcttcc atcttcccct gatcttcctc ctcactatca caccacaaat   240
ggcctccctt cccatctcat gctcccactc agaaacgcct ttgaaactgc aggccccacc   300
ttctctgaaa tccttaaaac cttaaacccc gatttgctta tttatgattt caatccctca   360
tgggcaccgg agatcgcttc gtctcacaat attccggcag tttatttcct aaccacggca   420
gcagccagct cttccattgg cctacatgct ttcaaaaacc caggtgaaaa ataccccattt   480
ccagatttt atgataacag taatattacc cctgaaccac cttctgcaga taacatgaag   540
ctacttcatg attttatcgc ttgtttcgaa cgatcttgcg acattatttt gattaagagt   600
tttagagaac tagaagggaa atatattgat ttgctttcca ctttatctga taaaactttg   660
gttcctgttg gtccactcgt tcaagatcct atgggccata tgaagatcc aaaaaacagag   720
cagattataa actggcttga caaaagggct gaatctacag tggtgtttgt ctgctttgga   780
agtgagtatt ttctctccaa tgaggaattg aagaagtag caattgggct agagattagc   840
acggttaatt tcatatgggc tgtgagatta attgaaggag agaaaaaagg gattttacca   900
```

```
gaggggtttg ttcaaagggt aggagacaga ggattggttg tgaggggtg ggctccacag   960
gcaagaattt taggacattc aagcaccggt gggtttgtga gccattgtgg gtggagttct  1020
attgcggaga ttatgaagtt tggggttcca gtaattgcca tggccaggca tcttgatcag  1080
cctttgaatg gtaagctggc ggcggaggtt ggtgtgggca tggaggttgt gagagatgag  1140
aatgggaagt ataagagaga agggattgca gaggtaataa gaaaagtaag tgtggagaaa  1200
agtggggagg ttatcaggag gaaagcaagg gagttgagtg agaaaatgaa agagaaagga  1260
gagcaagaga ttgatagggc attggaggag ctagtacaaa tttgtaagaa gaagaaagat  1320
gaacaatag                                                         1329

SEQ ID NO: 122          moltype = AA   length = 442
FEATURE                 Location/Qualifiers
REGION                  1..442
                        note = misc_feature - GT29-22
source                  1..442
                        mol_type = protein
                        organism = Panax ginseng
SEQUENCE: 122
MDNQKGRISI ALLPFLAHGH ISPFFELAKQ LAKRNCNVFL CSTPINLSSI KDKDSSASIK   60
LVELHLPSSP DLPPHYHTTN GLPSHLMLPL RNAFETAGPT FSEILKTLNP DLLIYDFNPS  120
WAPEIASSHN IPAVYFLTTA AASSSIGLHA FKNPGEKYPF PDFYDNSNIT PEPPSADNMK  180
LLHDFIACFE RSCDIILIKS FRELEGKYID LLSTLSDKTL VPVGPLVQDP MGHNEDPKTE  240
QIINWLDKRA ESTVVFVCFG SEYFLSNEEL EEVAIGLEIS TVNFIWAVRL IEGEKKGILP  300
EGFVQRVGDR GLVVEGWAPQ ARILGHSSTG GFVSHCGWSS IAEIMKFGVP VIAMARHLDQ  360
PLNGKLAAEV GVGMEVVRDE NGKYKREGIA EVIRKVVVEK SGEVIRRKAR ELSEKMKEKG  420
EQEIDRALEE LVQICKKKKD EQ                                          442

SEQ ID NO: 123          moltype = DNA   length = 1329
FEATURE                 Location/Qualifiers
misc_feature            1..1329
                        note = GT29-23
source                  1..1329
                        mol_type = other DNA
                        organism = Panax ginseng
SEQUENCE: 123
atggataacc aagaaggtag aatcagtata gcgttgctac cattttttagc ccatggtcac   60
atatctccct tctttgagct agccaaacaa ctcgcaaaaa gaaattgcaa tgttttcctc  120
tgttctaccc caatcaatct tagctccatc aagaataagg attcctctgc ttctataaaa  180
ctagttgagc ttcatcttcc atcttcccct gatcttcctc ctcactatca caccacaaat  240
ggcctccctt cccatctcat ggtcccactc ataaacgcct ttgaaacagc aggccccacc  300
ttctctgaaa tccttaaaac cttaaacccc gatttgctta tttatgattt caatccctca  360
tgggcaccgg agatcgcttc gtctcacaat attccggcag tttatttcct aaccacggca  420
gcagccagct cttccattgg cctacatgct ttcaaaaacc caggtgaaaa atacccattt  480
ccagattttt atgataacag taataatacc cctgaaccac ctctgcagaa taacatgaag  540
ctacttcatg attttatcgc ttgtttcgaa cgatctgcg acattatttt gattaagagt  600
tttatagaac tagaagggaa atatatcgat ttgctttcca ctttatctga taaaactttg  660
gttcctgttg gtccactcgt tcaagatcct atgggccata tgaagatcc aaaaacagag  720
cagattataa actggcttga caaaagggct gaatctacta tggtgttttgt ctgctttgga  780
agtgagtatt ttctctccaa tgaggaattg gaagaagtag caattgggct agagattagc  840
atggttaatt tcatatgggc tgtgagatta attgaaggag agaaaaaagg ggttttacca  900
gagggatttg ttcaaagggt aggagacaga ggattggttg tggaggggtg ggctccacac  960
gcaagaattt taggacattc aagcaccggt gggtttgtga gccattgtgg gtggagttct  1020
attgcggaga gtatgaagtt tggggttcca gtaattgcca tggccaggca tcttgatcag  1080
cctttgaatg gtaagctggc ggcggaggtt ggtgtgggca tggaggttgt gagagatgaa  1140
aatgggaagt ataagagaga agggattgca gaggtaataa gaaaagtcgt tgtggagaaa  1200
agtggggagg ttatgaggag gaaagcaagg gaattgagtg agaaaatgaa agagaaagga  1260
gaggaagaga ttgatagggc agtggaggag ctagtacaaa tttgtaagaa gaagaaagat  1320
gcacaatag                                                         1329

SEQ ID NO: 124          moltype = AA   length = 442
FEATURE                 Location/Qualifiers
REGION                  1..442
                        note = misc_feature - GT29-23
source                  1..442
                        mol_type = protein
                        organism = Panax ginseng
SEQUENCE: 124
MDNQEGRISI ALLPFLAHGH ISPFFELAKQ LAKRNCNVFL CSTPINLSSI KNKDSSASIK   60
LVELHLPSSP DLPPHYHTTN GLPSHLMVPL INAFETAGPT FSEILKTLNP DLLIYDFNPS  120
WAPEIASSHN IPAVYFLTTA AASSSIGLHA FKNPGEKYPF PDFYDNSNNT PEPPSADNMK  180
LLHDFIACFE RSCDIILIKS FIELEGKYID LLSTLSDKTL VPVGPLVQDP MGHNEDPKTE  240
QIINWLDKRA ESTVVFVCFG SEYFLSNEEL EEVAIGLEIS MVNFIWAVRL IEGEKKGVLP  300
EGFVQRVGDR GLVVEGWAPH ARILGHSSTG GFVSHCGWSS IAESMKFGVP VIAMARHLDQ  360
PLNGKLAAEV GVGMEVVRDE NGKYKREGIA EVIRKVVVEK SGEVMRRKAR ELSEKMKEKG  420
EEEIDRAVEE LVQICKKKKD AQ                                          442

SEQ ID NO: 125          moltype = DNA   length = 48
FEATURE                 Location/Qualifiers
misc_feature            1..48
                        note = primer
```

```
source                      1..48
                            mol_type = other DNA
                            organism = synthetic construct
SEQUENCE: 125
aactttaaga aggagatata ccatgggcat ggataaccaa gaaggtag              48

SEQ ID NO: 126              moltype = DNA   length = 46
FEATURE                     Location/Qualifiers
misc_feature                1..46
                            note = primer
source                      1..46
                            mol_type = other DNA
                            organism = synthetic construct
SEQUENCE: 126
tcgagtgcgg ccgcaagctt gtcgacttgt tcatctttct tcttct               46

SEQ ID NO: 127              moltype = DNA   length = 48
FEATURE                     Location/Qualifiers
misc_feature                1..48
                            note = primer
source                      1..48
                            mol_type = other DNA
                            organism = synthetic construct
SEQUENCE: 127
aactttaaga aggagatata ccatgggcat ggataaccaa aaaggtag              48

SEQ ID NO: 128              moltype = DNA   length = 46
FEATURE                     Location/Qualifiers
misc_feature                1..46
                            note = primer
source                      1..46
                            mol_type = other DNA
                            organism = synthetic construct
SEQUENCE: 128
tcgagtgcgg ccgcaagctt gtcgacttgt tcatctttct tcttct               46

SEQ ID NO: 129              moltype = DNA   length = 48
FEATURE                     Location/Qualifiers
misc_feature                1..48
                            note = primer
source                      1..48
                            mol_type = other DNA
                            organism = synthetic construct
SEQUENCE: 129
aactttaaga aggagatata ccatgggcat ggataaccaa aaaggtag              48

SEQ ID NO: 130              moltype = DNA   length = 46
FEATURE                     Location/Qualifiers
misc_feature                1..46
                            note = primer
source                      1..46
                            mol_type = other DNA
                            organism = synthetic construct
SEQUENCE: 130
tcgagtgcgg ccgcaagctt gtcgacttgt tcatctttct tcttct               46

SEQ ID NO: 131              moltype = DNA   length = 48
FEATURE                     Location/Qualifiers
misc_feature                1..48
                            note = primer
source                      1..48
                            mol_type = other DNA
                            organism = synthetic construct
SEQUENCE: 131
aactttaaga aggagatata ccatgggcat ggataaccaa aaaggtag              48

SEQ ID NO: 132              moltype = DNA   length = 46
FEATURE                     Location/Qualifiers
misc_feature                1..46
                            note = primer
source                      1..46
                            mol_type = other DNA
                            organism = synthetic construct
SEQUENCE: 132
tcgagtgcgg ccgcaagctt gtcgacttgt tcatctttct tcttct               46

SEQ ID NO: 133              moltype = DNA   length = 48
FEATURE                     Location/Qualifiers
misc_feature                1..48
```

```
                        note = primer
source                  1..48
                        mol_type = other DNA
                        organism = synthetic construct
SEQUENCE: 133
aactttaaga aggagatata ccatgggcat ggataaccaa gaaggtag            48

SEQ ID NO: 134          moltype = DNA  length = 46
FEATURE                 Location/Qualifiers
misc_feature            1..46
                        note = primer
source                  1..46
                        mol_type = other DNA
                        organism = synthetic construct
SEQUENCE: 134
tcgagtgcgg ccgcaagctt gtcgacttgt gcatctttct tcttct              46
```

GROUP OF UDP-GLYCOSYLTRANSFERASE FOR CATALYZING CARBOHYDRATE CHAIN ELONGATION AND APPLICATION THEREOF

CROSS REFERENCE TO RELATED APPLICATIONS

The present application is a divisional application of U.S. patent application Ser. No. 16/614,944 filed Nov. 9, 2019 and issued as U.S. Pat. No. 11,542,484 B2 on Jan. 3, 2023, which is the 35 U.S.C. 371 National Stage of International Application Number PCT/CN2018/087678, field on May 21, 2018, which claims priority of Chinese Patent Application No. CN201710359069.7, filed May 19, 2017, the contents of each of which are incorporated herein by reference in their entireties.

SEQUENCE LISTING

This application contains a Sequence Listing that has been submitted in XML format vis Patent Center and is hereby incorporated by reference in its entirety. The XML copy is named "104775-736307.xml", was created on Jan. 5, 2023 and is 219 Kilobytes.

TECHNICAL FIELD

The present invention relates to the field of biotechnology and plant biology, and in particular, the present invention relates to a group of glycosyltransferases and uses thereof.

BACKGROUND

Ginsenoside is a generic term for saponins isolated from the plants of *Panax* genus (such as *Ginseng, Panax notoginseng*, American *Ginseng*, etc.) and *Gynostemma pentaphyllum*, and is a class of triterpenoids. Ginsenosides may also be called as ginsenosides, notoginsenosides, and gypenosides depending on the source from which they are isolated. Ginsenosides are the main biologically active ingredient in these medicinal plants. Currently, about 150 kinds of saponins have been isolated. Structurally, ginsenosides are mainly bioactive small molecules formed by glycosylation of sapogenins. There are only a few sapogenins of ginsenosides, mainly of which are protopanoxadiol and protopanaxatriol of dammarane type tetracyclic triterpenes, and oleanolic acid. Glycosylation of sapogenin can increase its water solubility, alter its subcellular localization, and produce different biological activities. Most of the protopanaxadiol saponins are glycosylated on the C3 and/or C20 hydroxyl groups, while the protopanaxatriol saponins are glycosylated on the C6 and/or C20 hydroxyl groups. Different types of glycosylation and varying degrees of glycosylation modification produce ginsenosides with a multitude of molecular structures.

Ginsenosides with different glycosylation modifications have different biological activities. For example, Rb1, Rb2 and Rb3 are Rds with a molecule of glucose, arabinose and xylose extended on the C20-O-Glc, respectively. The experiment has confirmed that the rich saponin Rb1 has the effects of protecting nerve cells and anti-inflammation and anti-oxidation; Rb2 has the effects of inhibiting tumor angiogenesis and tumor metastasis, reducing blood glucose in diabetic mice and reducing blood lipid; Rb3 has the effects of slowing down myocardial ischemia and anti-depression.

Ginsenosides are prepared by using total saponins of *Ginseng* or *Panax notoginseng* or rich saponins as raw materials, depending on a hydrolysis method of chemical, enzymatic and microbial fermentation. Since wild *Ginseng* resources have been basically depleted, ginsenoside resources are currently derived from artificial cultivation of *Ginseng* or *notoginseng*. Their artificial cultivation has a long growth cycle (generally 5-7 years or more) and is geographically restricted. It is often subject to pests and diseases, thereby requiring a large amount of pesticides. Therefore, there is a serious continuous cropping obstacle during the artificial cultivation of *Ginseng* or *Panax notoginseng* (the *Ginseng* or *Panax notoginseng* plantation needs to fallow for more than 5-15 years to overcome the continuous cropping obstacle), so the yield, quality and security of ginsenosides are all facing challenges.

The development of synthetic biology offers new opportunities for heterologous synthesis of plant-derived natural products. Using yeast as a chassis, through the assembly and optimization of metabolic pathways, it has been realized to synthesize artemisinic acid or dihydroartemisinic acid with cheap monosaccharides, and then to produce artemisinin by one-step chemical conversion, which indicates the synthetic biology has a great potential for drug synthesis in natural products. Ginsenoside monomers are heterologous synthesized by synthetic biological methods using the yeast chassis cells, and the raw materials are cheap monosaccharides, and the preparation process is a safe and controllable fermentation process, thereby avoiding any external contamination (for example, pesticides used in the artificial planting of raw plants). Therefore, the preparation of ginsenoside monomer by synthetic biology technology not only has cost advantages, but also ensures the quality and safety of the finished product. Synthetic biological techniques are used to prepare a sufficient amount of various high-purity natural and non-natural ginseno side monomers for activity determination and clinical experiments to promote the development of innovative drugs for rare ginsenosides.

In recent years, through the transcriptome and functional genomic studies on *Ginseng, notoginseng* and American *Ginseng*, the analysis of the saponin synthesis pathway of ginsenosides has made great progress. In 2006, Japanese and Korean scientists identified the terpenoid cyclase element (dammarenediol synthase, PgDDS), which converts epoxy squalene to dammarene diol. From 2011 to 2012, Korean scientists further identified cytochrome P450 elements CYP716A4 and CYP716A53v2, which oxidize dammarene diol to protopanaxadiol and further oxidize protopanaxadiol to protopanaxatriol.

The artificial synthesis of these pharmaceutically active ginsenosides by synthetic biological methods requires not only the construction of a metabolic pathway for the synthesis of sapogenins, but also the identification of a UDP-glycosyltransferase that catalyzes the glycosylation of ginsenosides. The function of UDP-glycosyltransferase is to transfer glycosyl groups from glycosyl donors (nucleoside diphosphates such as UDP-glucose, UDP-rhamnose, UDP-xylose and UDP-arabinose) to different glycosyl acceptors. According to the genome analysis of plants that have been sequenced, the plant genome often encodes hundreds of different glycosyltransferases. Since the substrates (including glycosyl donors and glycosyl acceptors) that may be catalyzed by UDP-glycosyltransferase are very diverse, the functional identification of this UDP-glycosyltransferase poses great difficulties. Until 2014, the first UDP-glycosyltransferase (UGTPg1) involved in ginsenoside glycosylation was identified by Chinese scholars, which can be transferred to a glucosyl group on the C20 hydroxyl group of the Protopanaxadiol ginsenoside. Subsequently, Korean scientists cloned two UDP-glycosyltransferase elements (PgUGT74AE2 and PgUGT94Q2) in *Ginseng*, which can transferr a glucosyl group and a glucosyl extension to the C3 position of the Protopanaxadiol saponin. Almost at the same time, Chinese scholars also independently cloned two glycosyltransferase elements UGTPg45 and UGTPg29, which have the same functions as PgUGT74AE2 and PgUGT94Q2, from *Ginseng*. In 2015, Chinese scholars further identified a UDP-glycosyltransferase element (UGTPg100) that can transferr a glucosyl group to the C6 position of the Protopanaxatriol. In 2015, Korean scholars discovered a glycosyltransferase GpUGT23 that extends a glucosyl group on C20 of Protopanaxadiol and protopanaxatriol saponin in *Gynostemma pentaphyllum*. However, up to now, in addition to a glycosyltransferase plant extending a glycosyl at the C3 position, other glycosyltransferases in *Ginseng* that catalyze the extension of the carbohydrate chain have not been reported.

Under this background, the inventors have cloned and identified the glycosyltransferase which can extend a glucosyl or xylosyltaxol on the C20 of the Protopanaxadiol and protopanaxatriol saponin and the glycosyltransferase which can extend a xylosyltaxol on the C6 of the protopanaxatriol saponin. The glycosyltransferase can be used for the preparation of ginsenosides including ginsenoside Rb1, ginsenoside Rb3, gypenoside LXXV, gypenoside XVII, notoginsenoside U, notoginsenoside R1, notoginsenoside R2 and notoginsenoside R3.

SUMMARY OF THE INVENTION

The present invention provides a novel set of glycosyltransferases and a method for catalyzing a glycosylation reaction of a tetracyclic triterpenoid using the glycosyltransferases.

In a first aspect of the present invention, it provides an in vitro glycosylation method, comprising the steps of:
transferring a glycosyl group from the glycosyl donor to the following positions of the tetracyclic triterpenoid in the presence of a glycosyltransferase:
the first glycosyl group on position C20 and/or position C3;
thereby forming a glycosylated tetracyclic triterpenoid;
wherein the glycosyltransferase is selected from the group consisting of:
a glycosyltransferase as shown in SEQ ID NO.: 4, 6, 8, 8, 39, 41, 43, 45, 47, 49, 51, 53, 55, 57, 59, 98, or 100 or a derivative polypeptide thereof.

In another preferred embodiment, the tetracyclic triterpenoids glycosylated at the position C20 include ginsenosides Rd, CK, F1 and F2.

In a second aspect of the present invention, it provides an in vitro glycosylation method, comprising the steps of:
transferring a glycosyl group from a glycosyl donor to the following positions of the tetracyclic triterpenoid in the presence of a glycosyltransferase:
the first glycosyl group on position C6;
thereby forming a glycosylated tetracyclic triterpenoid;
wherein the glycosyltransferase is selected from the group consisting of:
a glycosyltransferase as shown in SEQ ID NO.: 12, 14, 16, 18, 20, 22, 24, 26, 28 and 30 or a derivative polypeptide thereof.

In another preferred embodiment, the tetracyclic triterpenoids glycosylated at the position C6 includes Rg1 or Rh1.

The present invention provides a method for in vitro glycosylation comprising the steps of:
transferring a glycosyl group from a glycosyl donor to the following positions of the tetracyclic triterpenoid in the presence of a glycosyltransferase:
the first glycosyl group on position C3;
thereby forming a glycosylated tetracyclic triterpenoid;
wherein the glycosyltransferase is selected from the group consisting of:
a glycosyltransferase as shown in SEQ ID NO.: 39, 41, 43, 45, 47, 49, 51, 53, 55, 57, 59, 90, 92, 94, 96, 98, 100, 116, 118, 120, 122, and 124 or a derivative polypeptide thereof.

In another preferred embodiment, the tetracyclic triterpenoids glycosylated on the position C3 includes F2 or Rh2.

In another preferred embodiment, the derivative polypeptide is independently selected from the group consisting of:
(a) a polypeptide of any one or more of the amino acid sequences as shown in SEQ ID NOs.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124;
(b) a derivative polypeptide formed by adding a tag sequence, a signal sequence or a secretion signal sequence to SEQ ID NOs: 4, 6, 8, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124 and having glycosyltransferase activity;
(c) a derivative polypeptide of an amino acid sequence having an identity of 95% with the amino acid sequence of any one or more of SEQ ID NOs: 4, 6, 8, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124 and having glycosyltransferase activity.

In another preferred embodiment, (c) further includes a derivative polypeptide formed by substitution, deletion or addition of one or several amino acid residues of any one or more of the amino acid sequences of SEQ ID NOs.: 4, 6, 8, 14, 16, 18, 20, 22, 24, 26, 28, 30, 39, 41, 43, 45 47, 49, 51, 53, 55, 57, 59, 90, 92, 94, 96, 98, 100, 116, 118, 120, 122, and 124 and having the glycosyltransferase activity.

In a third aspect of the present invention, it provides an isolated polypeptide, wherein the isolated polypeptide is:
a polypeptide or a derivative polypeptide thereof of any one or more of the amino acid sequences as shown in SEQ ID NOs.: 4, 6, 8, 28, 30, 39, 41, 43, 45, 47, 49, 51, 53, 55, 57, 59, 90, 92, 94, 96, 98, 100, 116, 118, 120, 122, and 124;
wherein the derivative polypeptide is selected from the group consisting of:
(a) a polypeptide of any one or more of the amino acid sequences as shown in SEQ ID NOs.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124;
(b) a derivative polypeptide formed by adding a tag sequence, a signal sequence or a secretion signal sequence to SEQ ID NOs: 4, 6, 8, 28, 30, 39, 41, 43, 45, 47, 49, 51, 53, 55, 57, 59, 90, 92, 94, 96, 98, 100, 116, 118, 120, 122, or 124 and having a glycosyltransferase activity;
(c) a derivative polypeptide of an amino acid sequence having an identity of _95% with the amino acid sequence as shown in any one or more of SEQ ID NOs: 4, 6, 8, 28, 30, 39, 41, 43, 45, 47, 49, 51, 53, 55, 57, 59, 90, 92, 94, 96, 98, 100, 116, 118, 120, 122, and 124 and having a glycosyltransferase activity.

In another preferred embodiment, (c) further includes a derivative polypeptide formed by substitution, deletion or addition of one or several amino acid residues of any one or more of the amino acid sequences of SEQ ID NOs.: 4, 6, 8, 28, 30, 39, 41, 43, 45, 47, 49, 51, 53, 55, 57, 59, 90, 92, 94, 96, 98, 100, 116, 118, 120, 122, and 124 and having a glycosyltransferase activity.

In another preferred embodiment, the isolated polypeptide is used for in vitro glycosylation.

In a fourth aspect of the present invention, it provides an isolated polynucleotide, wherein the polynucleotide is selected from the group consisting of:

(A) a nucleotide sequence encoding a polypeptide as shown in SEQ ID NOs: 4, 6, 8, 28, 30, 39, 41, 43, 45, 47, 49, 51, 53, 55, 57, 59, 90, 92, 94, 96, 100, 116, 118, 120, 122 or 124;

(B) a nucleotide sequence as shown in SEQ ID NO.: 3, 5, 7, 27, 29, 38, 40, 42, 44, 46, 48, 50, 52, 54, 56, 58, 89, 91, 93, 95, 97, 99, 115, 117, 119, 121, or 123;

(C) a nucleotide sequence having an identity of _95% (preferably _98%) with a nucleotide sequence as shown in SEQ ID NO.: 3, 5, 7, 27, 29, 38, 40, 42, 44, 46, 48, 50, 52, 54, 56, 58, 89, 91, 93, 95, 97, 99, 115, 117, 119, 121, or 123;

(D) a nucleotide sequence complementary (preferably completely complementary) to the nucleotide sequence of any of (A)-(D).

In another preferred embodiment, (D) further includes a nucleotide sequence formed by truncation or addition of 1-60 (preferably 1-30, more preferably 1-10) nucleotides at 5' end and/or 3' end of the nucleotide sequences of SEQ ID NOs.: 3, 5, 7, 27, 29, 38, 40, 42, 44, 46, 48, 50, 52, 54, 56, 58, 89, 91, 93, 95, 97, 99, 115, 117, 119, 121, or 123.

In another preferred embodiment, the nucleotide sequences as shown in SEQ ID NO.: 3, 5, 7, 27, 29, 38, 40, 42, 44, 46, 48, 50, 52, 54, 56, 58, 89, 91, 93, 95, 97, 99, 115, 117, 119, 121, or 123, encoding the polypeptides as shown in SEQ ID NOs: 4, 6, 8, 28, 30, 39, 41, 43, 45, 47, 49, 51, 53, 55, 57, 59, 90, 92, 94, 96, 98, 100, 116, 118, 120, 122, or 124.

In a fifth aspect of the present invention, it provides a vector comprising the polynucleotide according to the fourth aspect of the present invention, or expressing the isolated polypeptide according to the third aspect of the present invention.

Use of the isolated polypeptide according to the third aspect of the present invention for catalyzing one or more of the following reactions, or preparing a catalytic formulation which catalyzes one or more of the following reactions:

transferring the glycosyl group from the glycosyl donor to the following positions of the tetracyclic triterpenoid to extend the carbohydrate chain:
  (i) the first glycosyl group on position C-6;
  (ii) the first glycosyl group on position C-20; and/or
  (iii) the first glycosyl group on position C3.

In another preferred embodiment, the glycosyl group transfer comprises the addition or substitution of a glycosyl group on a specific position.

In another preferred embodiment, it also provides a use of a polypeptide or a derivative polypeptide thereof for catalyzing the following reactions or for preparing a catalytic formulation which catalyzes the following reactions:

transferring a glycosyl group from a glycosyl donor to the following positions of the tetracyclic triterpenoid in the presence of a glycosyltransferase:
  the first glycosyl group on position C-6; or the first glycosyl group on position C-20; and/or the first glycosyl group on position C-3;
    thereby forming a glycosylated tetracyclic triterpenoid;
    wherein the glycosyltransferase is selected from the group consisting of:
a glycosyltransferase, or a derivative polypeptide thereof as shown in SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124.

In another preferred embodiment, it also provides a use of a polypeptide or a derivative polypeptide thereof for catalyzing the following reactions, or for preparing a catalytic formulation which catalyzes the following reactions:

transferring a glycosyl group from glycosyl donor to the following positions of the tetracyclic triterpenoid in the presence of a glycosyltransferase:
  the first glycosyl group on position C20 and/or position C3;
  thereby forming a glycosylated tetracyclic triterpenoid;
  wherein the glycosyltransferase is selected from the group consisting of:
a glycosyltransferase or a derivative polypeptide thereof as shown in SEQ ID NO.: 4, 6, 8, 39, 41, 43, 45, 47, 49, 51, 53, 55, 57, 59, 98, and 100.

In another preferred embodiment, it also provides a use of a polypeptide or a derivative polypeptide thereof for catalyzing the following reactions or for preparing a catalytic formulation which catalyzes the following reactions:

transferring a glycosyl group from a glycosyl donor to the following positions of the tetracyclic triterpenoid in the presence of a glycosyltransferase:
  the first glycosyl group on position C6;
  thereby forming a glycosylated tetracyclic triterpenoid;
  wherein the glycosyltransferase is selected from the group consisting of:
a glycosyltransferase or a derivative polypeptide thereof as shown in SEQ ID NO.: 12, 14, 16, 18, 20, 22, 24, 26, 28, and 30.

In another preferred embodiment, it also provides a use of a polypeptide or a derivative polypeptide thereof for catalyzing the following reactions or for preparing a catalytic formulation which catalyzes the following reactions:

transferring a glycosyl group from a glycosyl donor to the following positions of the tetracyclic triterpenoid in the presence of a glycosyltransferase:
  the first glycosyl group on position C-3;
  thereby forming a glycosylated tetracyclic triterpenoid;
  wherein the glycosyltransferase is selected from the group consisting of:
a glycosyltransferase or a derivative polypeptide thereof as shown in SEQ ID NO.: 39, 41, 43, 45, 47, 49, 51, 53, 55, 57, 59, 90, 92, 94, 96, 98, 100, 116, 118, 120, 122, and 124.

In another preferred embodiment, the derivative polypeptide is each selected from the group consisting of:

(a) a polypeptide having an amino acid sequence of any one of SEQ ID NOs.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124;

(b) a derivative polypeptide formed by adding a tag sequence, a signal sequence or a secretion signal sequence to SEQ ID NOs: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124 and having a glycosyltransferase activity;

(c) a derivative polypeptide of an amino acid sequence having an identity of 95% with the amino acid sequence as shown in any one of SEQ ID NOs: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, and 124 and having a glycosyltransferase activity.

In another preferred embodiment, the glycosyl donor comprises a nucleoside diphosphate selected from the group consisting of UDP-glucose, ADP-glucose, TDP-glucose, CDP-glucose, GDP-glucose, UDP-acetylglucose, ADP-acetylglucose, TDP-acetylglucose, CDP-acetylglucose, GDP-acetylglucose, UDP-xylose, ADP-xylose, TDP-xylose, CDP-xylose, GDP-xylose, UDP-galacturonic acid, ADP-galacturonic acid, TDP-galacturonic acid, CDP-galacturonic acid, GDP-galacturonic acid, UDP-galactose, ADP-galactose, TDP-galactose, CDP-galactose, GDP-galactose, UDP-arabinose, ADP-arabinose, TDP-arabinose, CDP-arabinose, GDP-arabinose, UDP-rhamnose, ADP-rhamnose, TDP-rhamnose, CDP-rhamnose, GDP-rhamnose, UDP-xylose, ADP-xylose, TDP-xylose, CDP-xylose, GDP-xylose, and other nucleoside diphosphate hexose and nucleoside pentose diphosphate, and a combination thereof.

In another preferred embodiment, the glycosyl donor comprises a uridine diphosphate (UDP) saccharide selected from the group consisting of UDP-glucose, UDP-galacturonic acid, UDP-galactose, UDP-arabinose, UDP-rhamnose, UDP-xylose, and other uridine diphosphate hexose and uridine pentose diphosphate, and a combination thereof.

In another preferred embodiment, the isolated polypeptide is used to catalyze one or more of the following reactions or to prepare a catalytic formulation which catalyzes one or more of the following reactions:

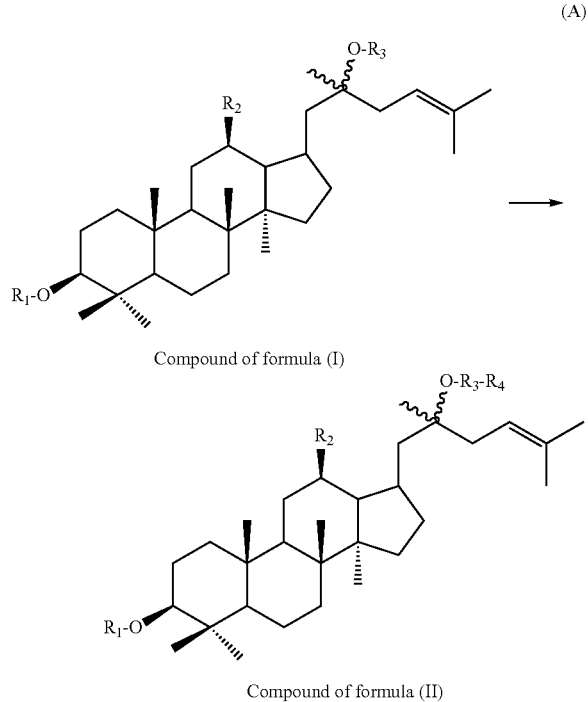

Compound of formula (I)

Compound of formula (II)

wherein, R1 is H, a monosaccharide glycosyl or a polysaccharide glycosyl; R2 is H or OH; R3 is a monosaccharide glycosyl; and R4 is a monosaccharide glycosyl; and the
polypeptide is selected from the group consisting of SEQ ID NOs: 4, 6, 8, 39, 41, 43, 45, 47, 49, 51, 53, 55, 57, 59, 98, 100, 116, 118, 120, 122, or 124 or a derivative polypeptide thereof.

In another preferred embodiment, the monosaccharide comprises glucose (Glc), rhamnose (Rha), acetylglucose (Glc(6)Ac), arabinofuranose (Araf), arabian pyranose (Arap), or xylose (Xyl), etc.

In another preferred embodiment, the polysaccharide comprises a polysaccharide consisting of 2-4 monosaccharides such as Glc(2-1)Glc, Glc(6-1)Glc, Glc(6)Ac, Glc(2-1)Rha, Glc(6-1)Arap, Glc(6-1)Xyl, Glc(6-1)Araf, Glc(3-1)Glc(3-1), Glc(2-1) Glu(6)Ac, Glc(6-1)Arap(4-1)Xyl, Glc(6-1)Arap(2-1)Xyl, or Glc(6-1)Arap(3-1)Xyl.

In another preferred embodiment, the compound with the substitution of R1-R4 is shown in the following table:

| substrate | R1 | R2 | R3 | R4 | product |
|---|---|---|---|---|---|
| CK | H | OH | Glc | Glc | Gypenoside LXXV |
| DMG | H | H | Glc | Glc | DMGG |
| F2 | Glc | OH | Glc | Glc | Gypenoside XVII |
| Rd | Glc(2-1)Glc | OH | Glc | Glc | Rb1 |
| CK | H | OH | Glc | Xyl | Gypenoside XIII |
| DMG | H | H | Glc | Xyl | DMGX |
| F2 | Glc | OH | Glc | Xyl | Gypenoside IX |
| Rd | Glc(2-1)Glc | OH | Glc | Xyl | Rb3 |
| CK | H | OH | Glc | Arabinose | Ginsenoside F3 | that is, when R1 is H, R2 is OH, and R3 is a glucosyl, the compound of formula (I) is ginsenoside CK (CK);

when the R1 is H, R2 is OH, and both R3 and R4 are glucosyls, the compound of the formula (II) is Gypenoside LXXV;

when the R1 is H, R2 is OH, R3 is a glucosyl, and R4 is a xylose group, the compound of the formula (II) is Gypenoside XIII;

when both R1 and R2 are H and R3 is a glucosyl, the compound of formula (I) is ginsenoside DMG;

when both R1 and R2 are H, and both R3 and R4 are glucosyls, the compound of the formula (II) is saponin DMGG (20-O-β-(D-glucopyranosyl)-β-(D-glucopyranosyl)-dammarenediol);

when both R1 and R2 are H, R3 is a glucosyl, and R4 is a xylose group, the compound of the formula (II) is saponin DMGX (20-O-β-(D-xylopyranosyl)-β-(D-glucopyranosyl)-dammarenediol);

when R1 is a glucosyl, R2 is OH, and R3 is a glucosyl, the compound of formula (I) is ginsenoside F2 (F2);

when R1 is a glucosyl, R2 is OH, and both R3 and R4 are glucosyls, the compound of formula (II) is Gypenoside XVII;

when R1 is a glucosyl, R2 is OH, R3 is a glucosyl, and R4 is a xylose group, the compound of formula (II) is Gypenoside IX;

when R1 is two glucosyls (Glc(2-1)Glc), R2 is OH, and R3 is a glucosyl, the compound of formula (I) is ginsenoside Rd;

when R1 is two glucosyls (Glc(2-1)Glc), R2 is OH, and both R3 and R4 are glucosyls, the compound of formula (II) is ginsenoside Rb1; or when R1 is two glucosyls (Glc(2-1) Glc), R2 is OH, R3 is a glucosyl, and R4 is a xylose group, the compound of formula (II) is ginsenoside Rb3;

when the R1 is H, R2 is OH, R3 is a glucosyl, and R4 is an arabinose group, the compound of the formula (II) is ginsenoside F3;

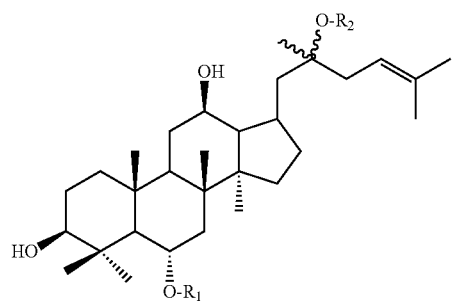

Compound of formula (III)

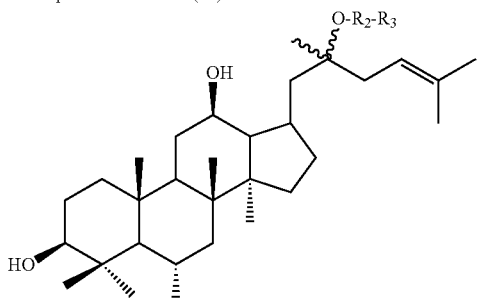

Compound of formula (IV)

Wherein, R1 is H, a glycosyl or polysaccharide glycosyl group, R2 is a glycosyl group, and R3 is a glycosyl group, and the polypeptide is selected from the group consisting of SEQ ID NOs.: 4 and a derivative polypeptide thereof.

In another preferred embodiment, the compound with the substitution of R1-R3 is shown in the following table:

| substrate | R1 | R2 | R3 | product |
|---|---|---|---|---|
| F1 | H | Glc | Glc | notoginsenoside U |
| Rg1 | Glc | Glc | Glc | notoginsenoside R3 | that is, when R1 is H, and R2 is a glycosyl, the compound of the formula (III) is ginsenoside F1 (F1);

when R1 is H, and both R2 and R3 are glycosyls, the compound of the formula (IV) is notoginsenoside U; when R1 and R2 are glycosyls, the compound of the formula (III) is ginsenoside Rg1 (Rg1); or when R1, R2 and R3 are glycosyl groups, the compound of the formula (IV) is notoginsenoside R3 (R3);

(C)

Compound of formula (V)

-continued

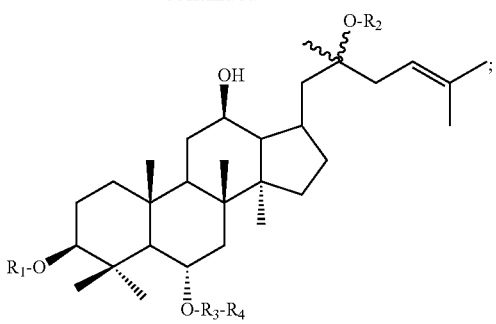

Compound of formula (VI)

wherein, R1 and R2 are H or glycosyls, and R3 and R4 are glycosyls; and the polypeptide is selected from the group consisting of SEQ ID NOs.: 12, 14, 16, 18, 20, 22, 24, 26, 28, 30 or a derivative polypeptide.

In another preferred embodiment, the compound with the substitution of R1-R4 is shown in the following table:

| substrate | R1 | R2 | R3 | R4 | product |
|---|---|---|---|---|---|
| Rg1 | H | Glc | Glc | Xyl | notoginsenoside R1 |
| Rg1 | H | Glc | Glc | Glc | 20-O-Glucosylginsenoside Rf |
| Rh1 | H | H | Glc | Xyl | notoginsenoside R2 |
| Rh1 | H | H | Glc | Glc | ginsenoside Rf | that is, when R1 is H, and both R2 and R3 are glucosyls, the compound of the formula is ginsenoside Rg1;

when R1 is H, R2 and R3 are glucosyls, and R4 is a xylose group, the compound of formula (VI) is notoginsenoside R1;

when R1 is H, R2 and R3 are glucosyls, and R4 is a glucosyl, the compound of formula (VI) is saponin 20-O-Glucosylginsenoside Rf;

when R1 and R2 are H, and R3 is a glucosyl, the compound of formula (V) is ginsenoside Rh1;

when R1 and R2 are H, R3 is a glucosyl, and R4 is a xylose group, the compound of the formula (VI) is notoginsenoside R2; when R1 and R2 are H, R3 and R4 are glucosyls, the compound of formula (VI) is ginsenoside Rf.

(D)

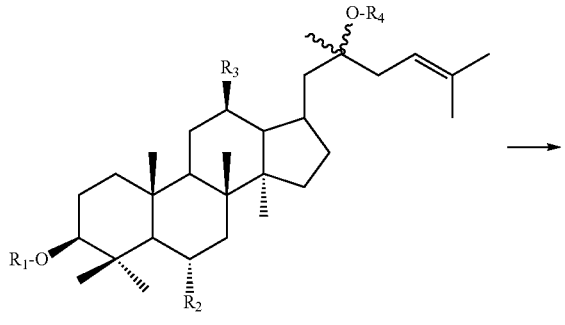

Compound of formula (VII)

-continued

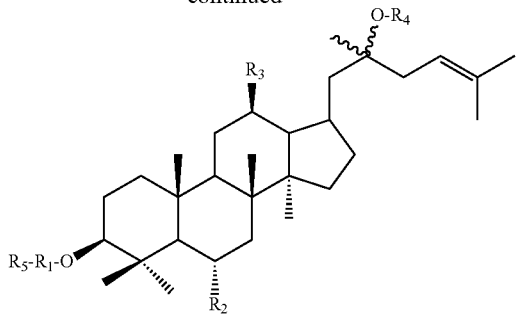

Compound of formula (VIII)

-continued

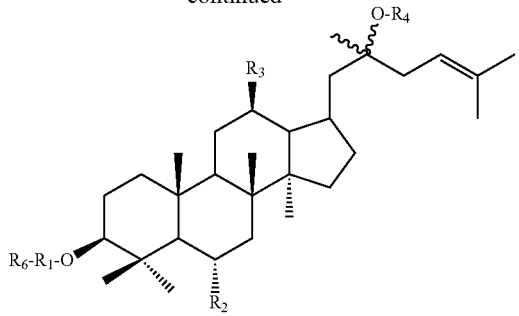

Compound of formula (X)

wherein, R1 is a glycosyl; R2 and R3 are OH or H; R4 is a glycosyl or H; R5 is a glycosyl, and R5-R1-0 is a first glycosyl-derived glycosyl at C3 position; and the polypeptide is selected from the group consisting of SEQ ID NOs.: 39, 41, 43, 45, 47, 49, 51, 53, 55, 57, 59, 98, 100, 116, 118, 120, 122, and 124 and a derivative polypeptide thereof;

the compound with the substitution of R1-R4 is shown in the following table:

| substrate | R1 | R2 | R3 | R4 | R5 | product |
|---|---|---|---|---|---|---|
| Rh2 | Glc | H | OH | H | Glc | Rg3 |
| F2 | Glc | H | OH | Glc | Glc | Rd |
| Gypenoside XVII | Glc | H | OH | Glc(6,1)Glc | Glc | Rb1 |
| Gypenoside IX | Glc | H | OH | Glc(6,1)xyl | Glc | Rb3 | that is, when R1 is a glucosyl; R2 is H, R3 is OH, R4 is H, and the compound of the formula (VII) is Rh2;

R1 is a glucosyl; R2 is H, R3 is OH, R4 is a glucosyl, and the compound of the formula (VII) is F2;

R1 is a glucosyl; R2 is H, R3 is OH, R4 is two glucosyls, and the compound of formula (VII) is Gypenoside XVII;

R1 is a glucosyl; R2 is H, R3 is OH, R4 is a glucosyl group with a xylosyl group extended, and the compound of formula (VII) is Gypenoside IX;

when the substrate of (VII) compound is Rh2, the product of formula (VIII) is Rg3; when the substrate of (VII) compound is F2, the product of formula (VIII) is Rd; when the substrate of (VII) compound is Gypenoside XVII, the product of formula (VIII) is Rb1; when the substrate of (VII) compound is Gypenoside IX, the product of formula (VIII) is Rb3.

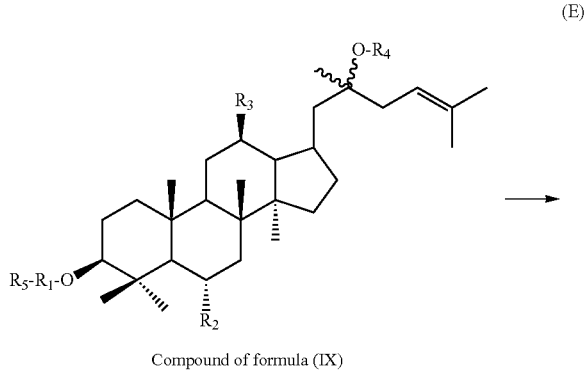

Compound of formula (IX)

wherein, R1 is a glycosyl; R2 and R3 are OH or H; R4 is a glycosyl or H; R5 is a glycosyl, R5-R1-0 is a derivative glycosyl from the first glycosyl on C3 position; and R6 is a glycosyl, R6-R1-0 is a derivative glycosyl from the first glycosyl on C3 position, and the polypeptide is selected from the group consisting of SEQ ID NOs.: 41, 45, 90, 92, 94 and 96 and a derivative polypeptide thereof;

R1 is two glucosyls, R2 is H, R3 is OH, R4 is H, and the compound of formula (IX) is Rg3.

R1 is two glucosyls, R2 is H, R3 is OH, R4 is a glucosyl, and the compound of formula (IX) is Rd.

In another preferred embodiment, the glycosyl is selected from the group consisting of: a glucosyl, a xylose group, a galacturonic acid group, a galactosyl, an arabinose group, a rhamnosyl, and other hexose and pentose groups.

In another preferred embodiment, the compounds of (I), (III), (V), (VII), (IX) in the reaction formula include, but are not limited to, dammarane tetracyclic triterpenoids in S or R configuration, lanostanes tetracyclic triterpenoids, apotirucallane tetracyclic triterpenoids, tirucallanes tetracyclic triterpenoids, cycloartanes (cycloaltine) tetracyclic triterpenoids, cucurbitane tetracyclic triterpenoids or meliacanes tetracyclic triterpenoid.

In another preferred embodiment, the compounds of (II), (IV), (VI), (VIII), or (X) in the reaction formula include ginsenoside Rg3, ginsenoside Rd, ginsenoside Rb1, ginsenoside Rb3, saponin DMGG, saponin DMGX, gypenoside LXXV, gypenoside XVII, gypenoside XIII, gypenoside IX, notoginsenoside U and, notoginsenoside R1, and notoginsenoside R2, notoginsenoside R3, 3-O-β-(D-xylopyranosyl)-β-(D-glucopyranos y1)-PPD; 3-O-β-(D-xylopyranosyl)-β-(D-glucopyranosyl)-CK, 20-O-Glucosylginsenoside Rf and Ginsenoside F3.

In a sixth aspect of the present invention, it provides a method for performing a glycosyl transfer catalytic reaction, comprising the steps of: performing a glycosyl transfer catalytic reaction in the presence of the polypeptide or a derivative polypeptide thereof according to the third aspect of the present invention.

In another preferred embodiment, the method further includes the steps:

in the presence of a glycosyl donor and a polypeptide and a derivative polypeptide thereof according to the third aspect of the present invention, converting the compound of formula (I) to the compound of formula (II), or converting the compound of formula (III) to the compound of formula (IV), or converting the compound of formula (V) to the compound of formula (VI); or converting the compound of formula (VII) to the compound of formula (VIII), or converting the compound (IX) to the compound of the formula (IX).

In another preferred embodiment, the method further comprises adding the polypeptide and the derivative polypeptide thereof to a catalytic reaction, respectively; and/or adding the polypeptide and the derivative polypeptide thereof simultaneously to a catalytic reaction.

In another preferred embodiment, the method further includes co-expressing a nucleotide sequence encoding a glycosyltransferase with a key gene in the anabolic pathway of dammarenediol and/or protopanoxadiol and/or protopanaxatriol in the host cell, thereby obtaining the compound of formula (II), (IV), (VI), (VIII), or (X).

In another preferred embodiment, the host cell is a yeast cell or an *E. coli* cell.

In another preferred embodiment, the polypeptide is a polypeptide having an amino acid sequence as shown in SEQ ID NOs.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124 or a derivative polypeptide thereof.

In another preferred embodiment, the nucleotide sequence encoding the polypeptide is as shown in SEQ ID NOs.: 3, 5, 7, 13, 15, 17, 19, 21, 23, 25, 27, 29, 38, 40, 42, 44, 46, 48, 50, 52, 54, 56, 58, 89, 91, 93, 95, 97, 99, 115, 117, 119, 121, or 123.

In another preferred embodiment, the method further includes: providing an additive for regulating the enzyme activity to the reaction system.

In another preferred embodiment, the additive for regulating enzyme activity is: an additive that increases enzyme activity or inhibits enzyme activity.

In another preferred embodiment, the additive for regulating the enzyme activity is selected from the group consisting of $Ca^{r}+$, $Co^{2}+$, $Mn^{2}+$, $Ba^{2}+$, $Al^{3}\pm$, $Ni^{2}+$, $Zn^{2}+$, and $Fe^{2}+$.

In another preferred embodiment, the additive for regulating the enzyme activity is a substance capable of generating $Ca^{r}+$, $Co^{2}+$, $Mn^{2}+$, $Ba^{2}+$, $Al^{3}\pm$, $Ni^{2}+$, $Zn^{2}+$, or $Fe^{2}+$.

In another preferred embodiment, the glycosyl donor is a nucleoside diphosphate saccharide selected from the group consisting of UDP-glucose, ADP-glucose, TDP-glucose, CDP-glucose, GDP-glucose, UDP-xylose, ADP-xylose, TDP-xylose, CDP-xylose, GDP-xylose, UDP-galacturonic acid, UDP-acetylglucose, ADP-acetylglucose, TDP-acetylglucose, CDP-acetylglucose, GDP-acetylglucose, ADP-galacturonic acid, TDP-galacturonic acid, CDP-galacturonic acid, GDP-galacturonic acid, UDP-galactose, ADP-galactose, TDP-galactose, CDP-galactose, GDP-galactose, UDP-arabinose, ADP-arabinose, TDP-arabinose, CDP-arabinose, GDP-arabinose, UDP-rhamnose, ADP-rhamnose, TDP-rhamnose, CDP-rhamnose, GDP-rhamnose, and other nucleoside diphosphate hexose and nucleoside diphosphate pentose, and a combination thereof. In another preferred embodiment, the glycosyl donor is a uridine diphosphate saccharide, selected from the group consisting of UDP-glucose, UDP-xylose, UDP-galacturonic acid, UDP-galactose, UDP-arabinose, UDP-rhamnose, and other uridine diphosphate hexose and uridine diphosphate pentose, and a combination thereof.

In another preferred embodiment, the pH of the reaction system is: pH 4.0-10.0, preferably pH 5.5-9.0.

In another preferred embodiment, the temperature of the reaction system is: 10° C.-105° C., preferably 20° C.-50° C.

In another preferred embodiment, the key genes in the dammarenediol anabolic pathway include (but are not limited to): a dammarenediol synthase gene.

In another preferred embodiment, the key genes in the ginsenoside CK anabolic pathway include (but are not limited to): a dammarenediol synthase gene, cytochrome P450 CYP716A47 gene, gene of reductase for P450 CYP716A47, and glycosyltransferase UGTPg1 at C20 position of tetracyclic triterpenes (Genbank accession number KF377585.1), and a combination thereof.

In another preferred embodiment, the key genes in the ginsenoside F1 anabolic pathway include (but are not limited to): a dammarenediol synthase gene, a cytochrome P450 CYP716A47 gene, a gene of reductase for P450 CYP716A47, a cytochrome P450 CYP716A53V2 gene and a gene of a reductase thereof and a glycosyltransferase UGTPg1 at C20 position of tetracyclic triterpene, and a combination thereof.

In another preferred example, the key genes in the ginsenoside Rg1 anabolic pathway include (but are not limited to): a dammarenediol synthase gene, a cytochrome P450 CYP716A47 gene, a gene of reductase for P450 CYP716A47, and glycosyltransferase UGTPg1 and UGTPg100 at C20 and C6 position of tetracyclic triterpenes (Genbank accession number AKQ76388.1), and a combination thereof.

In another preferred embodiment, the substrate of the glycosyl-catalyzed reaction is a compound of formula (I), (III), (V), (VII), (IX), and the products are compounds (II), (IV), (VI), (VIII), (X);

In another preferred embodiment, the compound of formula (I) is ginsenoside CK, and the compound of formula (II) is gypenosides DOW (20-O-β-(D-glucopyranosyl)-(β-(D-glucopyranosyl)-protopanaxadiol);

or, the compound of formula (I) is ginsenoside DMG, and the compound of formula (II) is a new ginsenoside DMGG (20-O-β-(D-glucopyranosyl)-β-(D-glucopyranosyl)-dammarenediol);

the compound of formula (I) is ginsenoside F2, and the compound of formula (II) is gypenosides XVII (3-O-β-(D-glucopyranosyl)-20-O-β-(D-glucopyranosyl)-β-(D-glucopyranosyl)-protopanaxadiol);

or, the compound of formula (I) is ginsenoside Rd, and the compound of formula (II) is ginsenoside Rb1 (3-O-β-(D-glucopyranosyl)-β-(D-glucopyranosyl)-20-O-β-(D-glucopyranosyl) β-(D-glucopyranosyl)-protopanaxadiol);

or, the compound of formula (I) is ginsenoside Rd, and the compound of formula (II) is ginsenoside Rb3 (3-O-β-(D-glucopyranosyl)-β-(D-glucopyranosyl)-20-O-β-(D-xylopyranosyl)-β-(D-glucopyranosyl)-protopanaxadiol);

the compound of formula (I) is ginsenoside CK, and the compound of formula (II) is gypenosides XIII;

the compound of formula (I) is ginsenoside DMG, and the compound of formula (II) is ginsenoside DMGX (20-O-β-(D-glucopyranosyl)-β-(D-glucopyranosyl)-dammarenediol);

the compound of formula (I) is ginsenoside F2, and the compound of formula (II) is gypenosides IX;

the compound of formula (I) is ginsenoside CK, and the compound of formula (II) is ginsenoside F3; in another preferred embodiment, the compound of formula (III) is ginsenoside F1, and the compound of formula (IV) is notoginsenoside U (20-O-β-(D-glucopyranosyl)-β-(D-glucopyranosyl)-protopanaxatriol);

In another preferred embodiment, the compound of formula (III) is ginsenoside Rg1, and the compound of formula (IV) is notoginsenoside R3;

In another preferred embodiment, the compound of formula (V) is ginsenoside Rg1, and the compound of formula (VI) is notoginsenoside R1 (6-O-β-(D-xylopyranosyl)-β-(D-glucopyranosyl)-20-O-β-(D-glucopyranosyl)-protopanaxatriol);

the compound of formula (V) is ginsenoside Rg1, and the compound of formula (VI) is 20-O-Glucosylginsenoside Rf;

the compound of formula (V) is ginsenoside Rh1, and the compound of formula (VI) is notoginsenoside R2 (6-O-β-(D-xylopyranosyl)-β-(D-glucopyranosyl)-protopanaxatriol).

Or, the compound of formula (V) is ginsenoside Rh1, and the compound of formula (VI) is ginsenoside Rf.

In another preferred embodiment, the compound of formula (III) is ginsenoside Rg1, and the compound of formula (IV) is notoginsenoside R3;

In another preferred embodiment, the compound of formula (VII) is Rh2, and the product of compound of formula (VIII) is Rg3;

the compound of formula (VII) is F2, and the product of compound of formula (VIII) is Rd;

the compound of formula (VII) is Gypenoside XVII, and the product of compound of formula (VIII) is Rb1;

the compound of formula (VII) is Gypenoside IX, and the product of compound of formula (VIII) is Rb3.

In another preferred embodiment, the compound of formula (IX) is Rg3, and the product of compound of formula (X) is 3-O-β-(D-xylopyranosyl)-β-(D-glucopyranosyl)-PPD;

the compound of formula (IX) is Rd, and the product of compound of formula (X) is 3-O-β-(D-xylopyranosyl)-β-(D-glucopyranosyl)-CK.

In a seventh aspect of the present invention, it provides a genetically engineered host cell containing the vector according to the fifth aspect of the present invention, or with a polynucleotide according to the fourth aspect of the present invention integrated into the gene thereof.

In another preferred embodiment, the cell is a prokaryotic cell or a eukaryotic cell.

In another preferred embodiment, the host cell is a eukaryotic cell, such as a yeast cell or a plant cell.

In another preferred embodiment, the host cell is a *Saccharomyces cerevisiae* cell.

In another preferred embodiment, the host cell is a prokaryotic cell, such as *E. coli*.

In another preferred embodiment, the host cell is a *Ginseng* cell.

In another preferred embodiment, the host cell is not a cell that naturally produces compounds of formula (II), (IV), (VI), (VII), or (X).

In another preferred embodiment, the host cell is not a cell that naturally produces ginsenoside Rg3, ginsenoside Rd, ginsenoside Rb1, ginsenoside Rb3, saponin DMGG, saponin DMGX, gypenosides LXXV, gypenosides XVII, gypenosides XIII, gypenosides IX, notoginsenoside U and notoginsenoside R1, notoginsenoside R2, notoginsenoside R3, 3-O-β-(D-xylopyranosyl)-β-(D-glucopyranosyl)-PPD; 3-O-β-(D-xylopyranosyl)-β-(D-glucopyranosyl)-CK, 20-O-Glucosylginsenoside Rf or Ginsenoside F3.

In another preferred embodiment, the key genes in the dammarene glycol anabolic pathway include (but are not limited to): a dammarene glycol synthase gene.

In another preferred example, the host cell contains key genes in the ginsenoside CK anabolic pathway including (but not limited to): a dammarene glycol synthase gene, a cytochrome P450 CYP716A47 gene, and a P450 CYP716A47 reductase gene and a glycosyltransferase UGTPg1 at the C20 site of the tetracyclic triterpene, or a combination thereof.

In another preferred example, the host cell contains key genes in the ginsenoside F1 anabolic pathway including (but not limited to): a dammarene glycol synthase gene, a cytochrome P450 CYP716A47 gene, and a reductase gene for P450 CYP716A47, a cytochrome P450 CYP716A53V2 gene and a glycosyltransferase UGTPg1 on the C20 site of the tetracyclic triterpene, or a combination thereof.

In another preferred example, the key genes in the ginsenoside Rg1 anabolic pathway include (but are not limited to): a dammarene glycol synthase gene, a cytochrome P450 CYP716A47 gene, a gene of a reductase for P450 CYP716A47, and glycosyltransferase UGTPg1 and UGTPg100 (Genbank accession number AKQ76388.1) on C20 and C6 of cyclotriterpenes, or a combination thereof.

In an eighth aspect of the present invention, it provides use of the host cell according to the seventh aspect of the present invention for preparing an enzyme catalytic reagent, or for producing a glycosyltransferase, or as a catalytic cell, or for producing formula (II), (IV), (VI), (VIII) or (X) compounds.

In a ninth aspect of the present invention, it provides a method for producing a transgenic plant, comprising the steps of: regenerating a genetically engineered host cell according to the seventh aspect of the present invention into a plant, and the genetically engineered host cell is a plant cell.

In another preferred embodiment, the genetically engineered host cell is a *Ginseng* cell.

In another preferred embodiment, the genetically engineered host cell is a *Panax notoginseng* cell.

It should be understood that, within the scope of the present invention, each technical feature of the present invention described above and in the following (as examples) may be combined with each other to form a new or preferred technical solution, which is not listed here due to space limitations.

DETAILED DESCRIPTION

Figure 1:
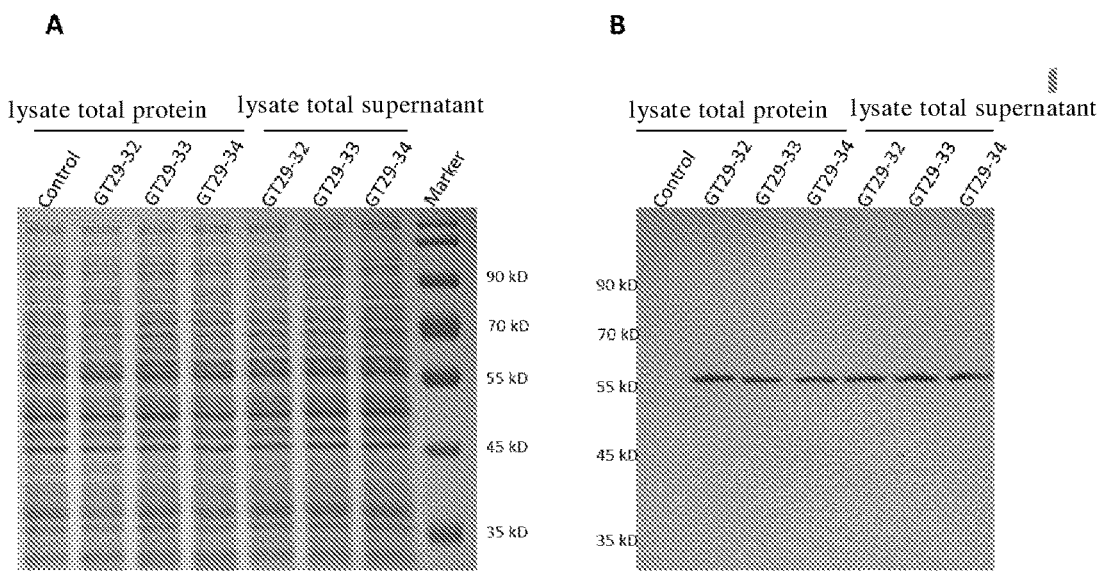
FIG. 1 (A) shows the expression shown by SDS-PAGE of glycosyltransferase genes GT29-32, GT29-33, and GT29-34 in *E. coli*; lane control represents total protein of lysate or lysis supernatant of empty vector recombinant pet28a; lane GT29-32 represents total protein or lysis supernatant of recombinant *E. coli* BL21-GT29-32; lane GT29-33 represents total protein or lysis supernatant of recombinant *E. coli* BL21-GT29-33; lane GT29-34 represents total protein of lysate or lysis supernatant of recombinant *E. coli* BL21-GT29-34; (B) shows the expression shown by Western Blot of glycosyltransferase genes GT29-32, GT29-33 and GT29-34 in *E. coli*; lane control represents total protein of lysate or lysis supernatant of empty vector recombinant pet28a; lane GT29-32 represents total protein of lysate or lysis supernatant of recombinant *E. coli* BL21-GT29-32; lane GT29-33 represents total protein of lysate or lysis supernatant of recombinant *E. coli* BL21-GT29-33; lane GT29-34 represents total protein of lysate or lysis supernatant of recombinant *E. coli* BL21-GT29-34.

After an extensive and in-depth study, the present inventors have firstly provided a new glycosyltransferase and the corresponding glycosyltransfer catalytic sites. Specifically, the glycosyltransferases GT29-32 (SEQ ID NO.: 4), GT29-33 (SEQ ID NO.: 6), GT29-34 (SEQ ID NO.: 8), GT29-4 (SEQ ID NO.: 12), GT29-5 (SEQ ID NO.: 14), GT29-7 (SEQ ID NO.: 16), GT29-9 (SEQ ID NO.: 18), GT29-11 (SEQ ID NO.: 20), GT29-13 (SEQ ID NO.: 22), GT29-17 (SEQ ID NO.: 24), GT29-18 (SEQ ID NO.: 26), GT29-19 (SEQ ID NO.: 116), GT29-20 (SEQ ID NO.: 118), GT29-21 (SEQ ID NO.:120), GT29-22 (SEQ ID NO.:122), GT29-23 (SEQ ID NO.:124)), GT29-24 (SEQ ID NO.: 28), GT29-25 (SEQ ID NO.: 30), GT29-36 (SEQ ID NO.: 90), GT29-37 (SEQ ID NO.: 92), GT29-42 (SEQ ID NO.: 94), GT29-43 (SEQ ID NO.: 96), GT29-45 (SEQ ID NO.: 98), GT29-46 (SEQ ID NO.: 100), PNUGT29-1 (SEQ ID NO.: 39), PNUGT29-2 (SEQ ID NO.: 41), PNUGT29-3 (SEQ ID NO.: 43), PNUGT29-4 ((SEQ ID NO.: 45), PNUGT29-5 (SEQ ID NO.: 47), PNUGT29-6 (SEQ ID NO.: 49), PNUGT29-7 (SEQ ID NO.: 51), PNUGT29-8 (SEQ ID NO.: 53), PNUGT29-9 (SEQ ID NO.: 55), PNUGT29-14 (SEQ ID NO.: 57), PNUGT29-15 (SEQ ID NO.: 59) can specifically and efficiently catalyze the hydroxyl glycosylation of the first glycosyl group on the C-20, C-6, or C3 position of a tetracyclic triterpene compound substrate or replace the original glycosyl group with a glycosyl group to extend the carbohydrate chain.

The glycosyltransferase of the present invention is particularly capable of converting ginsenosides CK, DMG, F2, Rd, Fl, Rhl, and Rg1 to ginsenoside Rg3, ginsenoside Rd, ginsenoside Rb1, ginsenoside Rb3, saponin DMGG, saponin DMGX, gypenosides LXXV, gypenosides XVII, gypenosides XIII, gypenosides IX, notoginsenoside U and notoginsenoside R1 and notoginsenoside R2, notoginsenoside R3, 3-O-β-(D-xylopyranosyl)-β-(D-glucopyranosyl)-PPD 3-O-β-(D-xylopyranosyl)-β-(D-glucopyranosyl)-CK, 20-O-Glucosylginsenoside Rf and Ginsenoside F3.

Definition

As used herein, the terms "active polypeptide", "polypeptide of the present invention and the derivative polypeptide thereof", "the enzyme of the present invention" and "glycosyltransferase" can be used interchangeably and all refer to GT29-32 (SEQ ID NO.: 4), GT29-33 (SEQ ID NO.: 6), GT29-34 (SEQ ID NO.: 8), GT29-4 (SEQ ID NO.: 12), GT29-5 (SEQ ID NO.: 14), GT29-7 (SEQ ID NO.: 16), GT29-9 (SEQ ID NO.: 18), GT29-11 (SEQ ID NO.: 20), GT29-13 (SEQ ID NO.: 22), GT29-17 (SEQ ID NO.: 24), GT29-18 (SEQ ID NO.: 26), GT29-19 (SEQ ID NO.: 116), GT29-20 (SEQ ID NO.: 118), GT29-21 (SEQ ID NO.:120), GT29-22 (SEQ ID NO.:122), GT29-23 (SEQ ID NO.:124), GT29-24 (SEQ ID NO.: 28), GT29-25 (SEQ ID NO.: 30), GT29-36 (SEQ ID NO.: 90), GT29-37 (SEQ ID NO.: 92), GT29-42 (SEQ ID NO.: 94), GT29-43 (SEQ ID NO.: 96), GT29-45 (SEQ ID NO.: 98), GT29-46 (SEQ ID NO.: 100), PNUGT29-1 (SEQ ID NO.: 39), PNUGT29-2 (SEQ ID NO.: 41), PNUGT29-3 (SEQ ID NO.: 43), PNUGT29-4 (SEQ ID NO.: 45), PNUGT29-5 (SEQ ID NO.: 47), PNUGT29-6 (SEQ ID NO.: 49), PNUGT29-7 (SEQ ID NO.: 51), PNUGT29-8 (SEQ ID NO.: 53), PNUGT29-9 (SEQ ID NO.: 55), PNUGT29-14 (SEQ ID NO.: 57), PNUGT29-15 (SEQ ID NO.: 59) polypeptides and the derivative polypeptides thereof.

As used herein, "the isolated polypeptide" or "active polypeptide" means that the polypeptide is substantially free of other proteins, lipids, carbohydrates, or other substances with which it is naturally associated. Those skilled in the art can purify the polypeptide using standard protein purification techniques. Substantially pure polypeptides can form a single main band on a non-reduced polyacrylamide gel. The purity of the polypeptide can be further analyzed using the amino acid sequence.

The active polypeptide of the present invention may be a recombinant polypeptide, a natural polypeptide, or a synthetic polypeptide. The polypeptides of the present invention may be naturally purified products or chemically synthesized products, or produced from prokaryotic or eukaryotic hosts (e.g., bacteria, yeast, plants) using recombinant techniques. Depending on the host used in the recombinant production protocol, the polypeptides of the present invention may be glycosylated or may be non-glycosylated. The polypeptides of the present invention may also include or exclude the starting methionine residue.

The present invention further provides fragments, derivatives and analogs of the polypeptides. As used herein, the terms "fragment", "derivative" and "analog" refer to a polypeptide that substantially retains the same biological function or activity of the polypeptide.

The polypeptide fragment, derivative or analog of the present invention may be (i) a polypeptide having one or more conservative or non-conservative amino acid residues substituted, and such substituted amino acid residues may or may not be encoded by the genetic code, or (ii) a polypeptide having a substituent group in one or more amino acid residues, or (iii) a polypeptide formed by fusion of a mature polypeptide with another compound, such as a compound that extends the half-life of the polypeptide, such as polyethylene glycol, or (iv) a polypeptide formed by fusing an additional amino acid sequence to this polypeptide sequence (such as a leader sequence or a secreted sequence or a sequence or protease sequence used to purify this polypeptide, or a fusion protein formed with an antigen IgG fragment). In accordance with the teachings herein, these fragments, derivatives, and analogs are within the scope of those skilled in the art.

The active polypeptide of the present invention has glycosyltransferase activity and can catalyze one or more of the following reactions:

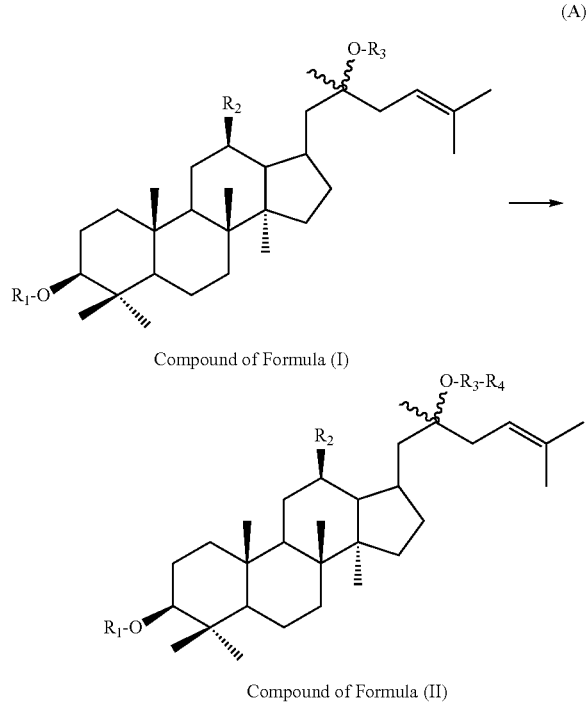

Compound of Formula (I)

Compound of Formula (II)

wherein R1 is H, a monosaccharide glycosyl or a polysaccharide glycosyl; R2 is H or OH; R3 is a monosaccharide glycosyl; R4 is a monosaccharide glycosyl, and the polypeptide is selected from SEQ ID NO: 4, 6, 8, 39, 41, 43, 45, 47, 49, 51, 53, 55, 57, 59, 98, 100, 116, 118, 120, 122, and 124 and a derivative polypeptide thereof.

In another preferred embodiment, the monosaccharide comprises glucose (Glc), rhamnose (Rha), acetylglucose (Glc(6)Ac), arabinofuranose (Araf), arabinopyranose (Arap), or xylose (Xyl) and the like.

In another preferred embodiment, the polysaccharide comprises Glc (2-1) Glc, Glc (6-1) Glc, Glc (6) Ac, Glc (2-1) Rha, Glc (6-1) Arap, Glc (6-1) Xyl, Glc (6-1) Araf, Glc (3-1) Glc (3-1), Glc (2-1) Glu (6) Ac, Glc (6-1) Arap (4-1) Xyl, Glc (6-1) Arap (2-1) Xyl, or Glc (6-1) Arap (3-1) Xyl and other polysaccharides composed of 2-4 monosaccharides.

The R1-R4 substituted compounds are shown in the table below:

| substrate | R1 | R2 | R3 | R4 | product |
|---|---|---|---|---|---|
| CK | H | OH | Glc | Glc | Gypenosides LXXV |
| DMG | H | H | Glc | Glc | DMGG |
| F2 | Glc | OH | Glc | Glc | Gypenosides XVII |
| Rd | Glc(2-1)Glc | OH | Glc | Glc | Rb1 |

-continued

| substrate | R1 | R2 | R3 | R4 | product |
|---|---|---|---|---|---|
| CK | H | OH | Glc | Xyl | Gypenosides XIII |
| DMG | H | H | Glc | Xyl | DMGX |
| F2 | Glc | OH | Glc | Xyl | Gypenosides IX |
| Rd | Glc(2-1)Glc | OH | Glc | Xyl | Rb3 |
| CK | H | OH | Glc | Arabinose | Ginsenoside F3 | that is, when R1 is H, R2 is OH, and R3 is a glucosyl, the compound of formula (I) is ginsenoside CK (CK);

when R1 and R2 are both H, and R3 is a glucosyl, the compound of Formula (I) is ginsenoside DMG;

when R1 is a glucosyl, R2 is OH, and R3 is a glucosyl, the compound of Formula (I) is ginsenoside F2 (F2); or compound of Formula (I) is ginsenoside Rd;

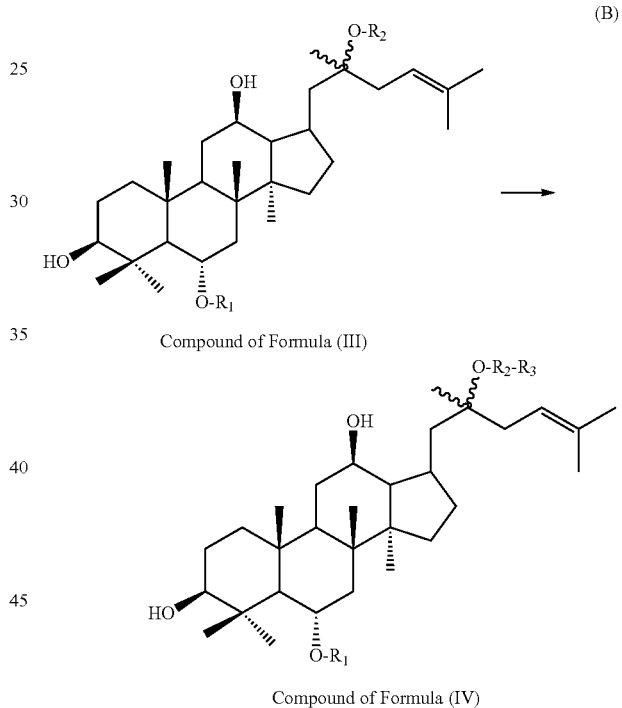

Compound of Formula (III)

Compound of Formula (IV)

wherein R1 is H, a glycosyl or a polysaccharide glycosyl, R2 is a glycosyl, R3 is a glycosyl, the polypeptide is selected from SEQ ID NOs.: 4 and a derivative polypeptide thereof;

The R1-R3 substituted compounds are shown in the table below:

| substrate | R1 | R2 | R3 | product |
|---|---|---|---|---|
| F1 | H | Glc | Glc | Notoginsenoside U |
| Rg1 | Glc | Glc | Glc | Notoginsenoside R3 | that is, when R1 is H and R2 is a glucosyl, the compound of Formula (III) is ginsenoside F1 (F1); or when R1 and R2 are glucosyls, the compound of Formula (III) is ginsenoside Rg1 (Rg1);

(C)

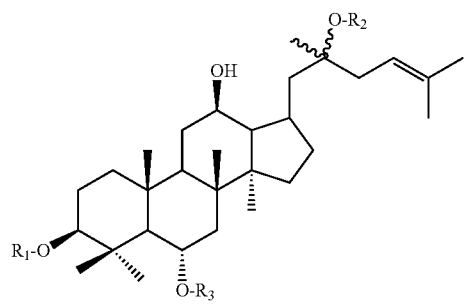

Compound of Formula (V)

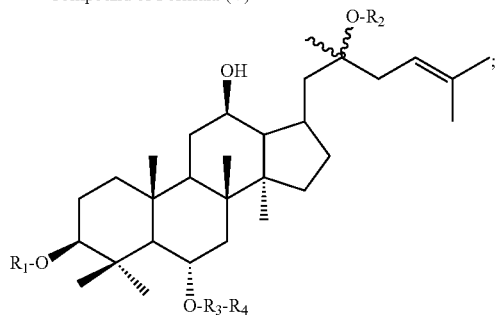

Compound of Formula (VI)

wherein R1 and R2 are H or glycosyls, and R3 and R4 are glycosyls. The polypeptide is selected from SEQ ID NOs.: 12, 14, 16, 18, 20, 22, 24, 26, 28, 30 or a derivative polypeptide thereof;

The R1-R4 substituted compounds are shown in the table below:

| substrate | R1 | R2 | R3 | R4 | product |
|---|---|---|---|---|---|
| Rg1 | H | Glc | Glc | Xyl | Notoginsenoside R1 |
| Rg1 | H | Glc | Glc | Glc | 20-O-Glucosylginsenoside Rf |
| Rh1 | H | H | Glc | Xyl | Notoginsenoside R2 |
| Rh1 | H | H | Glc | Glc | Ginsenoside Rf | that is, when R1 is H and both R2 and R3 are glucosyls, the compound of Formula (V) is ginsenoside Rg1;

when R1 and R2 are H, and R3 is glucosyl, the compound of Formula (V) is ginsenoside Rh1.

(D)

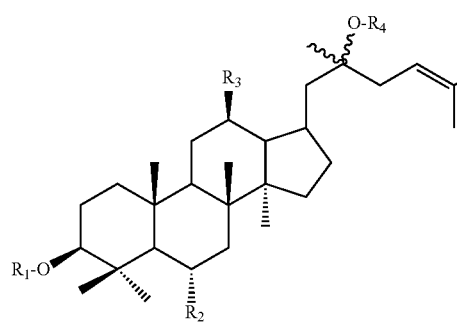

Compound of Formula (VII)

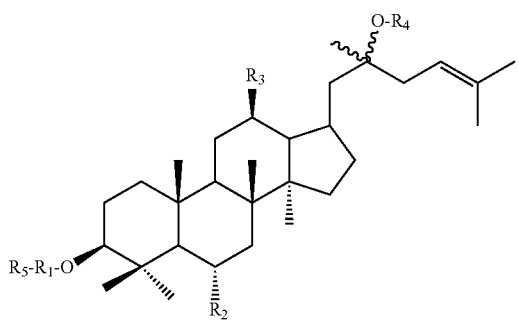

Compound of Formula (VIII)

wherein R1 is a glycosyl; R2 and R3 are OH or H; R4 is a glycosyl or H; R5 is a glycosyl, R5-R1-O is a glycosyl derived from the first glycosyl of C3; and the polypeptide is selected from SEQ ID NOs.: 26, 28, 30, 39, 41, 43, 45, 47, 49, 51, 53, 55, 57, 59, 98, 100, 116, 118, 120, 122, and 124 and a derivative polypeptide thereof;

| substrate | R1 | R2 | R3 | R4 | R5 | product |
|---|---|---|---|---|---|---|
| Rh2 | Glc | H | OH | H | Glc | Rg3 |
| F2 | Glc | H | OH | Glc | Glc | Rd |
| Gypenoside XVII | Glc | H | OH | Glc(6,1)Glc | Glc | Rb1 |
| Gypenoside IX | Glc | H | OH | Glc(6,1)xyl | Glc | Rb3 | that is, when R1 is a glucosyl; R2 is H, R3 is OH, R4 is H, and the compound of Formula (VII) is Rh2;

R1 is a glucosyl; R2 is H, R3 is OH, R4 is a glucosyl, and the compound of Formula (VII) is F2;

R1 is a glucosyl; R2 is H, R3 is OH, R4 is two glucosyl groups, and the compound of Formula (VII) is Gypenoside XVII;

R1 is a glucosyl; R2 is H, R3 is OH, R4 is a glucosyl extended with a xylose, the compound of Formula (VII) is Gypenoside IX;

(E)

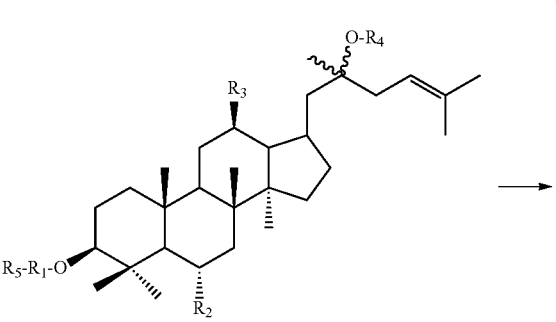

Compound of Formula (IX)

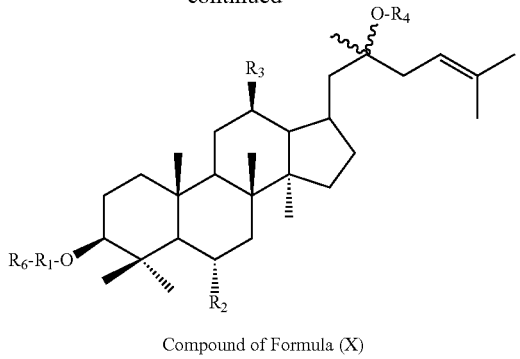

Compound of Formula (X)

wherein R1 is a glycosyl; R2 and R3 are OH or H; R4 is a glycosyl or H; R5 is a glycosyl and R5-R1-0 is a glycosyl derived from the first glycosyl of C3; R6 is a glycosyl and R6-R1-0 is a glycosyl derived from the first glycosyl of C3, and the polypeptide is selected from SEQ ID NOs.: 41, 45, 90, 92, 94, and 96 and a derivative polypeptide thereof;

R1 is two glucosyl groups, R2 is H, R3 is OH, R4 is H, and the compound of Formula (IX) is Rg3.

R1 is two glucosyl groups, R2 is H, R3 is OH, R4 is glucosyl, and the compound of Formula (IX) is Rd.

The preferred sequence of the polypeptide is as shown in SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124, and the term also includes polypeptide variants and the derived polypeptides that have the same function as the indicated polypeptides of SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124. These variant forms include (but are not limited to): one or more (usually 1-50, preferably 1-30, more preferably 1-20, most preferably 1-10) amino acid deletions, insertions and/or substitutions and the addition of one or several (usually within 20, preferably within 10, more preferably within 5) amino acids at the C-terminus and/or N-terminus. For example, in the art, the substitution of amino acids with similar or close properties usually does not change the function of the protein. As another example, adding one or several amino acids to the C-terminus and/or N-terminus usually does not change the function of the protein. The term also includes active fragments and active derivatives of the polypeptides of the present invention. The present invention also provides analogues of the polypeptides. The difference between these analogues and the natural polypeptide of the present invention may be a difference in amino acid sequence, a difference in the modification form that does not affect the sequence, or both. These polypeptides include natural or induced genetic variants. Induced variants can be obtained by various techniques, such as random mutagenesis by radiation or exposure to mutagen, or by site-directed mutagenesis or other known molecular biology techniques. Analogs also include analogs with residues different from natural L-amino acids (such as D-amino acids), and analogs with non-naturally occurring or synthetic amino acids (such as (3, y-amino acids). It should be understood that the polypeptide of the present invention is not limited to the representative polypeptides exemplified above.

Modified (usually without changing the primary structure) forms include: in vivo or in vitro chemically derived forms of the polypeptide such as acetylation or carboxylation. Modifications also include glycosylation, such as those produced by glycosylation modification during the synthesis and processing of polypeptides or during further processing steps. This modification can be accomplished by exposing the polypeptide to an enzyme that performs glycosylation (such as mammalian glycosylation or deglycosylation enzymes). Modified forms also include sequences with phosphorylated amino acid residues (e.g., phosphotyrosine, phosphoserine, phosphothreonine). Also included are peptides that have been modified to improve their proteolytic resistance or optimize their solubility.

The amino or carboxyl terminus of GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 or PNUGT29-15 protein of the present invention may also contain one or more polypeptide fragments as protein tags. Any suitable tags can be used in the present invention. For example, the tags may be FLAG, HA, HAI, c-Myc, Poly-His, Poly-Arg, Strep-TagII, AU1, EE, T7, 4A6, c, B, gE, and Tyl. These tags can be used to purify proteins. Table 1 lists some of the commercially available tags.

TABLE 1

| tag | number of residues |
| --- | --- |
| Poly-Arg | 5-6 (usually 5) |
| Poly-His | 2-10 (usually 6) |
| FLAG | 8 |
| Strep-TagII | 8 |
| C-myc | 10 |
| GST | 220 |

In order to make the translated protein secreted and expressed (such as secreted out of the cell), a signal peptide sequence, such as pelB signal peptide and the like can be added to the amino terminus of GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-9, PNUGT29-14 or PNUGT29-15. The signal peptide can be cleaved during the secretion of the polypeptide from the cell.

The polynucleotide of the present invention may be in the form of DNA or RNA. DNA form includes cDNA, genomic DNA, or synthetic DNA. DNA can be single-stranded or double-stranded. DNA can be a coding strand or a non-coding strand. The coding region sequence encoding the mature polypeptide can be the same with the coding region sequence as shown in SEQ ID NO.: 3, 5, 7, 11, 13, 15, 17, 19, 21, 23, 25, 27, 29, 38, 40, 42, 44, 46, 48, 50, 52, 54, 56, 58, 89, 91, 93, 95, 97, 99, 115, 117, 119, 121, or 123 or degenerate variants. As used herein, "degenerate variant" in the present invention refers to a nucleic acid sequence encoding the protein having SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124, but differing in the coding region sequences as shown in SEQ ID NO.: 3, 5, 7, 11, 13, 15, 17, 19, 21, 23, 25, 27, 29, 38, 40, 42, 44, 46, 48, 50, 52, 54, 56, 58, 89, 91, 93, 95, 97, 99, 115, 117, 119, 121, or 123, respectively.

Polynucleotides encoding mature polypeptides of SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124 include: coding sequences encoding mature polypeptides only; coding sequences encoding mature polypeptides and various additional coding sequences; mature polypeptide coding sequences (and optional additional coding sequences) and non-coding sequences.

The term "polynucleotide encoding a polypeptide" may include a polynucleotide encoding the polypeptide, or a polynucleotide further including additional coding and/or non-coding sequences.

The present invention also relates to variants of the aforementioned polynucleotides, which encode fragments, analogues and derivatives of polypeptides or polypeptides having the same amino acid sequence as the present invention. This polynucleotide variant may be a naturally occurring allelic variant or a non-naturally occurring variant. These nucleotide variants include substitution variants, deletion variants and insertion variants. As known in the art, an allelic variant is a form of substitution of a polynucleotide. It may be a substitution, deletion, or insertion of one or more nucleotides, but it will not substantially change the function of the polypeptide encoded.

The present invention also relates to polynucleotides that hybridize to the above-mentioned sequences and have at least 50%, preferably at least 70%, more preferably at least 80%, 85%, 90%, 95% identity between the two sequences. The present invention particularly relates to polynucleotides that can hybridize to the polynucleotides of the present invention under stringent conditions (or stringent conditions). In the present invention, "stringent conditions" means: (1) hybridization and elution at a lower ionic strength and higher temperature, such as 0.2×SSC, 0.1% SDS, 60° C.; or (2) added with denaturing agents during hybridization, such as 50% (v/v) formamide, 0.1% calf serum/0.1% Ficoll, 42° C., etc.; or (3) hybridization only when the identity between the two sequences is at least 90%, more preferably at least 95%. Furthermore, the polypeptides encoded by the hybridizable polynucleotides have the same biological function and activity as the mature polypeptides as shown in SEQ ID NO.: 4, 6, 8, 12, 14, 16, 18, 20, 22, 24, 26, 28, 30, 39, 41, 43, 45, 47, 49, 51, 53, 55, 57, 59, 90, 92, 94, 96, 98, 100, 116, 118, 120, 122, or 124.

The present invention also relates to a nucleic acid fragment hybridized to the aforementioned sequences. As used herein, "nucleic acid fragment" contains at least 15 nucleotides in length, preferably at least 30 nucleotides, more preferably at least 50 nucleotides, and most preferably at least 100 nucleotides or more. Nucleic acid fragments can be used in nucleic acid amplification techniques (such as PCR) to determine and/or isolate polynucleotides encoding GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 or PNUGT29-15 protein.

The polypeptide and polynucleotide in the present invention are preferably provided in an isolated form, and are more preferably purified to homogeneity.

A full-length nucleotide sequence or fragment thereof of GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-14 or PNUGT29-15 of the present invention can usually be obtained by PCR amplification method, recombination method or artificial synthesis method. For the PCR amplification method, primers can be designed according to the relevant nucleotide sequence disclosed in the present invention, especially the open reading frame sequence, and a commercially available cDNA library or cDNA library prepared according to conventional methods known to those skilled in the art is used as a 25 template to amplify and obtain the relevant sequences. When the sequence is long, it is often necessary to perform two or more PCR amplifications, and then splice the amplified fragments together in the correct order.

Once the relevant sequence is obtained, the relevant sequence can be obtained in large quantities by the recombination method. This is usually done by cloning it into a vector, then transferring it into cells, and then isolating and obtaining the relevant sequence from the proliferated host cells by conventional methods.

In addition, artificial synthetic methods can be used to synthesize the relevant sequences, especially when the length of the fragments is short. Generally, a long sequence can be obtained by synthesizing multiple small fragments and then connecting them.

At present, the DNA sequence encoding the protein (or fragment or derivative thereof) of the present invention can be obtained completely by chemical synthesis. This DNA sequence can then be introduced into various existing DNA molecules (or such as vectors) and cells known in the art. In addition, mutations can also be introduced into the protein sequence of the present invention by chemical synthesis.

The method of amplifying DNA/RNA using PCR technology is preferably used to obtain the gene of the present invention. Especially when it is difficult to obtain full-length cDNA from the library, the RACE method (RACE-cDNA terminal rapid amplification method) can be preferably used, and the primers used for PCR can be appropriately selected based on the sequence information of the present invention disclosed herein, and can be synthesized by conventional methods. The amplified DNA/RNA fragments can be separated and purified by conventional methods such as gel electrophoresis.

The present invention also relates to a vector comprising the polynucleotide of the present invention, and a host cell produced by genetic engineering using the vector of the present invention or the protein coding sequence of GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 or PNUGT29-15, and the method of producing the polypeptide of the present invention by recombinant technology.

Through the conventional recombinant DNA technology, the polynucleotide sequence of the present invention can be used to express or produce recombinant GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 or PNUGT29-15 polypeptide.

Generally speaking, there are the following steps:

(1) transforming or transducing a suitable host cell with a polynucleotide (or a variant) encoding a polypeptide of GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 or PNUGT29-15 of the present invention, or with a recombinant expression vector containing the polynucleotide;

(2). culturing a host cell in a suitable medium;

(3). isolating and purifing proteins from culture medium or cells.

In the present invention, polynucleotide sequences of GT29-32, GT29-33, GT29-34, GT29-4, GT29-5, GT29-7, GT29-9, GT29-11, GT29-13, GT29-17, GT29-18, GT29 19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-9, PNUGT29-14 or PNUGT29-15 can be inserted into recombinant expression vectors. The term "recombinant expression vector" refers to a bacterial plasmid, bacteriophage, a yeast plasmid, plant cell virus, mammalian cell virus such as adenovirus, retrovirus, or other vectors well known in the art. As long as it can replicate and stabilize in the host, any plasmid and vector can be used. An important feature of expression vectors is that they usually contain an origin of replication, a promoter, a marker gene and a translation control element.

Methods well known to those skilled in the art can be used to construct expression vectors containing GT29-32, GT29-33, GT29-34, GT29-4, GT29-5, GT29-7, GT29-9, GT29-11, GT29-13, GT29-17, GT29-18, GT29-19, GT29-20, GT29-21, GT29-22, GT29-23, GT29-24, GT29-25, GT29-32, GT29-33, GT29-34, GT29-36, GT29-37, GT29-42, GT29-43, GT29-45, GT29-46, PNUGT29-1, PNUGT29-2, PNUGT29-3, PNUGT29-4, PNUGT29-9, PNUGT29-14 or PNUGT29-15 encoding DNA sequences and appropriate transcription/translation control signals. These methods include in vitro recombinant DNA technology, DNA synthesis technology, in vivo recombinant technology and the like. The DNA sequence can be effectively linked to an appropriate promoter in an expression vector to guide mRNA synthesis. Representative examples of these promoters are: lac or trp promoters of *E. coli*; λ phage PL promoters; eukaryotic promoters including CMV immediate early promoters, HSV thymidine kinase promoters, early and late SV40 promoters, retroviral LTRs and other known promoters that control gene expression in prokaryotic or eukaryotic cells or their viruses. The expression vector also includes a ribosome binding site for translation initiation and a transcription terminator.

In addition, the expression vector preferably contains one or more selectable marker genes to provide phenotypic traits for selection of transformed host cells, such as dihydrofolate reductase, neomycin resistance, and green fluorescent protein (GFP) for eukaryotic cell culture, or tetracycline or ampicillin resistance for *E. coli*.

Vectors containing the appropriate DNA sequences and appropriate promoters or control sequences as described above can be used to transform appropriate host cells so that they can express proteins.

The host cell may be a prokaryotic cell, such as a bacterial cell; or a lower eukaryotic cell, such as a yeast cell; or a higher eukaryotic cell, such as a mammalian cell. Representative examples are: *E. coli, Streptomyces*; bacterial cells of *Salmonella typhimurium*; fungal cells such as yeast; plant cells; insect cells of *Drosophila* S2 or Sf9; animal cells such as CHO, COS, 293 cells, or Bowes melanoma cells and the like.

When the polynucleotide of the present invention is expressed in higher eukaryotic cells, if an enhancer sequence is inserted into the vector, transcription will be enhanced. Enhancers are cis-acting factors of DNA, usually about 10 to 300 base pairs, which act on the promoter to enhance gene transcription. Examples include 100 to 270 base pair of SV40 enhancers on the late side of the replication start point, polyoma enhancers on the late side of the replication start point, and adenovirus enhancers.

Those of ordinary skill in the art know how to select appropriate vectors, promoters, enhancers and host cells.

Transformation of host cells with recombinant DNA can be performed using conventional techniques well known to those skilled in the art. When the host is a prokaryotic organism such as *E. coli*, competent cells that can absorb DNA can be harvested after the exponential growth phase and treated with the $CaCl_2$) method. The procedures used are well known in the art. Another method is to use $MgCl_2$. If necessary, transformation can also be carried out by electroporation. When the host is a eukaryote, the following DNA transfection methods can be used: calcium phosphate co-precipitation method, conventional mechanical methods such as microinjection, electroporation, liposome packaging, etc.

The obtained transformant can be cultured by a conventional method and express the polypeptide encoded by the gene of the present invention. Depending on the host cell used, the medium used in the culture can be selected from various conventional mediums. The cultivation is carried out under conditions suitable for the growth of host cells. When the host cell grows to an appropriate cell density, the selected promoter is induced by an appropriate method (such as temperature conversion or chemical induction), and the cell is cultured for a period of time.

The recombinant polypeptide in the above method may be expressed in a cell, on a cell membrane, or secreted out of the cell. If necessary, the recombinant protein can be isolated and purified by various separation methods using its physical, chemical and other characteristics. These methods are well known to those skilled in the art. Examples of these methods include, but are not limited to: conventional renaturation treatment, treatment with protein precipitation agent (salting out method), centrifugation, bacteria disruption through osmosis, ultra-treatment, ultra-centrifugation, molecular sieve chromatography (gel filtration), adsorption chromatography, ion exchange chromatography, high performance liquid chromatography (HPLC) and various other liquid chromatography techniques and combinations of these methods.

Use

The active polypeptide or glycosyltransferase involved in the present invention can be used to artificially synthesize known ginsenosides and new ginsenosides and the derivatives thereof, and can convert CK, DMG, F2, Rd, Fl, Rhl and Rg1 into ginsenoside Rg3, ginsenoside Rd, ginsenoside Rb1, ginsenoside Rb3, saponin DMGG, saponin DMGX, Gypenosides DOW, Gypenosides XVII, Gypenosides XIII, Gypenosides IX, notoginsenoside U and, notoginsenoside R1, and notoginsenoside R2, notoginsenoside R3, 3-O-β-(D-xylopyranosyl)-β-(D-glucopyranosyl)-PPD; (D-xylopyranosyl)-β-(D-glucopyranosyl)-CK, 20-O-Glucosylginsenoside Rf and Ginsenoside F3.

The main advantages of the invention:

(1) The glycosyltransferase of the present invention can specifically and efficiently transfer a glycosyl or replace a glycosyl on the first glycosyl on the C-20 position/or the first glycosyl on the C-6 or C-3 position of the substrate of the tetracyclic triterpene compound to extend the carbohydrate chain;

(2) The glycosyltransferase of the present invention is particularly capable of converting CK, DMG, F2, Rd, F1, Rh1 and Rg1 into active ginsenoside Rg3, ginsenoside Rd, ginsenoside Rb1, ginsenoside Rb3, saponin DMGG, Saponin DMGX, Gypenosides DOW, Gypenosides XVII, Gypenosides XIII, Gypenosides IX, notoginsenoside U, notoginsenoside R1, and notoginsenoside R2, notoginsenoside R3, 3-O-β-(D-xylopyranosyl)-β-(D-glucopyranosyl)-PPD; 3-O-β-(D-xylopyranosyl)-β-(D-glucopyranosyl)-CK, 20-O-Glucosylginsenoside Rf and Ginsenoside F3.

(3) Ginsenoside Rb1 has the effect of protecting nerve cells and anti-inflammatory and antioxidant; and ginsenoside Rb3 has the effect of alleviating myocardial ischemia and anti-depression. Notoginsenoside R1 is the main active ingredient of notoginsenoside with anti-inflammatory effects. Notoginsenoside R2 has a neuroprotective effect.

Example 1 Isolation of *Ginseng* Glycosyltransferase and the Coding Gene Thereof

*Ginseng* RNA was extracted and reverse transcription was performed to obtain *Ginseng* cDNA. PCR amplification was performed using primer pair 1 (SEQ ID NO.: 1 and SEQ ID NO.: 2) or primer pair 2 (SEQ ID NO.: 9 and SEQ ID NO.: 10) or primer pair 3 (SEQ ID NO.: 113 and SEQ ID NO.: 114) using this cDNA as a template to obtain a 1.4-1.5 kb amplification product. The high-fidelity KOD DNA polymerase from Bao Bioengineering Co., Ltd. was used as the DNA polymerase. PCR products were detected by agarose gel electrophoresis.

The target DNA band was cut off under UV irradiation. Then the Axygen Gel Extraction Kit (AEYGEN) was used to recover DNA from the agarose gel, that is, the amplified DNA fragment. After A was added at the end of this DNA fragment using rTaq DNA polymerase from Bao Bioengineering Co., Ltd., it was ligated with the commercially available cloning vector pMD18-T Vector, and the ligation product was transformed into commercially available *E. coli* EPI300 competent cells. The transformed *E. coli* solution was coated on LB plates supplemented with AMP 50 ug/mL, IPTG 0.5 mM, X-Gal 25 μg/mL, and the recombinant clone was further verified by PCR and enzyme digestion. Several clones were selected and the recombinant plasmids were extracted and sequenced to obtain 29 different nucleic acid sequences, named GT29-32 (SEQ ID NO.: 3), GT29-33 (SEQ ID NO.: 5), GT29-34 (SEQ ID NO.: 7), GT29-4 (SEQ ID NO.: 11), GT29-5 (SEQ ID NO.: 13), GT29-7 (SEQ ID NO.: 15), GT29-9 (SEQ ID NO.: 17), GT29-11 (SEQ ID NO.: 19), GT29-13 (SEQ ID NO.: 21), GT29-17 (SEQ ID NO.: 23), GT29-18 (SEQ ID NO.: 25), GT29-19 (SEQ ID NO.: 116), GT29-20 (SEQ ID NO.: 118), GT29-21 (SEQ ID NO.: 120), GT29-22 (SEQ ID NO.: 122)), GT29-23 (SEQ ID NO.: 124), GT29-24 (SEQ ID NO.: 27), GT29-25 (SEQ ID NO.: 29), GT29-36 (SEQ ID NO.: 89), GT29-37 (SEQ ID NO.: 91), GT29-42 (SEQ ID NO.: 93), GT29-42 (SEQ ID NO.: 95), GT29-45 (SEQ ID NO.: 97) and GT29-46 (SEQ ID NO.: 99), respectively. Using BESTORF software to find ORF. Through sequence alignment, it was found that the extension products all have the conserved functional domain of glycosyltransferase family 1, indicating that it is a glycosyltransferase gene.

GT29-32: The glycosyltransferase gene GT29-32 encodes a protein GT29-32 containing 442 amino acids and has the amino acid sequence as shown in SEQ ID NO: 4 in the sequence listing. The theoretical molecular weight of this protein is predicted to be 49.2 kDa by software, and the isoelectric point pI is 6.09. The amino acid sequence identity between the glycosyltransferase and the functionally identified glycosyltransferase UGTPg29 (Genbank accession AKA44579.1) is 92%.

GT29-33: The glycosyltransferase gene GT29-33 encodes a protein GT29-33 containing 448 amino acids with the amino acid sequence as shown in SEQ ID NO: 6 in the sequence listing. The theoretical molecular weight of the protein is predicted to be 50.0 kDa by software, and the isoelectric point pI is 6.77. The amino acid sequence identity between the glycosyltransferase and the functionally identified glycosyltransferase UGTPg29 is 90%.

GT29-34: The glycosyltransferase gene GT29-34 encodes a protein GT29-34 containing 446 amino acids and has the amino acid sequence as shown in SEQ ID NO: 8 in the sequence listing. The theoretical molecular weight of the protein is predicted to be 49.7 kDa by software, and the isoelectric point pI is 6.23. The amino acid sequence identity between the glycosyltransferase and the functionally identified glycosyltransferase UGTPg29 is 90%.

GT29-4: The glycosyltransferase gene GT29-4 encodes a protein GT29-4 containing 446 amino acids with the amino acid sequence as shown in SEQ ID NO: 12 in the sequence listing. The theoretical molecular weight of the protein is predicted to be 49.8 kDa by software, and the isoelectric point pI is 5.63. The amino acid sequence identity between the glycosyltransferase and the functionally identified glycosyltransferase UGTPg29 is 92%.

GT29-5: The glycosyltransferase gene GT29-5 encodes a protein GT29-5 containing 446 amino acids with the amino acid sequence as shown in SEQ ID NO: 14 in the sequence listing. The theoretical molecular weight of the protein is predicted to be 49.7 kDa by software, and the isoelectric point pI is 5.93. The amino acid sequence identity between the glycosyltransferase and the functionally identified glycosyltransferase UGTPg29 is 93%.

GT29-7: The glycosyltransferase gene GT29-7 encodes protein GT29-7 containing 446 amino acids with the amino acid sequence as shown in SEQ ID NO: 16 in the sequence listing. The theoretical molecular weight of the protein is predicted to be 49.8 kDa by software, and the isoelectric point pI is 5.8. The amino acid sequence identity between the glycosyltransferase and the functionally identified glycosyltransferase UGTPg29 is 92%.

GT29-9: The glycosyltransferase gene GT29-9 encodes a protein GT29-9 containing 446 amino acids with the amino acid sequence as shown in SEQ ID NO: 18 in the sequence listing. The theoretical molecular weight of this protein is predicted to be 49.8 kDa by software, and the isoelectric point pI is 5.93. The amino acid sequence identity between the glycosyltransferase and the functionally identified glycosyltransferase UGTPg29 is 92%.

GT29-11: The glycosyltransferase gene GT29-11 encodes a protein GT29-11 containing 446 amino acids with the amino acid sequence as shown in SEQ ID NO: 20 in the sequence listing. The theoretical molecular weight of the protein is predicted to be 49.9 kDa by software, and the isoelectric point pI is 5.90. The amino acid sequence identity between the glycosyltransferase and the functionally identified glycosyltransferase UGTPg29 is 91%.

GT29-13: The glycosyltransferase gene GT29-13 encodes a protein GT29-13 containing 446 amino acids with the amino acid sequence as shown in SEQ ID NO: 22 in the sequence listing. The theoretical molecular weight of the protein is predicted to be 49.9 kDa by software, and the isoelectric point pI is 5.93.

The amino acid sequence identity between the glycosyltransferase and the functionally identified glycosyltransferase UGTPg29 is 91%.

GT29-17: The glycosyltransferase gene GT29-17 encodes a protein GT29-17 containing 442 amino acids with the amino acid sequence as shown in SEQ ID NO: 24 in the sequence listing. The theoretical molecular weight of the protein is predicted to be 49.3 kDa by software, and the isoelectric point pI is 5.35. The amino acid sequence identity between the glycosyltransferase and the functionally identified glycosyltransferase UGTPg29 is 93%.

GT29-18: The glycosyltransferase gene GT29-18 encodes a protein GT29-18 containing 446 amino acids with the amino acid sequence as shown in SEQ ID NO: 26 in the sequence listing. The theoretical molecular weight of the protein is predicted to be 49.9 kDa by software, and the isoelectric point pI is 5.93. The amino acid sequence identity between the glycosyltransferase and the functionally identified glycosyltransferase UGTPg29 is 91%.

GT29-24: The glycosyltransferase gene GT29-24 encodes a protein GT29-24 containing 446 amino acids with the amino acid sequence as shown in SEQ ID NO: 28 in the sequence listing. The theoretical molecular weight of the protein is predicted to be 49.9 kDa by software, and the isoelectric point pI is 5.93. The amino acid sequence identity between the glycosyltransferase and the functionally identified glycosyltransferase UGTPg29 is 91%.

GT29-25: The glycosyltransferase gene GT29-25 encodes a protein GT29-25 containing 446 amino acids with the amino acid sequence as shown in SEQ ID NO: 30 in the sequence listing. The theoretical molecular weight of the protein is predicted to be 49.9 kDa by software, and the isoelectric point pI is 5.93. The amino acid sequence identity between the glycosyltransferase and the functionally identified glycosyltransferase UGTPg29 is 91%.

GT29-19: The glycosyltransferase gene GT29-19 encodes a protein GT29-19 containing 442 amino acids with the amino acid sequence as shown in SEQ ID NO: 116 in the sequence listing. The theoretical molecular weight of the protein is predicted to be 49.1 kDa by software, and the isoelectric point pI is 5.47.

GT29-20: The glycosyltransferase gene GT29-20 encodes a protein GT29-20 containing 442 amino acids with the amino acid sequence as shown in SEQ ID NO: 118 in the sequence listing. The theoretical molecular weight of the protein is predicted to be 49.1 kDa by software, and the isoelectric point pI is 5.93.

GT29-21: The glycosyltransferase gene GT29-21 encodes a protein GT29-21 containing 442 amino acids with the amino acid sequence as shown in SEQ ID NO: 120 in the sequence listing. The theoretical molecular weight of the protein is predicted to be 49.1 kDa by software, and the isoelectric point pI is 5.80.

GT29-22: The glycosyltransferase gene GT29-22 encodes a protein GT29-22 containing 442 amino acids with the amino acid sequence as shown in SEQ ID NO: 122 in the sequence listing. The theoretical molecular weight of the protein is predicted to be 49.1 kDa by software, and the isoelectric point pI is 5.93.

GT29-23: The glycosyltransferase gene GT29-23 encodes a protein GT29-23 containing 442 amino acids with the amino acid sequence as shown in SEQ ID NO: 124 in the sequence listing. The theoretical molecular weight of the protein is predicted to be 49.0 kDa by software, and the isoelectric point pI is 5.61.

GT29-36: The glycosyltransferase gene GT29-36 encodes a protein GT29-36 containing 442 amino acids with the amino acid sequence as shown in SEQ ID NO:102 in the sequence listing. The theoretical molecular weight of the protein is predicted to be 49.1 kDa by software, and the isoelectric point pI is 5.93.

GT29-37: The glycosyltransferase gene GT29-37 encodes a protein GT29-37 containing 442 amino acids with the amino acid sequence as shown in SEQ ID NO: 104 in the sequence listing. The theoretical molecular weight of the protein is predicted to be 49.1 kDa by software, and the isoelectric point pI is 5.62.

GT29-42: The glycosyltransferase gene GT29-42 encodes a GT29-42 protein containing 444 amino acids with the amino acid sequence as shown in SEQ ID NO: 106 in the sequence listing. The theoretical molecular weight of the protein is predicted to be 49.4 kDa by software, and the isoelectric point pI is 6.16.

GT29-43: The glycosyltransferase gene GT29-43 encodes a protein GT29-43 containing 442 amino acids with the amino acid sequence as shown in SEQ ID NO: 108 in the sequence listing. The theoretical molecular weight of the protein is predicted to be 49.1 kDa by software, and the isoelectric point pI is 5.78.

GT29-45: The glycosyltransferase gene GT29-45 encodes a protein GT29-45 containing 448 amino acids with the amino acid sequence as shown in SEQ ID NO: 110 in the sequence listing. The theoretical molecular weight of the protein is predicted to be 50.0 kDa by software, and the isoelectric point pI is 7.25.

GT29-46: The glycosyltransferase gene GT29-46 encodes a protein GT29-46 containing 442 amino acids with the amino acid sequence as shown in SEQ ID NO: 112 in the sequence listing. The theoretical molecular weight of this protein is predicted to be 49.1 kDa by software, and the isoelectric point pI is 5.48.

Example 2 Expression of Glycosyltransferase Genes GT29-32, GT29-33 and GT29-34 in *E. coli*

Using the plasmids GT29-32-pMD18T, GT29-33-pMD18T and GT29-34-pMD18T constructed in Example 1 containing GT29-32, GT29-33 and GT29-34 genes as templates, the target genes GT29-32, GT29-33 and GT29-34 were amplified with the primers as shown in Table 1.

After the expression vector pET28a (purchased from Merck) was digested with NcoI/SalI, GT29-32, GT29-33 and GT29-34 were cloned into pET28a (one-step cloning kit, purchased from Novizan) to construct *E. coli* expression vectors GT29-32-pET28a, GT29-33-pET28a and GT29-34-pET28a. Using the 6×His tag sequence on pET28a, the C-terminus of the recombinant proteins GT29-32, GT29-33 and GT29-34 had a 6×His tag. The plasmids were transformed into commercially available *E. coli* BL21 to construct recombinant strains BL21-GT29-32, BL21-GT29-33 and BL21-GT29-34. A recombinant was inoculated into LB medium, cultured at 37° C., 200 rpm to an OD600 of about 0.6-0.8, then the bacterial solution was cooled to 4° C., and IPTG with a final concentration of 100 μM was added, and the expression was induced at 18° C., 120 rpm for 16 h. The bacteria was collected by centrifugation at 4° C., and the cells were disrupted by ultrasound. The supernatant of the cell lysate was collected by centrifugation at 12000 g, at 4° C. for 10 min. The samples were taken for SDS-PAGE electrophoresis and western blot. SDS-PAGE result shows that the recombinant transformants of GT29-32-pET28a, GT29-33-pET28a and GT29-34-pET28a are not significantly different from the cell lysate of the empty vector pET28a recombinant transformant, and the soluble expression is not obvious (FIG. 1A). Anti-6×His tag Western Blot (FIG. 1B) shows that there is a clear band between 45 and 55 kD, and the glycosyltransferases GT29-32, GT29-33, and GT29-34 are slightly solubly expressed in E. coli.

TABLE 1 primers used to amplify genes

| gene | primer | SEQ ID NO. |
|---|---|---|
| UGT29-4 | UGT29-4-F | 31 |
|  | UGT29-4-R | 34 |
| UGT29-5 | UGT29-5-F | 33 |
|  | UGT29-5-R | 32 |
| UGT29-7 | UGT29-7-F | 35 |
|  | UGT29-7-R | 32 |
| UGT29-9 | UGT29-9-F | 33 |
|  | UGT29-9-R | 32 |
| UGT29-11 | UGT29-11-F | 33 |
|  | UGT29-11-R | 32 |
| UGT29-13 | UGT29-13-F | 33 |
|  | UGT29-13-R | 32 |
| UGT29-17 | UGT29-17-F | 31 |
|  | UGT29-17-R | 32 |
| UGT29-18 | UGT29-18-F | 33 |
|  | UGT29-18-R | 34 |
| UGT29-24 | UGT29-24-F | 33 |
|  | UGT29-24-R | 34 |
| UGT29-25 | UGT29-25-F | 33 |
|  | UGT29-25-R | 32 |
| UGT29-32 | UGT29-32-F | 31 |
|  | UGT29-32-R | 32 |
| UGT29-33 | UGT29-33-F | 36 |
|  | UGT29-33-R | 37 |
| UGT29-34 | UGT29-34-F | 36 |
|  | UGT29-34-R | 34 |
| UGT29-19 | UGT29-19-F | 125 |
|  | UGT29-19-R | 126 |
| UGT29-20 | UGT29-20-F | 127 |
|  | UGT29-20-R | 128 |
| UGT29-21 | UGT29-21-F | 129 |
|  | UGT29-21-R | 130 |
| UGT29-22 | UGT29-22-F | 131 |
|  | UGT29-22-R | 132 |
| UGT29-23 | UGT29-23-F | 133 |
|  | UGT29-23-R | 134 |
| UGT29-36 | UGT29-36-F | 101 |
|  | UGT29-36-R | 102 |
| UGT29-37 | UGT29-37-F | 103 |
|  | UGT29-37-R | 104 |
| UGT29-42 | UGT29-42-F | 105 |
|  | UGT29-42-R | 106 |
| UGT29-43 | UGT29-43-F | 107 |
|  | UGT29-43-R | 108 |
| UGT29-45 | UGT29-36-F | 109 |
|  | UGT29-36-R | 110 |
| UGT29-46 | UGT29-36-F | 111 |
|  | UGT29-36-R | 112 |

Example 3 In Vitro Transglycosylation Activity and Product Identification of GT29-32, GT29-33 and GT29-34

The cell lysate supernatants of recombinant E. coli BL21-GT29-32, BL21-GT29-33 and BL21-GT29-34 in Example 2 was used as a crude enzyme solution to perform transglycosylation reaction, and the cell lysate of the recombinant E. coli with empty vector pET28a was used as a control.

Figure 2:
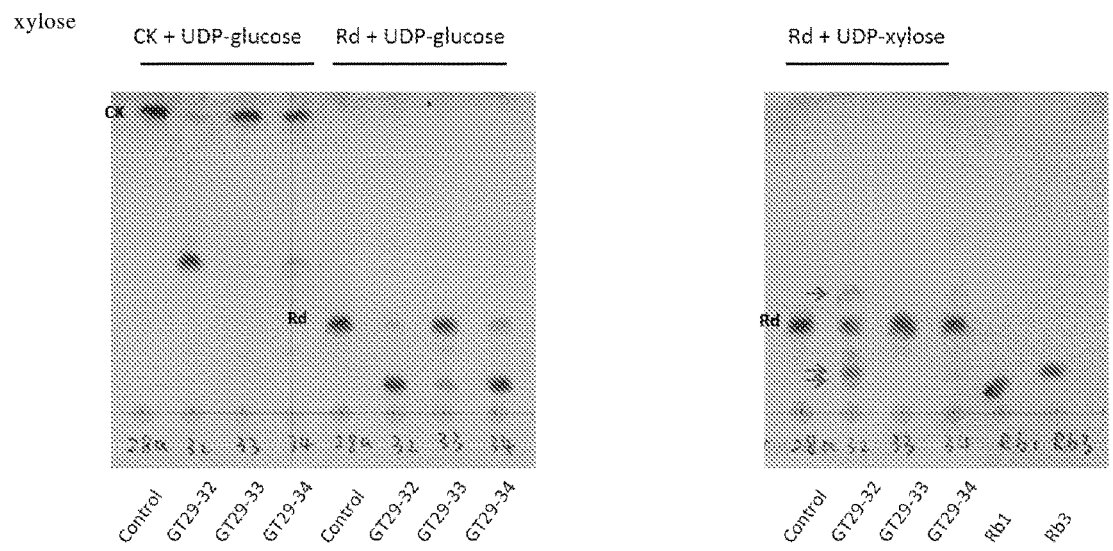
FIG. 2 shows a TLC pattern of a transglycosyl reaction catalyzed by glycosyltransferases GT29-32, GT29-33 and GT29-34 with ginsenoside CK or Rd as a glycosyl acceptor and UDP-glucose or UDP-xylose as a glycosyl donor. Control represents the lysate supernatant of the pet28a empty vector recombinant as an enzyme solution; GT29-32, GT29-33 and GT29-34 respectively represent the lysate supernatants of recombinant *E. coli* BL21-GT29-32, BL21-GT29-33 and BL21-GT29-34 as an enzyme solution.
Figure 3:
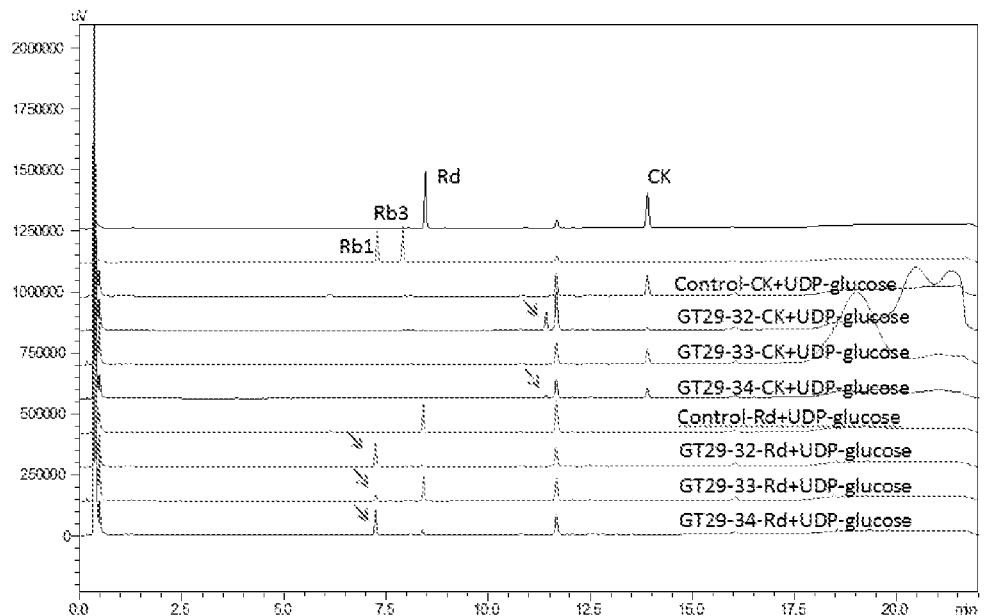
FIG. 3 shows an HPLC pattern of a transglycosyl reaction catalyzed by glycosyltransferases GT29-32, GT29-33 and GT29-34 with ginsenoside CK or Rd as a glycosyl acceptor and UDP-glucose as a glycosyl donor. Control represents the lysate supernatant of the pet28a empty vector recombinant as an enzyme solution; GT29-32, GT29-33 and GT29-34 respectively represent the lysate supernatants of recombinant E. coli BL21-GT29-32, BL21-GT29-33 and BL21-GT29-34 as an enzyme solution.

As shown in FIG. 2: using protopanaxadiol ginsenoside CK as a glycosyl receptor and UDP-glucose as a glycosyl donor, GT29-32 and GT29-34 can catalyze the formation of a new product;

As shown in FIG. 3: using ginsenoside Rd as a glycosyl acceptor and UDP-glucose as a glycosyl donor, GT29-32, GT29-33 and GT29-34 can catalyze the formation of Rb1. The HPLC results are consistent with the TLC results.

Figure 4:
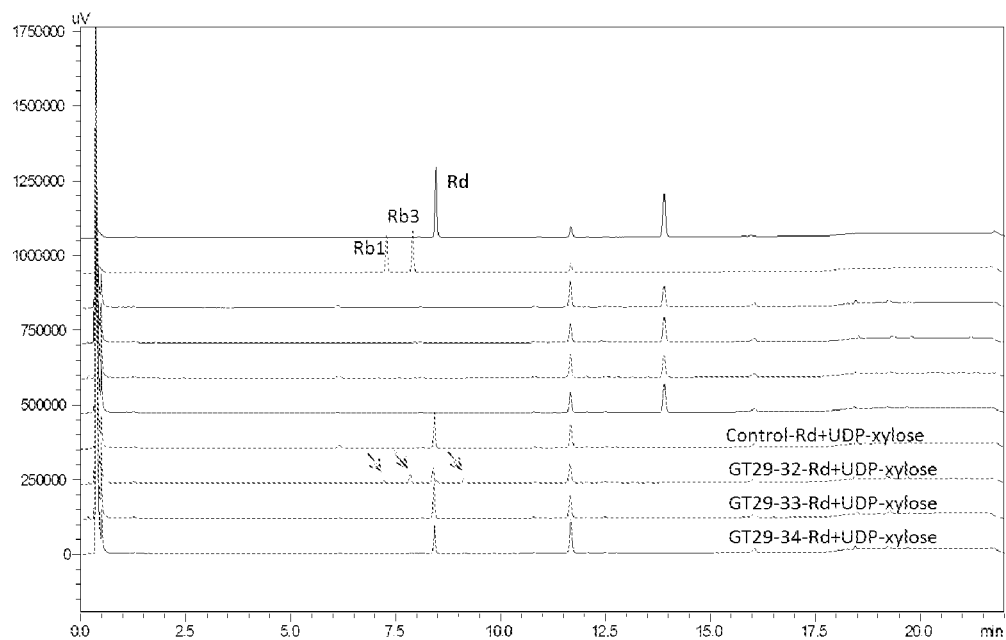
FIG. 4 shows an HPLC pattern of a transglycosyl reaction catalyzed by glycosyltransferases GT29-32, GT29-33, and GT29-34 with ginsenoside Rd as a glycosyl acceptor and UDP-xylose as a glycosyl donor. Control represents the lysate supernatant of the pet28a empty vector recombinant as an enzyme solution; GT29-32, GT29-33, and GT29-34 respectively represent the lysate supernatants of recombinant E. coli BL21-GT29-32, BL21-GT29-33 and BL21-GT29-34 as an enzyme solution.

Therefore, GT29-32 and GT29-34 can catalyze the C20-O-Glc of CK extension to a molecule of glucose to generate ginsenoside Gypenoside DOW. When UDP-xylose is used as a glycosyl donor, GT29-32 can catalyze Rd to produce three products. One of the products has the same mobility on TLC as Rb3, that is, GT29-32 can extend a molecule of xylose at C20-O-Glc to produce Rb3 (FIG. 2). The results of HPLC are consistent with those of TLC. GT29-32 catalyzes the production of three products from Rd and UDP-xylose (FIG. 4).

Figure 5:
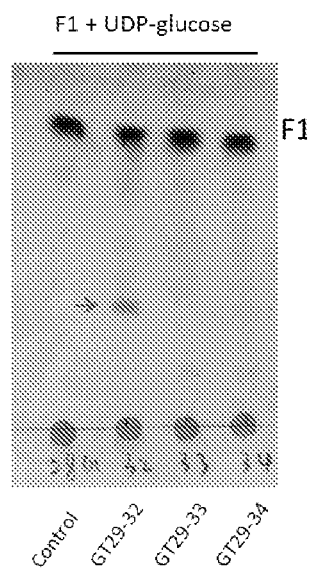
FIG. 5 shows a TLC pattern of a transglycosyl reaction catalyzed by glycosyltransferases GT29-32, GT29-33 and GT29-34 with ginsenoside F1 as a glycosyl acceptor and UDP-glucose as a glycosyl donor. Control represents the lysate supernatant of the pet28a empty vector recombinant as an enzyme solution; GT29-32, GT29-33, and GT29-34 respectively represent the lysate supernatants of recombinant E. coli BL21-GT29-32, BL21-GT29-33 and BL21-GT29-34 as an enzyme solution.
Figure 6:
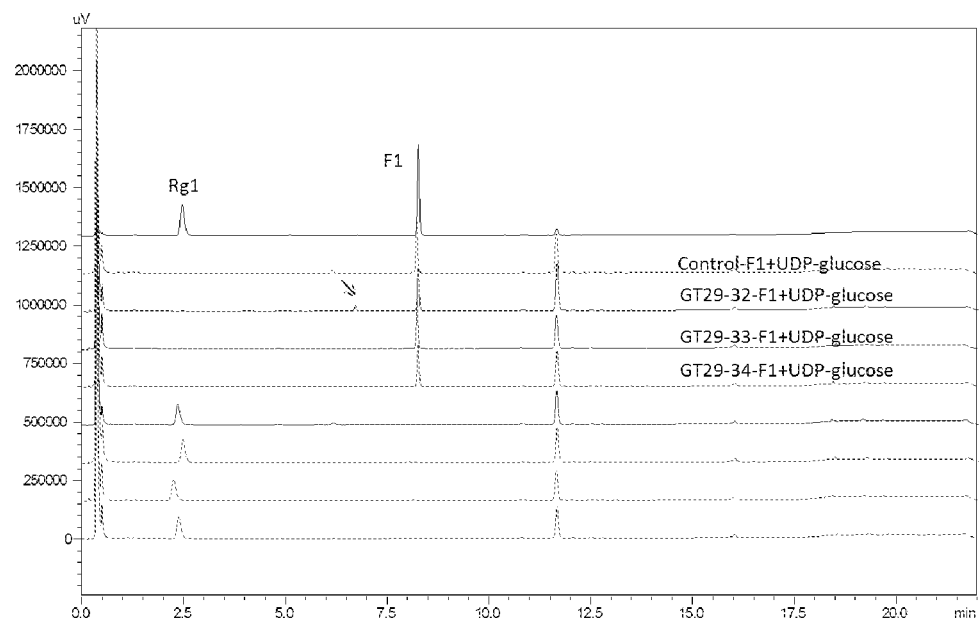
FIG. 6 shows an HPLC pattern of a transglycosyl reaction catalyzed by glycosyltransferases GT29-32, GT29-33, and GT29-34 using ginsenoside F1 as a glycosyl acceptor and UDP-glucose as a glycosyl donor. Control represents the lysate supernatant of the pet28a empty vector recombinant as an enzyme solution; GT29-32, GT29-33, and GT29-34 respectively represent the lysate supernatants of recombinant E. coli BL21-GT29-32, BL21-GT29-33 and BL21-GT29-34 as an enzyme solution.

Using Protopanaxatriol Ginsenoside F1 as a glycosyl acceptor and UDP-glucose as a glycosyl donor, GT29-32 can catalyze the formation of a new product. It is speculated that it also extends a molecule of glucose at C20-O-Glc of F1, the product is Notoginsenoside R3 (FIG. 5 and FIG. 6).

Figure 17:
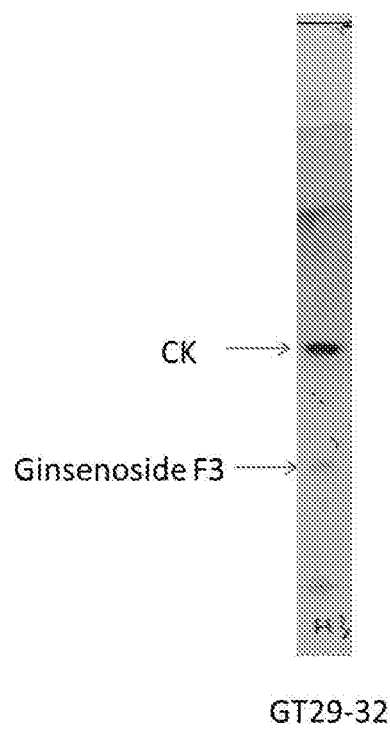
FIG. 17 shows a TLC pattern of a transglycosyl reaction catalyzed by glycosyltransferase GT29-32 using ginsenoside CK as a glycosyl acceptor and UDP-arabinose as a glycosyl donor. Control represents the lysate supernatant of the pet28a empty vector recombinant as an enzyme solution; GT29-32 represents the lysate supernatant of the recombinant E. coli BL21-GT29-32 as an enzyme solution.

Using Protopanaxadiol Ginsenoside CK as a glycosyl acceptor and UDP-arabinose as a glycosyl donor, GT29-32, GT29-33 and GT29-34 can catalyze the first glycosyl of C-20 of CK to extend an arabinosyl to generate Ginsenoside F3, wherein GT29-32 has the strongest activity (FIG. 17).

Example 4 Expression of Glycosyltransferase Genes GT29-4, GT29-5, GT29-7, GT29-9, GT29-11, GT29-13, GT29-17, GT29-18, GT29-24 and GT29-25 in E. coli Plasmids GT29-4-pMD18T, GT29-5-pMD18T, GT29-7-pMD18T, GT29 pMD18T, GT29-11-pMD18T, GT29-13-pMD18T, GT29-17-pMD18T, GT29 pMD18T, GT29-24-pMD18T and GT29-25-pMD18T containing GT29-4, GT29-5, GT29-7, GT29-9, GT29-11, GT29-13, GT29-17, GT29-18, GT29-24 and GT29-25 genes constructed in Example 1 were used as templates to amplify target genes GT29-4, GT29-5, GT29-7, GT29-9, GT29-11, GT29-13, GT29-17, GT29-18, GT29-24 and GT29-25 with the primers as shown in Table 1. After the expression vector pET28a (purchased from Merck) was digested with Ncol/SalI, GT29-11, GT29-13, GT29-17, GT29-18, GT29-24 and GT29-25 were cloned into pET28a (one-step cloning kit, purchased from Novizan), and E. coli expression vectors GT29-4-pET28a, GT29-5-pET28a, GT29-7-pET28a, GT29-9-pET28a, GT29-11-pET28a, GT29-13-pET28a, GT29-17-pET28a, GT29-18-pET28a, GT29-24-pET28a and GT29-25-pET28a were constructed.

Using the 6×His tag sequence on pET28a, recombinant proteins GT29-4-pET28a, GT29-5-pET28a, GT29-7-pET28a, GT29-9-pET28a, GT29-11-pET28a, GT29-13-pET28a, GT29-17-pET28a, GT29-18-pET28a, GT29-24 and GT29-25 had a 6×His tag at the C-terminal. The plasmids were transformed into commercially available E.

coli BL21 to construct recombinant strains BL21-GT29-4, BL21-GT29-5, BL21-GT29-7, BL21-GT29-9, BL21-GT29-11, BL21-GT29-13. BL21-GT29-17, BL21-GT29-18, BL21-GT29-24 and BL21-GT29-25. A recombinant was inoculated into LB medium, cultured at 37° C., 200 rpm to an OD600 of about 0.6-0.8, then the bacterial solution was cooled to 4° C., and IPTG with a final concentration of 100 µM was added, and induced expression was performed at 18° C., 120 rpm for 16 h. The bacteria was collected by centrifugation at 4° C., and the cells were disrupted by ultrasound. The supernatant of the cell lysate was collected by centrifugation at 12000 g at 4° C. for 10 min. The samples were taken for SDS-PAGE electrophoresis and western blot.

SDS-PAGE shows recombinant transformants of GT29-4-pET28a, GT29-5-pET28a, GT29-7-pET28a, GT29-9-pET28a, GT29-11-pET28a, GT29-13-pET28a, GT29-17-pET28a, GT29-18-pET28a, GT29-24-pET28a and GT29-25-pET28a were not significantly different from the cell lysate of the empty vector pET28a recombinant transformant, and the soluble expression levels were not obvious. Anti-6×His tag Western Blot shows that there was a clear band between 45 and 55 kD, and glycosyltransferases GT29-4, GT29-5, GT29-7, GT29-9, GT29-11, GT29-13, GT29-17, GT29-18, GT29-24 and GT29-25 had a small amount of soluble expression in *E. coli*.

Example 5 In Vitro Transglycosylation Activity and Products Identification of GT29-4, GT29-5, GT29-7, GT29-9, GT29-11, GT29-13, GT29-17, GT29-18, GT29-24 and GT29-25

The cell lysate supernatants of recombinant E. coli BL21-GT29-4, BL21-GT29-5, BL21-GT29-7, BL21-GT29-9, BL21-GT29-11, BL21-GT29-13, BL21-GT29-17, BL21-GT29-18, BL21-GT29-24 and BL21-GT29-25 in Example 2 was used as a crude enzyme solution for transglycosylation reaction, and cell lysate of recombinant *E. coli* with empty vector pET28a was used as a control.

Figure 7:
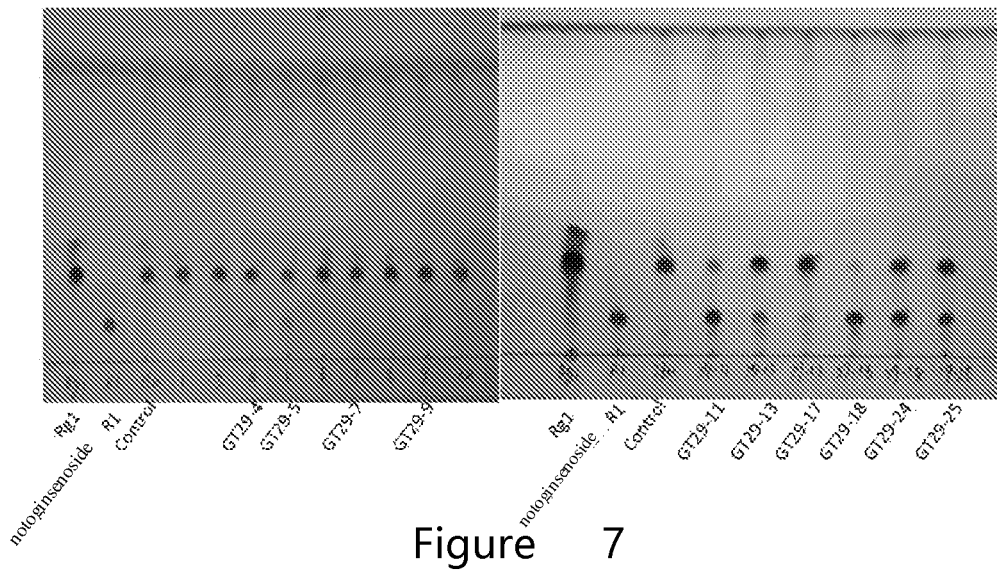
FIG. 7 shows a TLC pattern of a transglycosyl reaction catalyzed by the glycosyltransferases GT29-4, GT29-5, GT29-7, GT29-9, GT29-11, GT29-13, GT29-17, GT29-18, GT29-24 and GT29-25 with ginsenoside Rg1 as a glycosyl acceptor and UDP-xylose as a glycosyl donor. Control represents the lysate supernatant of the pet28a empty vector recombinant as an enzyme solution; GT29-4, GT29-5, GT29-7, GT29-9, GT29-11, GT29-13, GT29-17, GT29-18, GT29-24 and GT29-25 respectively represent the lysate supernatants of recombinant E. coli BL21-GT29-4, BL21-GT29-5, BL21-GT29-7, BL21-GT29-9, BL21-GT29-11, BL21-GT29-13, BL21-GT29-17, BL21-GT29-18, BL21-GT29-24 and BL21-GT29-25 as an enzyme solution.
Figure 8:
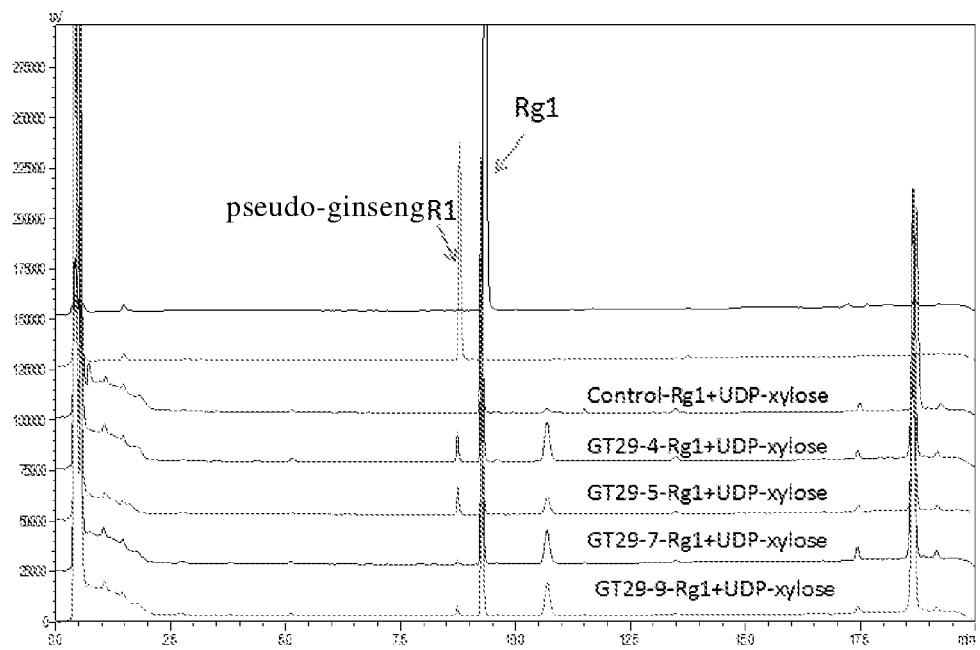
FIG. 8 shows an HPLC pattern of a transglycosyl reaction catalyzed by the glycosyltransferases GT29-4, GT29-5, GT29-7 and GT29-9 using ginsenoside Rg1 as a glycosyl acceptor and UDP-xylose as a glycosyl donor. Control represents the lysate supernatant of the pet28a empty vector recombinant as an enzyme solution; GT29-4, GT29-5, GT29-7, and GT29-9, respectively represents the lysate supernatants of recombinant E. coli BL21-GT29-4, BL21-GT29-5, BL21-GT29-7 and BL21-GT29-9 as an enzyme solution.
Figure 9:
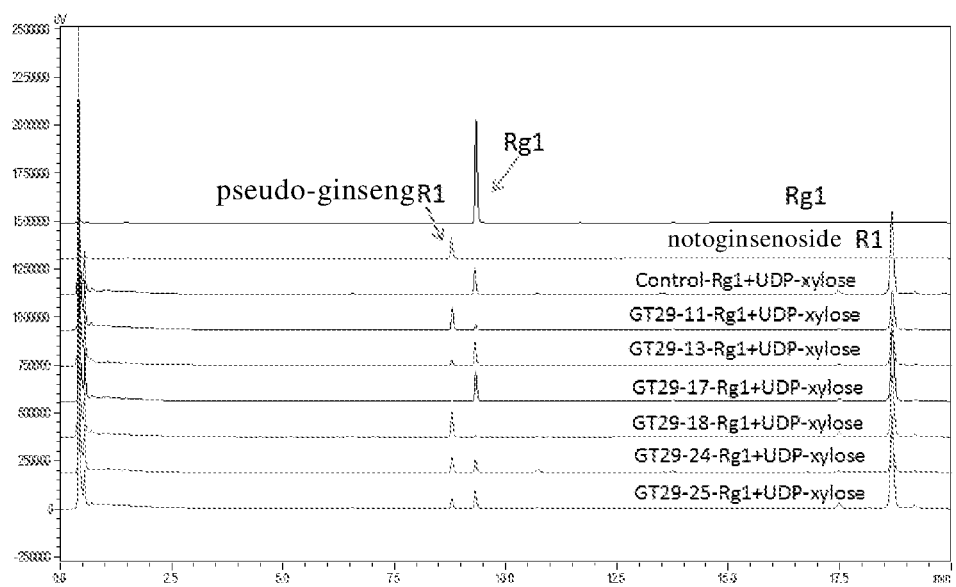
FIG. 9 shows an HPLC pattern of a transglycosyl reaction catalyzed by the glycosyltransferases GT29-11, GT29-13, GT29-17, GT29-18, GT29-24 and GT29-25 with the ginsenoside Rg1 as a glycosyl receptor and UDP-xylose as a glycosyl donor. Control represents the lysate supernatant of the pet28a empty vector recombinant as an enzyme solution; GT29-11, GT29-13, GT29-17, GT29-18, GT29-24 and GT29-25 respectively represent the lysate supernatants of recombinant E. coli BL21-GT29-11, BL21-GT29-13, BL21-GT29-17, BL21-GT29-18, BL21-GT29-24, and BL21-GT29-25 as an enzyme solution.

As shown in FIG. 7, using the Protopanaxadiol Ginsenoside Rg1 as a glycosyl acceptor, UDP-xylose as a glycosyl donor, GT29-4, GT29-5, GT29-7, GT29-9, GT29-11, GT29-13, GT29-17, GT29-18, GT29-24 and GT29-25 can catalyze the formation of Notoginsenoside RI. The HPLC results are consistent with the TLC results (FIG. 8 and FIG. 9). Therefore, GT29-4, GT29-5, GT29-7, GT29-9, GT29-11, GT29-13, GT29-17, GT29-18, GT29-24, and GT29-25 are capable of catalyzing the extension of C6-O-Glc of Rg1 by a molecule of xylose to produce notoginsenoside RI.

Figure 10:
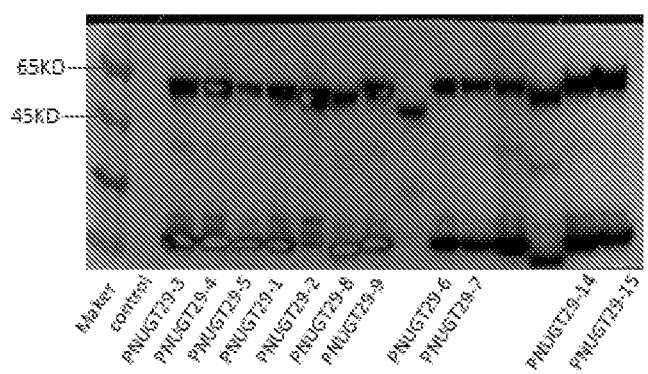
FIG. 10 shows Western blot detection for the protein expressions of glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, and PNUGT29-15. Control represents the lysate supernatant of the pet28a empty vector recombinant as an enzyme solution; PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 respectively represents the lysate supernatants of recombinant E. coli BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7, BL21-PNUGT29-8, BL21-PNUGT29-9, BL21-PNUGT29-14, and BL21-PNUGT29-15 as enzyme solution.

As shown in FIG. 10, GT29-24 and GT29-25 can use Protopanaxadiol Ginsenoside Rh2 as a glycosyl acceptor and UDP-glucose as a glycosyl donor to catalyze the production of ginsenoside Rg3 by extending a glucosyl at the C-3 glycosyl of Rh2. When the substrate is changed to F2, GT29-24 and GT29-25 can further catalyze the extension of a glucosyl at the C-3 glycosyl of F2 to produce ginsenoside Rd.

Example 6 Isolation of *Panax notoginseng* Glycosyltransferase and the Coding Gene Thereof RNA in *Panax notoginseng* was extracted and reverse transcription was performed to obtain cDNA of *Panax notoginseng*. Using this cDNA as a template, primer pair 1 (SEQ ID NO.: 82 and SEQ ID NO.: 83), primer pair 2 (SEQ ID NO.: 84 and SEQ ID NO.: 85), primer pair 3 (SEQ ID NO.: 84 and SEQ ID NO.: 86), primer pair 4 (SEQ ID NO.: 87 and SEQ ID NO.: 88) were used for PCR amplification to obtain a 1.4-1.5 kb amplification product. The high-fidelity KOD DNA polymerase from Bao Bioengineering Co., Ltd. was used as the DNA polymerase. PCR products were detected by agarose gel electrophoresis.

According to Example 1, several clones were selected to extract recombinant plasm ids and sequenced to obtain 14 different nucleic acid sequences, named PNUGT29-1 (SEQ ID NO.: 38), PNUGT29-2 (SEQ ID NO.: 40), PNUGT29-3 (SEQ ID NO.: 42), PNUGT29-4 (SEQ ID NO.: 44), PNUGT29-5 (SEQ ID NO.: 46), PNUGT29-6 (SEQ ID NO.: 48), PNUGT29-7 (SEQ ID NO.: 50), PNUGT29-8 (SEQ ID NO.: 52), PNUGT29-9 (SEQ ID NO.: 54), PNUGT29-14 (SEQ ID NO.: 56) and PNUGT29-15 (SEQ ID NO.: 58), respectively. BESTORF software was used to find ORF. Through sequence alignment, the amplification products all have the conserved functional domain of glycosyltransferase family 1, indicating that it is a glycosyltransferase gene.

PNUGT29-1: The glycosyltransferase gene PNUGT29-1 encodes a protein PNUGT29-1 containing 447 amino acids with the amino acid sequence as shown in SEQ ID NO: 39 in the sequence listing. The theoretical molecular weight of the protein is predicted to be 49.688 kDa by software, and the isoelectric point pI is 6.58.

PNUGT29-2: The glycosyltransferase gene PNUGT29-2 encodes a protein PNUGT29-2 containing 442 amino acids with the amino acid sequence as shown in SEQ ID NO: 41 in the sequence listing. The theoretical molecular weight of the protein is predicted to be 49.118 kDa by software, and the isoelectric point pI is 6.20.

PNUGT29-3: The glycosyltransferase gene PNUGT29-3 encodes a protein PNUGT29-3 containing 447 amino acids with the amino acid sequence as shown in SEQ ID NO: 43 in the sequence listing. The theoretical molecular weight of the protein is predicted to be 49.729 kDa by software, and the isoelectric point pI is 6.58.

PNUGT29-4: The glycosyltransferase gene PNUGT29-4 encodes a protein PNUGT29-4 containing 447 amino acids with the amino acid sequence as shown in SEQ ID NO: 45 in the sequence listing. The theoretical molecular weight of the protein is predicted to be 49.715 kDa by software, and the isoelectric point pI is 6.58.

PNUGT29-5: The glycosyltransferase gene PNUGT29-5 encodes a protein PNUGT29-5 containing 447 amino acids with the amino acid sequence as shown in SEQ ID NO: 47 in the sequence listing. The theoretical molecular weight of the protein is predicted to be 49.718 kDa by software, and the isoelectric point pI is 6.45.

PNUGT29-6: The glycosyltransferase gene PNUGT29-6 encodes a protein PNUGT29-6 containing 447 amino acids with the amino acid sequence as shown in SEQ ID NO: 49 in the sequence listing. The theoretical molecular weight of the protein is predicted to be 49.657 kDa by software, and the isoelectric point pI is 6.70.

PNUGT29-7: The glycosyltransferase gene PNUGT29-7 encodes a protein. PNUGT29-7 containing 447 amino acids with the amino acid sequence as shown in SEQ ID NO: 51 in the sequence listing. The theoretical molecular weight of the protein is predicted to be 49.749 kDa by software, and the isoelectric point pI is 6.58.

PNUGT29-8: The glycosyltransferase gene PNUGT29-8 encodes a protein. PNUGT29-8 containing 447 amino acids with the amino acid sequence as shown in SEQ ID NO: 53 in the sequence listing. The theoretical molecular weight of the protein is predicted to be 49.657 kDa by software, and the isoelectric point pI is 6.70.

PNUGT29-9: The glycosyltransferase gene PNUGT29-9 encodes a protein PNUGT29-9 containing 447 amino acids with the amino acid sequence as shown in SEQ ID NO: 55 in the sequence listing. The theoretical molecular weight of the protein is predicted to be 49.695 kDa by software, and the isoelectric point pI is 6.58.

PNUGT29-14: The glycosyltransferase gene PNUGT29-14 encodes a protein PNUGT29-14 containing 447 amino acids with the amino acid sequence as shown in SEQ ID NO: 57 in the sequence listing. The theoretical molecular weight of the protein is predicted to be 49.778 kDa by software, and the isoelectric point pI is 6.70. PNUGT29-15: The glycosyltransferase gene.

PNUGT29-15 encodes a protein PNUGT29-15 containing 447 amino acids with the amino acid sequence as shown in SEQ ID NO: 59 in the sequence listing. The theoretical molecular weight of the protein is predicted to be 49.755 kDa by software, and the isoelectric point p1 is 6.63.

Example 7 Expression of *Panax notoginseng* Glycosyltransferase Genes PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 and NUGT29-15 in *E. coli*

Plasmids PNUGT29-1-pMD18T, PNUGT29-2-pMD18T, PNUGT29-3-pMD18T, PNUGT29-4-pMD18T, PNUGT29-5-pMD18T, PNUGT29-6-pMD18T, PNUGT29-7-pMD18T, PNUGT29-8-pMD18T, PNUGT29-9-pMD18T, PNUGT29-14-pMD18T and PNUGT29-15-pMD18T containing PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 and PNUGT29-15 genes constructed in Example 6 were used as a template, and the target genes PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 and PNUGT29-15 were amplified with the primers as shown in Table 1. Referring to the method in Example 2, the recombinant strains BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7. BL21-PNUGT29-8, BL21-PNUGT29-9, BL21-PNUGT29-14 and BL21-PNUGT29-15 were constructed for SDS-PAGE electrophoresis and western blot. Anti-6×His tag Western Blot (FIG. 10) shows that there is a clear band between 45 and 65 kD, glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 and PNUGT29-15 have a small amount of soluble expression in *E. coli*.

TABLE 2

| primers used to amplify genes | | |
|---|---|---|
| gene | primer | SEQ ID NO. |
| PNUGT29-1 | PNUGT29-1-F | 60 |
| | PNUGT29-1-R | 61 |
| PNUGT29-2 | PNUGT29-2-F | 62 |
| | PNUGT29-2-R | 63 |
| PNUGT29-3 | PNUGT29-3-F | 64 |
| | PNUGT29-3-R | 65 |
| PNUGT29-4 | PNUGT29-4-F | 66 |
| | PNUGT29-4-R | 67 |
| PNUGT29-5 | PNUGT29-5-F | 68 |
| | PNUGT29-5-R | 69 |

TABLE 2-continued

| primers used to amplify genes | | |
|---|---|---|
| gene | primer | SEQ ID NO. |
| PNUGT29-6 | PNUGT29-6-F | 70 |
| | PNUGT29-6-R | 71 |
| PNUGT29-7 | PNUGT29-7-F | 72 |
| | PNUGT29-7-R | 73 |
| PNUGT29-8 | PNUGT29-8-F | 74 |
| | PNUGT29-8-R | 75 |
| PNUGT29-9 | PNUGT29-9-F | 76 |
| | PNUGT29-9-R | 77 |
| PNUGT29-14 | PNUGT29-14-F | 78 |
| | PNUGT29-14-R | 79 |
| PNUGT29-15 | PNUGT29-15-F | 80 |
| | PNUGT29-15-R | 81 |

Example 8 In Vitro Transglycosylation Activity and Product Identification of *Panax notoginseng* Glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14 and PNUGT29-15

The cell lysate supernatants of recombinant *E. coli* BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7, BL21-PNUGT29-8, BL21-PNUGT29-9, BL21-PNUGT29-14 and BL21-PNUGT29-15 in Example 7 were used as a crude enzyme solution for transglycosylation reaction. Cell lysate of recombinant *E. coli* with empty vector pET28a was used as a control.

Figure 11:
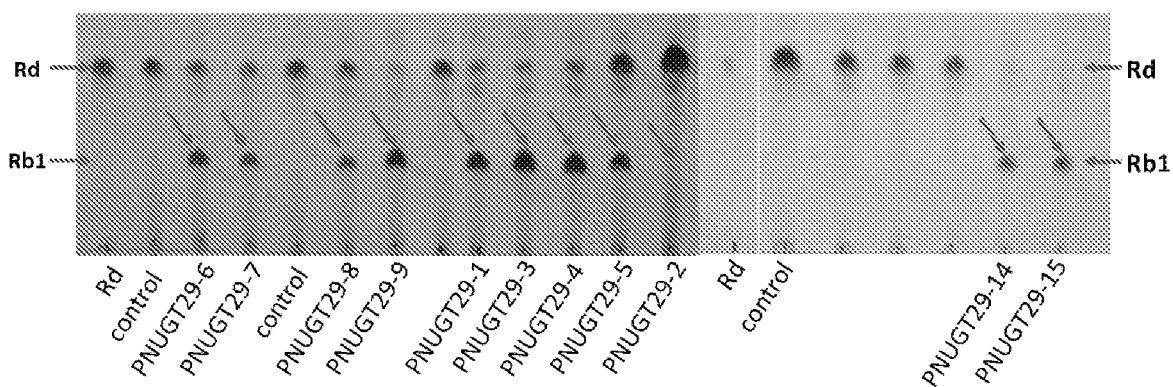
FIG. 11 shows a TLC pattern of a transglycosyl reaction catalyzed by the glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, and PNUGT29-15 with the ginsenoside Rd as a glycosyl acceptor and UDP-glucose as a glycosyl donor. Control represents the lysate supernatant of the pet28a empty vector recombinant as an enzyme solution; PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 respectively represents the lysate supernatants of recombinant E. coli BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7, BL21-PNUGT29-8, BL21-PNUGT29-9, BL21-PNUGT29-14, and BL21-PNUGT29-15 as an enzyme solution.

As shown in FIG. 11: using Protopanaxadiol Ginsenoside Rd as a glycosyl acceptor, UDP-glucose as a glycosyl donor, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 can catalyze the extension of a glucosyl at the C-20 glycosyl of Rd to generate Rb1.

Figure 12:
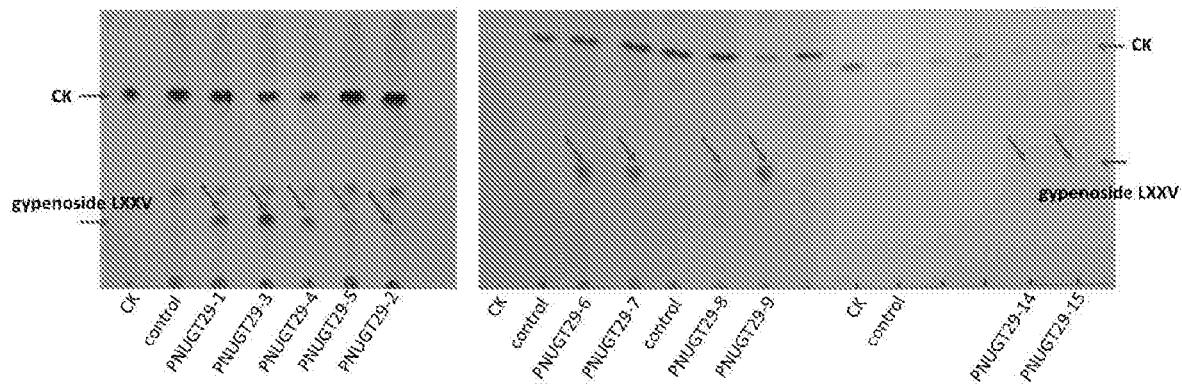
FIG. 12 shows a TLC pattern of a transglycosyl reaction catalyzed by the glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, and PNUGT29-15 with the ginsenoside CK as glycosyl acceptor and UDP-glucose as a glycosyl donor. Control represents the lysate supernatant of the pet28a empty vector recombinant as an enzyme solution; PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 respectively represents the lysate supernatants of recombinant E. coli BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7, BL21-PNUGT29-8, BL21-PNUGT29-9, BL21-PNUGT29-14, and BL21-PNUGT29-15 as an enzyme solution.

As shown in FIG. 12: using Protopanaxadiol Ginsenoside CK as a glycosyl acceptor, UDP-glucose as a glycosyl donor, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 can catalyze the extension of a glucosyl at the C-20 glycosyl to generate Gypenoside LXXV.

Figure 13:
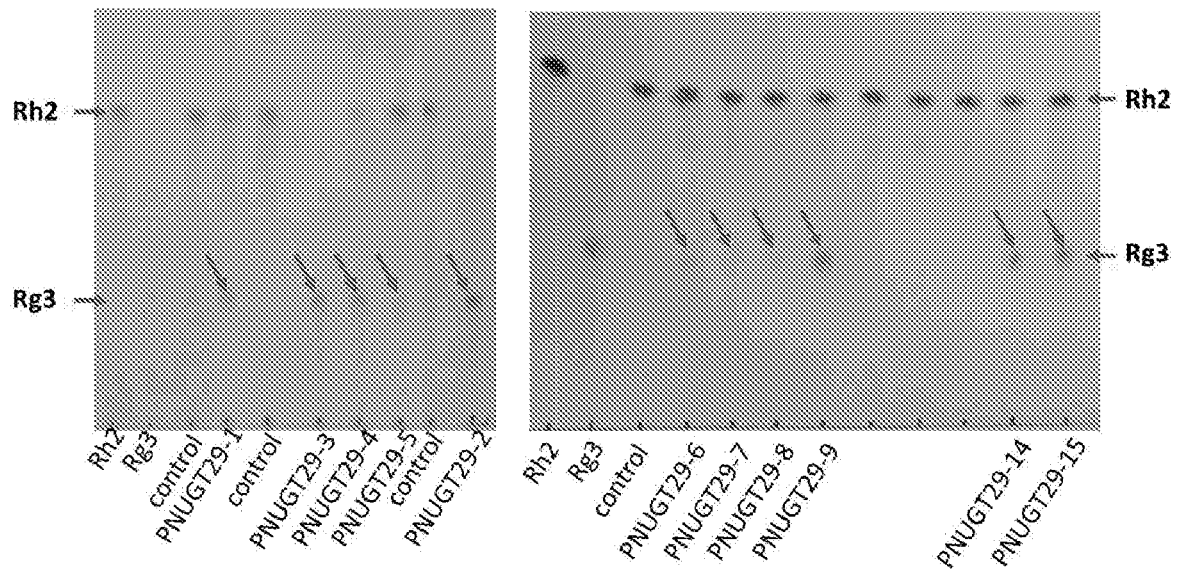
FIG. 13 shows a TLC pattern of a transglycosyl reaction catalyzed by the glycosyltransferases PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, and PNUGT29-15 with the ginsenoside Rh2 as a glycosyl acceptor and UDP-glucose as a glycosyl donor. Control represents the lysate supernatant of the pet28a empty vector recombinant as an enzyme solution; PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 respectively represents the lysate supernatants of recombinant E. coli BL21-PNUGT29-1, BL21-PNUGT29-2, BL21-PNUGT29-3, BL21-PNUGT29-4, BL21-PNUGT29-5, BL21-PNUGT29-6, BL21-PNUGT29-7, BL21-PNUGT29-8, BL21-PNUGT29-9, BL21-PNUGT29-14, and BL21-PNUGT29-15 as enzyme solution.

As shown in FIG. 13: using Protopanaxadiol Ginsenoside Rh2 as a glycosyl acceptor, UDP-glucose as a glycosyl donor, PNUGT29-1, PNUGT29-2, PNUGT29-3, PNUGT29-4, PNUGT29-5, PNUGT29-6, PNUGT29-7, PNUGT29-8, PNUGT29-9, PNUGT29-14, PNUGT29-15 can catalyze the extension of a glucosyl at the C-3 glycosyl of Rh2 to generate Rg3.

Example 9 Expression of Glycosyltransferase Genes GT29-19, GT29-20, GT29-21, GT29-22, GT29-23, GT29-36, GT29-37, GT29-42, GT29-43, GT29-45 and GT29-46 in *E. coli*

Plasmids GT29-19-pMD18T, GT29-20-pMD18T, GT29-21-pMD18T, GT29-22-pMD18T, GT29-23-pMD18T, GT29-36-pMD18T, GT29-37-pMD18T, GT29-42-pMD18T, GT29-43-pMD18T, GT29-45-pMD18T, and GT29-46-pMD18T containing GT29-19, GT29-20, GT29-21, GT29-22, GT29-23, GT29-36, GT29-37, GT29-42, GT29-43, GT29-45 and GT29-46 genes constructed in Example 1 were used as a template, and the target genes GT29-36, GT29-37, GT29-42, GT29-43, GT29-45 and GT29-46 were amplified with the primers as shown in Table 1.

Referring to Example 2, recombinant strains BL21-GT29-19, BL21-GT29-20, BL21-GT29-21, BL21-GT29-22, BL21-GT29-23, BL21-GT29-36, BL21-GT29-37, BL21-GT29-42, BL21-GT29-43, BL21-GT29-45 and BL21-GT29-46 were constructed, and samples were taken for SDS-PAGE electrophoresis and western blot.

Figure 15:
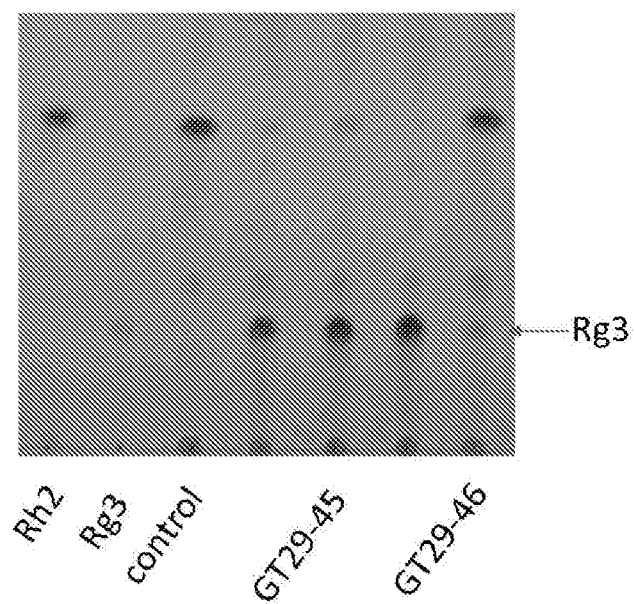
FIG. 15 shows a TLC pattern of a transglycosyl reaction catalyzed by the glycosyltransferase GT29-45 and GT29-46 using ginsenoside Rh2 as a glycosyl acceptor and UDP-glucose as a glycosyl donor. Control represents the lysate supernatant of the pet28a empty vector recombinant as an enzyme solution; GT29-45 and GT29-46 respectively represents the lysate supernatant of the recombinant E. coli BL21-GT29-45 and BL21-GT29-46 as an enzyme solution.

Protopanaxadiol Ginsenoside Rh2 was used as a glycosyl acceptor, and UDP-glucose was used as a glycosyl donor, and the above-mentioned glycosyltransferases GT29-19, GT29-20, GT29-21, GT29-22, GT29-23, GT29-36, GT29-37, GT29-42, GT29-43, GT29-45 and GT29-46 can all catalyze the extension of a glycosyl at the C-3 glycosyl of Rh2 to generate Rg3. FIG. 15 shows GT29-45 and GT29-46 can catalyze Rh2 to generate Rg3.

Figure 14:
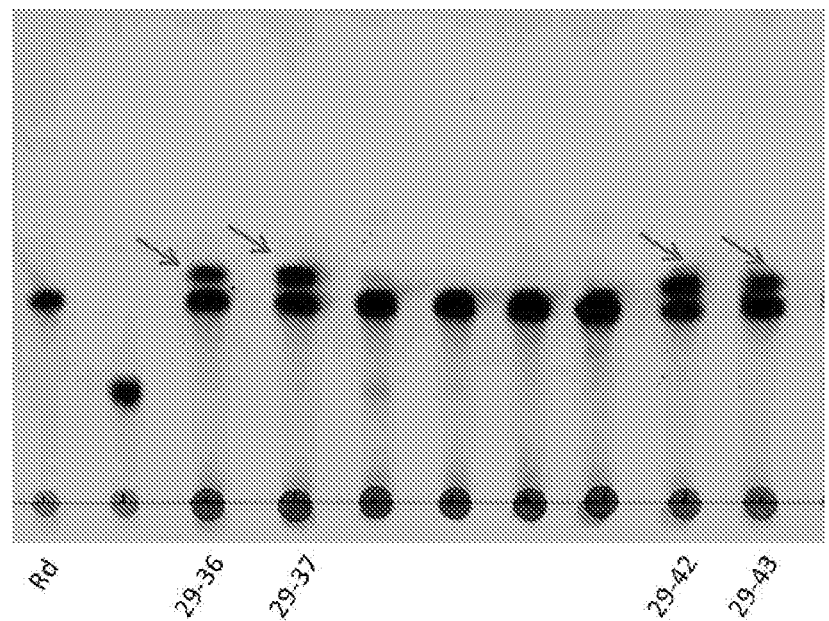
FIG. 14 shows a TLC pattern of a transglycosyl reaction catalyzed by the glycosyltransferases GT29-36, GT29-36, GT29-42 and GT29-43 with ginsenoside Rd as a glycosyl acceptor and UDP-xylose as a glycosyl donor. GT29-36, GT29-36, GT29-42 and GT29-43 respectively represents the lysate supernatants of recombinant E. coli BL21-GT29-36, BL21-GT29-36, BL21-GT29-42 and BL21-GT29-43 as an enzyme solution.

Protopanaxadiol Ginsenoside Rd was used as a glycosyl acceptor and UDP-xylose was used as a glycosyl donor, and the above glycosyltransferases GT29-19, GT29-20, GT29-21, GT29-22, GT29-23, GT29-36, GT29-37, GT29-42, GT29-43 can all catalyze the replacement of the second glucose at C-3 position of Rd with xylose to produce a new triterpene saponin (3-O-β-(D-xylopyranosyl)-β-(D-glucopyranosyl), 20-O-β-(D-glucopyranosyl)-PPD), of which GT29-36, GT29-37, GT29-42 and GT29-43 are the most active (FIG. 14).

Figure 16:
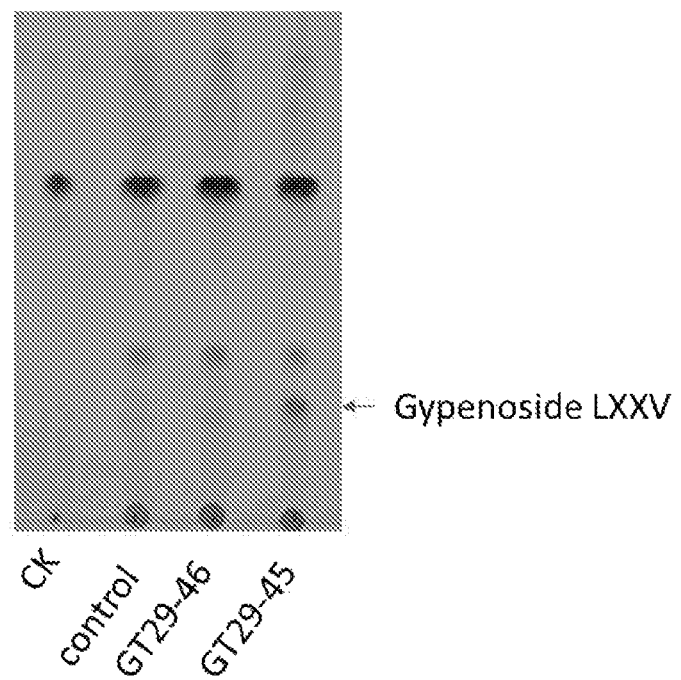
FIG. 16 shows a TLC pattern of a transglycosyl reaction catalyzed by glycosyltransferases GT29-45 and GT29-46 using ginsenoside CK as a glycosyl acceptor and UDP-glucose as a glycosyl donor. Control represents the lysate supernatant of the pet28a empty vector recombinant as an enzyme solution; GT29-45 and GT29-46 respectively represents the lysate supernatant of the recombinant E. coli BL21-GT29-45 and BL21-GT29-46 as an enzyme solution.

As shown in FIG. 16: Protopanaxadiol Ginsenoside CK is used as a glycosyl acceptor, and UDP-glucose is used as a glycosyl donor. GT29-45 and GT29-46 can catalyze the C-20 glycosyl of CK to extend a glucosyl to produce Gypenoside LXXV, in which GT29-45 has a strong activity.

Example 10 Further Verification of the Glycosyltransferase Activity

The above Examples 3, 5, and 8 were repeated, and the difference was that other glycosyl donors and substrates were replaced, and the experimental results are shown in Table 3 to Table 5:

TABLE 3

| SEQ ID NO.: | name | C-3 UDP-xylose Rd | UDP-G F2 | UDP-G Rh2 |
|---|---|---|---|---|
| 116 | GT29-19 | ++ | ++ | +++ |
| 118 | GT29-20 | ++ | ++ | +++ |
| 120 | GT29-21 | + | ++ | +++ |
| 122 | GT29-22 | + | ++ | ++ |
| 124 | GT29-23 | + | ++ | ++ |
| 90 | GT29-36 | +++ | ++ | ++ |
| 92 | GT29-37 | +++ | ++ | ++ |
| 94 | GT29-42 | +++ | ++ | ++ |
| 96 | GT29-43 | +++ | ++ | ++ |
| 98 | GT29-45 | NS | ++ | ++ |
| 100 | GT29-46 | NS | ++ | ++ |
| 39 | PNUGT29-1 | NS | ++ | +++ |
| 41 | PNUGT29-2 | NS | +++ | +++ |
| 43 | PNUGT29-3 | NS | +++ | +++ |
| 45 | PNUGT29-4 | NS | +++ | +++ |
| 47 | PNUGT29-5 | NS | ++ | ++ |
| 49 | PNUGT29-6 | NS | ++ | ++ |
| 51 | PNUGT29-7 | NS | ++ | ++ |
| 53 | PNUGT29-8 | NS | ++ | ++ |
| 55 | PNUGT29-9 | NS | +++ | +++ |
| 57 | PNUGT29-14 | NS | ++ | ++ |
| 59 | PNUGT29-15 | NS | ++ | ++ |

TABLE 4

| SEQ ID NO.: | name | C-6 UDP-xylose Rg1 | C-6 UDP-xylose Rh1 | C-6 UDP-G Rg1 | C-6 UDP-G Rh1 |
|---|---|---|---|---|---|
| 12 | GT29-4 | ++ | ++ | + | + |
| 14 | GT29-5 | ++ | ++ | + | + |
| 16 | GT29-7 | +++ | ++ | ++ | ++ |
| 18 | GT29-9 | ++ | ++ | + | + |
| 20 | GT29-11 | +++ | +++ | ++ | ++ |
| 22 | GT29-13 | ++ | ++ | ++ | ++ |
| 24 | GT29-17 | ++ | ++ | + | + |
| 26 | GT29-18 | +++ | +++ | ++ | ++ |
| 28 | GT29-24 | +++ | +++ | ++ | ++ |
| 30 | GT29-25 | +++ | +++ | + | + |

TABLE 5

| SEQ ID NO.: | name | C-20 UDP-xylose Rd | C-20 UDP-G CK | C-20 UDP-G F1 | C-20 UDP-arabinose Rd | C-20 UDP-arabinose CK |
|---|---|---|---|---|---|---|
| 4 | GT29-32 | +++ | +++ | ++ | + | ++ |
| 6 | GT29-33 | + | ++ | + | ++ | ++ |
| 8 | GT29-34 | + | ++ | + | ++ | ++ |
| 98 | GT29-45 | + | ++ | + | + | NS |
| 100 | GT29-46 | + | + | + | + | NS |
| 39 | PNUGT29-1 | + | +++ | + | + | NS |
| 41 | PNUGT29-2 | + | + | + | + | NS |
| 43 | PNUGT29-3 | + | +++ | ++ | + | NS |
| 45 | PNUGT29-4 | + | +++ | ++ | ++ | NS |
| 47 | PNUGT29-5 | + | +++ | + | ++ | NS |
| 49 | PNUGT29-6 | + | +++ | ++ | ++ | NS |
| 51 | PNUGT29-7 | + | +++ | + | + | NS |
| 53 | PNUGT29-8 | + | +++ | + | + | NS |
| 55 | PNUGT29-9 | + | +++ | + | + | NS |
| 57 | PNUGT29-14 | + | +++ | + | + | NS |
| 59 | PNUGT29-15 | + | +++ | + | + | NS |

* NS stands for not shown

It can be seen from Tables 3 to 5 that the glycosyltransferases of the present invention can utilize common glycosyl donors and substrates, and have glycosyl extension or glycosyl substitution activity on different sites of tetracyclic triterpenes.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. An in vitro glycosylation method, comprising the steps of:
   (i) transforming or transducing a host cell with a polynucleotide encoding a glycosyltransferase, or with a recombinant expression vector containing the polynucleotide;
   (ii) culturing the host cell in a culture medium, thereby expressing the glycosyltransferase;
   (iii) isolating and purifying the glycosyltransferase from the culture medium or the host cell; and
   (iv) transferring a glycosyl group from a glycosyl donor to one of the following positions of a tetracyclic triterpenoid with the glycosyltransferase:
   the first glycosyl group on position C20 and/or position C3 of the tetracyclic triterpenoid; and
   thereby forming a glycosylated tetracyclic triterpenoid;
   wherein the glycosyltransferase comprises SEQ ID NO:43 or a derivative polypeptide thereof; and wherein the derivative polypeptide, having glycosyltransferase activity, is formed by adding a tag sequence, a signal sequence or a secretion signal sequence to SEQ ID NO:43.

2. A method for catalyzing one or more glycosyl group transferring reactions, comprising
   (i) transforming or transducing a host cell with a polynucleotide encoding a glycosyltransferase, or with a recombinant expression vector containing the polynucleotide;
   (ii) culturing the host cell in a culture medium, thereby expressing the glycosyltransferase;
   (iii) isolating and purifying the glycosyltransferase from the culture medium or the host cell; and
   (iv) transferring the one or more glycosyl group from a glycosyl donor to the following positions of a tetracyclic triterpenoid with the glycosyltransferase to extend a carbohydrate chain, thereby catalyzing one or more of the following glycosyl group transferring reactions:
   (a) the first glycosyl group on position C20 of the tetracyclic triterpenoid;
   and/or
   (b) the first glycosyl group on position C3 of the tetracyclic triterpenoid;
   wherein the glycosyltransferase comprises SEQ ID NO:43 or a derivative polypeptide thereof; and
   wherein the derivative polypeptide, having glycosyltransferase activity, is formed by adding a tag sequence, a signal sequence or a secretion signal sequence to SEQ ID NO:43.

* * * * *